(12) United States Patent
Palto

(10) Patent No.: US 7,889,297 B2
(45) Date of Patent: Feb. 15, 2011

(54) LIQUID CRYSTAL DISPLAY OPERATING IN A VERTICALLY ALIGNED MODE

(75) Inventor: Serguei Petrovich Palto, Moscow Region (RU)

(73) Assignee: Crysoptix, KK, Tokyo (JP)

( * ) Notice: Subject to any disclaimer, the term of this patent is extended or adjusted under 35 U.S.C. 154(b) by 253 days.

(21) Appl. No.: 12/302,893

(22) PCT Filed: Jun. 6, 2007

(86) PCT No.: PCT/EP2007/005047

§ 371 (c)(1),
(2), (4) Date: Dec. 1, 2008

(87) PCT Pub. No.: WO2007/141025

PCT Pub. Date: Dec. 13, 2007

(65) Prior Publication Data

US 2010/0118241 A1    May 13, 2010

(30) Foreign Application Priority Data

Jun. 6, 2006  (GB) ................................ 0611184.3
May 18, 2007  (GB) ................................ 0709607.6

(51) Int. Cl.
*G02F 1/1335* (2006.01)
(52) U.S. Cl. ...................... 349/118; 349/117
(58) Field of Classification Search .......... 349/117–118
See application file for complete search history.

(56) References Cited

U.S. PATENT DOCUMENTS 5,298,199 A   3/1994  Hirose et al.
5,739,296 A * 4/1998  Gvon et al. .................. 534/577
6,142,075 A   11/2000 Koch et al.
6,281,956 B1  8/2001  Ohmuro et al.
6,339,460 B1  1/2002  Saitoh (Continued)

FOREIGN PATENT DOCUMENTS

WO    2004068223 A    8/2004

(Continued)

OTHER PUBLICATIONS

Ignatov et al., "Molecular Alignment in Nano-Film Crystal Polarizers and Retarders," Proc. of the SPIE, Jul. 7, 2002, vol. 4807, pp. 177-188.

(Continued)

*Primary Examiner*—Rhonda S Peace
(74) *Attorney, Agent, or Firm*—Houst Consulting

(57) ABSTRACT

The present invention relates generally to the field of liquid crystal display devices and more particularly to a liquid crystal display device operating in vertically aligned mode (VA-mode) in which liquid crystal molecules having a negative dielectric anisotropy are aligned generally perpendicularly to a panel surface of the liquid crystal display. A liquid crystal display according to the invention comprises a liquid crystal cell (6) of a vertical alignment mode, at least one polarizer (2, 10) arranged on each side of the liquid crystal cell, and at least one compensating structure (3, 7) disposed between the liquid crystal cell and at least one of the polarizers. The polarizers have transmission axes (11, 18) which are perpendicular to each other.

32 Claims, 32 Drawing Sheets

U.S. PATENT DOCUMENTS

| | | | |
|---|---|---|---|
| 7,527,834 B2 * | 5/2009 | Paukshto et al. | ............ 428/1.1 |
| 2003/0103182 A1 | 6/2003 | Mi et al. | |
| 2005/0190326 A1 | 9/2005 | Jeon et al. | |

FOREIGN PATENT DOCUMENTS

| | | |
|---|---|---|
| WO | 2004068225 A | 8/2004 |
| WO | 2004068226 A | 8/2004 |
| WO | 2005051926 A | 6/2005 |
| WO | 2006025474 A | 3/2006 |

OTHER PUBLICATIONS

Qi et al., "Extraordinarily High-contrast and Wide-view Liquid Crystal Displays," Applied Physics Letters, 2005, 86,121107.

PCT, International Search Report and Written Opinion of the International Searching Authority in PCT/EP2007/005047, Aug. 5, 2008, 16 pages.

* cited by examiner

LIQUID CRYSTAL DISPLAY OPERATING IN A VERTICALLY ALIGNED MODE

RELATED APPLICATIONS

This application is related to UK patent application no. 0520489.6 filed on Oct. 7, 2005 and UK patent application no. 0620026.5 filed on Oct. 8, 2006, entitled "Organic Compound, Optical Crystal Film and Method of Production Thereof", UK patent application no. 0616359.6 filed on Aug. 16, 2006, entitled "Organic Compound, Optical Film and Method of Production Thereof" and the UK patent application of the same title filed on 18 May 2007, the entire disclosure of which is incorporated by reference herein.

The present invention generally relates to a liquid crystal display and more particularly to a liquid crystal display operating in a vertically aligned mode (VA-mode) in which liquid crystal molecules having a negative dielectric anisotropy are aligned generally perpendicular to a panel surface of the liquid crystal display.

Liquid crystal displays are used as displays for various information processing apparatuses such as a computer. Liquid crystal displays, having a compact size and consuming little electric power, are particularly suitable for application in portable information processing apparatuses. On the other hand, use of such liquid crystal displays in a fixed-type information processing apparatus such as a desktop-type computer, is also being studied. Conventional liquid crystal displays generally use a twisted nematic mode (TN-mode) construction in which liquid crystal molecules having a positive dielectric anisotropy are aligned horizontally between a pair of mutually opposing panel substrates, wherein the liquid crystal molecules adjacent one panel substrate and the liquid crystal molecules adjacent the other panel substrate are aligned in respective directions crossing with each other perpendicularly. In such a TN-mode liquid crystal display, various liquid crystals are already developed, and the liquid crystal display can be fabricated by a well-established process with low cost. On the other hand, a TN-mode liquid crystal display has a drawback in realizing a high contrast representation of images. It should be noted that a TN-mode liquid crystal display provides a black representation by causing the liquid crystal molecules to align vertically to the surface of the panel substrate by applying a driving electric field, while the liquid crystal molecules immediately adjacent the panel substrate tend to maintain the horizontal alignment even when the driving electric field is applied. Thereby, the birefringence associated with such horizontal liquid crystal molecules allows a passage of light even in the activated state in which the passage of light through the liquid crystal layer should be interrupted completely. Thus, there occurs a leakage of light or coloring of the panel when an attempt is made in a TN-mode liquid crystal display to display a white image on a black background (so-called "normally black mode") as is commonly adopted in a CRT (cathode-ray tube) display, and the black state or level becomes worse than that of a "normally white mode," in which black images are displayed on a white background, because of dispersion. This is the reason why conventional TN-mode liquid crystal display devices are operated in the normally white mode. A VA-mode liquid crystal display is a liquid crystal display in which liquid crystal molecules having a negative dielectric anisotropy are confined between a pair of panel substrates in a state that the liquid crystal molecules are aligned in a direction generally perpendicular to the surface of the panel substrates in the non-activated state of the liquid crystal display. Thus, light passes through a liquid crystal layer in such a liquid crystal display without changing the polarization plane thereof in the non-activated state of the liquid crystal cell, and the light is effectively interrupted by a pair of polarizers disposed at both sides of the liquid crystal layer in a crossed state. In such a VA-mode liquid crystal display, therefore, it is possible to achieve a near-ideal black representation in the non-activated state of the liquid crystal display. In other words, such a VA-mode liquid crystal display can easily achieve a very high contrast representation not possible by a TN-mode liquid crystal display. In the activated state of a VA-mode liquid crystal display, it should be noted that the liquid crystal molecules are aligned generally parallel to the panel substrates due to the electric field applied to the liquid crystal molecules, and a rotation is induced in the polarization state of an incident optical beam. The VA mode itself has been known for a long time. On the other hand, it has been thought conventionally that a VA-mode liquid crystal display cannot provide the quality of representation compared to that of a TN-mode liquid crystal display, in terms of viewing angle characteristics, voltage retention (or voltage holding ratio), and the like. Thus, little effort has been made so far for realizing a practical liquid crystal display device using a VA-mode liquid crystal. Particularly, it has been believed that construction of an active-matrix liquid crystal display device that uses thin-film transistors (TFT) is very difficult. As a VA-mode liquid crystal can provide a contrast ratio superior to that of a conventional CRT display, it is predicted that the major target of such a VA-mode liquid crystal display device would be to replace conventional CRT display devices. In order to achieve this target, however, it is particularly necessary to improve the viewing angle characteristics of the display device, in addition to usual requirements of increasing the display area and improving the response.

In connection with polarization, compensation layers, retardation layers, films and plates described in the present application, the following definitions of terms are used throughout the text.

The term optical axis refers to a direction in which propagating light does not exhibit birefringence.

Any optically anisotropic medium is characterized by its second-rank dielectric permittivity tensor. A dielectric permittivity of any medium is determined by polarizability of particles forming this medium. If the medium comprises supramolecules then the dielectric permittivity of the medium is determined by orientation and polarizability of these supramolecules.

The classification of compensator plates is tightly connected to orientations of the principal axes of a particular permittivity tensor with respect to the natural coordinate frame of the plate. The natural xyz coordinate frame of the plate is chosen so that the z-axis is parallel to the normal direction and the xy plane coincides with the plate surface. FIG. 1 demonstrates a general case when the principal axes (A, B, C) of the permittivity tensor are arbitrarily oriented relative to the xyz frame.

Orientations of the principal axes can be characterized using three Euler's angles $(\theta, \phi, \psi)$ which, together with the principal permittivity tensor components $(\epsilon_A, \epsilon_B, \epsilon_C)$, uniquely define different types of optical compensators (FIG. 1). The case when all the principal components of the permittivity tensor have different values corresponds to a biaxial compensator, whereby the plate has two optical axes. For instance, in the case of $\epsilon_A < \epsilon_B < \epsilon_C$, these optical axes are in the plane of C and A axes on both sides from the C axis. In the uniaxial limit, when $\epsilon_A = \epsilon_B$, we have a degenerate case when the two axes coincide and the C axis is a single optical axis.

In the important particular case the two principal axes A and B of the dielectric tensor lie in the layer plane, while the axis C is normal to it. The x, y and z-axes of the laboratory frame can be chosen coinciding with A, B and C axes respectively. If, for instance, the lowest and highest magnitudes of the three principal values $\in_A$, $\in_B$, and $\in_C$ of the dielectric permittivity tensor correspond to the A and B axes respectively then $\in_A < \in_C < \in_B$, and the two optical axes belong to the AB plane. For this reason such retardation layer is named as "$A_B$" or "$B_A$" type plate (FIG. 2). The negative $A_B$ plate, when $\in_A - \in_B < 0$, is equivalent to positive $B_A$ plate (replacing the order of the naming letters changes the sign of the dielectric permittivity difference: $\in_B - \in_A > 0$). Another fundamentally different case is when the two optical axes belong to the plane orthogonal to the plate surface. This case takes place if the lowest or highest magnitude of one of the principal permittivity corresponds to the C-axis. For instance, in case of $\in_C < \in_B < \in_A$ this retardation layer is named as the negative $C_A$ or positive $A_C$ plate.

The zenith angle θ between the C axis and the z axis is most important in the definitions of various compensator types. There are several important types of uniaxial retardation layers, which are most frequently used in practice for compensation of LCD.

A C-plate is defined by the Euler angle θ=0 and $\in_A = \in_B \neq \in_C$. In this case, the principal C axis (extraordinary axis) is normal to the plate surface (xy plane). In cases of $\in_A = \in_B < \in_C$, the plate is called "positive C-plate". On the contrary, if $\in_A = \in_B > \in_C$, the plate is referred to as the "negative C-plate". FIG. 3 shows the orientation of the principal axes of a particular permittivity tensor with respect to the natural coordinate frame of the positive (a) and negative (b) C-plate. The axes OA and OB located in a xy plane are equivalent.

If a plate is defined by Euler angle θ=π/2 and $\in_A = \in_B \neq \in_C$ then it is called an "A-plate". In this case the principal C-axis lies in the plane of the plate (xy-plane), while the A-axis is normal to the plane surface (due to the uniaxial degeneration the orthogonal orientations of A and B-axes can be chosen arbitrary in the plane that is normal to the xy-surface). In a case of $\in_A = \in_B < \in_C$ the plate is called "positive A-plate". Contrary, if $\in_A = \in_B > \in_C$ the plate is defined as the "negative A-plate" (FIG. 4).

Generally when the permittivity tensor components ($\in_A$, $\in_B$, and $\in_C$) are complex values, the principal permittivity tensor components ($\in_A$, $\in_B$, and $\in_C$), the refraction indices (na, nb, and nc), and the absorption coefficients (ka, kb, and kc) meet the following conditions: $na = Re[(\in_A)^{1/2}]$, $nb = Re[(\in_B)^{1/2}]$, $nc = Re[(\in_C)^{1/2}]$, $ka = Im[(\in_A)^{1/2}]$, $kb = Im[(\in_B)^{1/2}]$, $kc = Im[(\in_C)^{1/2}]$. The smaller a refraction index of an environment, the greater the speed of an electromagnetic wave in this environment. Therefore speed of an electromagnetic wave is an anisotropic value in the anisotropic environment. In plane of the layer there is a fast principal axis directed along the greatest speed of an electromagnetic wave, and there is a slow principal axis directed along the lowest speed of an electromagnetic wave. Thus the retardation layer may be characterized by two in-plane refractive indices corresponding to a fast principal axis and a slow principal axis (nf and ns), and by one refractive index (nn) in the normal direction. In case of a biaxial plate all refractive indices nf, ns and nn have different values. As it has been marked above, the A- and C-plates are assigned to uniaxial plates. In a negative A-plate the refractive indices obey the following condition: nn=ns>nf. The A-plate may be characterized by the retardation parameter $R_A = d \cdot (ns - nf)$, where d is a thickness of this plate. In a negative C-plate the refractive indices obey the following condition: nf=ns>nn. The C-plate may be characterized by the retardation parameter $R_C = d \cdot |ns - nn| = d \cdot |nf - nn|$, where d is a thickness of this plate.

It should be noted that there are quasi A- and quasi C-plates. The negative quasi A-plate is a slightly biaxial plate which is characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1. The negative quasi C-plate is slightly biaxial plate which is characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1.

In a first aspect, the present invention provides a liquid crystal display comprising a vertical alignment mode liquid crystal cell, two polarizers arranged on each side of the liquid crystal cell, and at least one compensating structure located between the liquid crystal cell and one of said polarizers. The polarizers have transmission axes which are perpendicular to each other. Said compensating structure comprises at least one retardation layer comprising supramolecules comprising at least one polycyclic organic compound with a conjugated π-system and functional groups which are capable of forming non-covalent bonds between said supramolecules.

The general description of the present invention having been made, a further understanding can be obtained by reference to the specific preferred embodiments, which are given herein only for the purpose of illustration and are not intended to limit the scope of the appended claims.

In one embodiment of the liquid crystal display, the organic compound has the general structural formula I

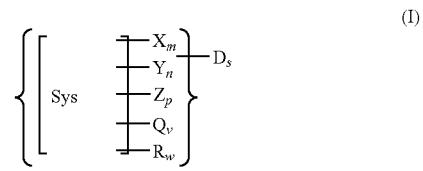

where Sys is an at least partially conjugated substantially planar polycyclic molecular system; X is a carboxylic group —COOH; m is 0, 1, 2, 3 or 4; Y is a sulfonic group —$SO_3H$; n is 0, 1, 2, 3 or 4; Z is a carboxamide group; p is 0, 1, 2, 3 or 4; Q is a sulfonamide group; v is 0, 1, 2, 3 or 4; D is a counterion; s is the number of counterions providing the neutral state of the molecule; R is a substituent selected from the list comprising $CH_3$, $C_2H_5$, Cl, Br, $NO_2$, F, $CF_3$, CN, OH, $OCH_3$, $OC_2H_5$, $OCOCH_3$, OCN, SCN, $NH_2$, and $NHCOCH_3$; w is 0, 1, 2, 3 or 4. Preferably, D is selected from the list comprising the following ions: $H^+$, $NH_4^+$, $Na^+$, $K^+$, $Li^+$, $Ba^{++}$, $Ca^{++}$, $Mg^{++}$, $Sr^{++}$, $Cs^+$, $Pb^{++}$, and $Zn^{++}$. The polyvalent counterions (cations) may be used for stabilization of the organic compounds and provide their insolubility.

In one embodiment of the liquid crystal display, Sys is substantially transparent in the visible spectral range. In the present invention it is supposed that the visible range has a lower boundary that is approximately equal to 400 nm, and an upper boundary that is approximately equal to 700 nm. In another embodiment of the liquid crystal display, Sys has the general structural formulas corresponding to structures II-XLIX given in Table 1:

TABLE 1
Examples of at least partially conjugated substantially planar polycyclic molecular systems (Sys) which are substantially transparent in the visible spectral range
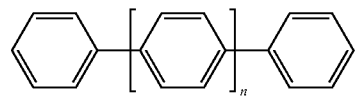  (II)
where n is the number in the range from 1 to 8
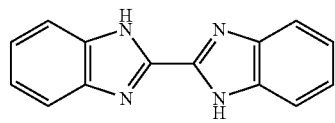  (III)
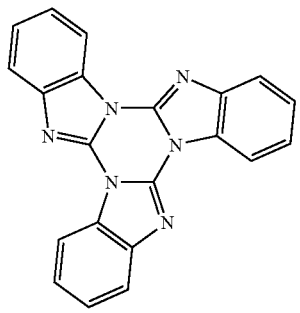  (IV)
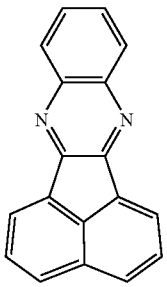  (V)
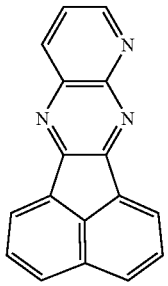  (VI)
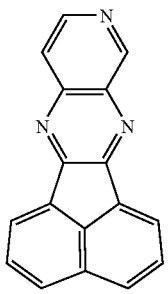  (VII)

TABLE 1-continued
Examples of at least partially conjugated substantially planar polycyclic molecular systems (Sys) which are substantially transparent in the visible spectral range
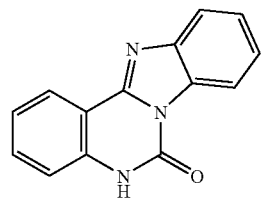
(VIII)
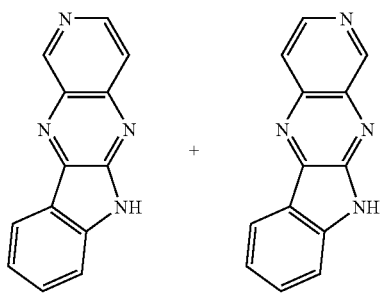
(IX)
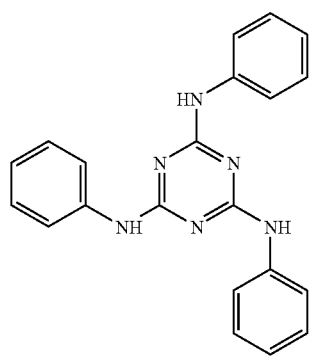
(X)
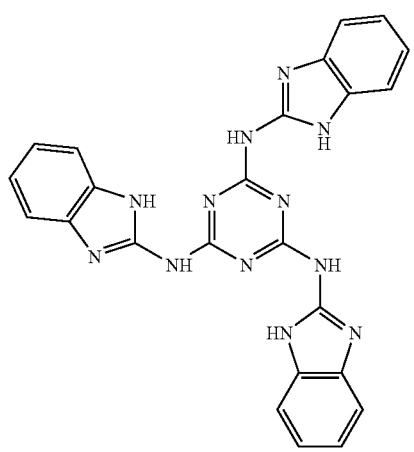
(XI)
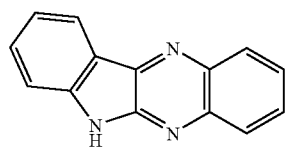
(XII)

TABLE 1-continued
Examples of at least partially conjugated substantially planar polycyclic molecular systems (Sys) which are substantially transparent in the visible spectral range
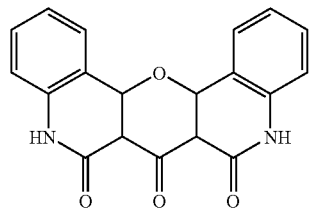 (XIII)
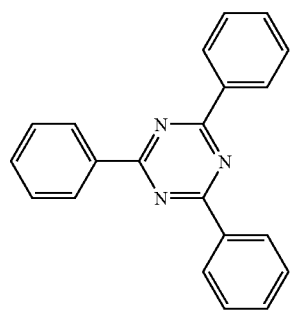 (XIV)
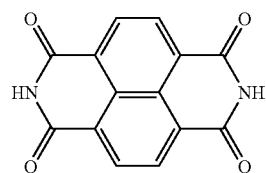 (XV)
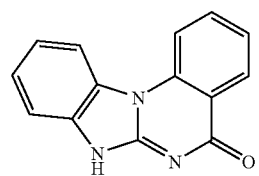 (XVI)
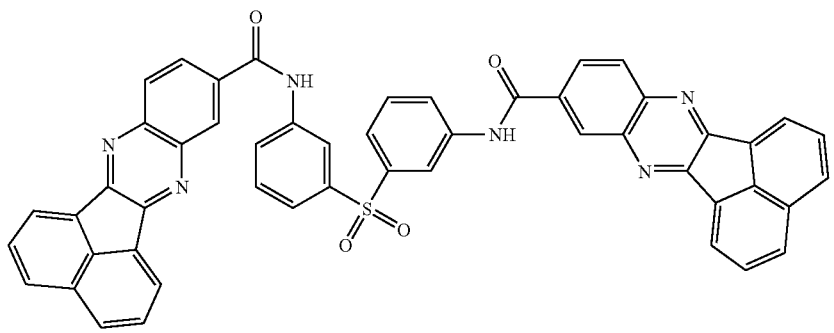 (XVII)
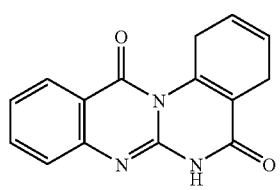 (XVIII)

TABLE 1-continued
Examples of at least partially conjugated substantially planar polycyclic molecular systems (Sys)
which are substantially transparent in the visible spectral range
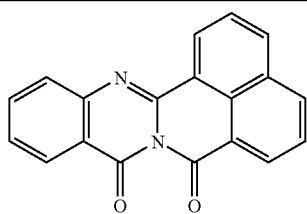
(XIX)
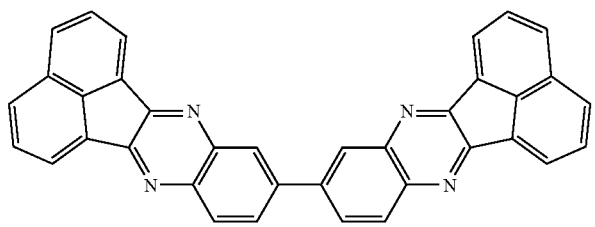
(XX)
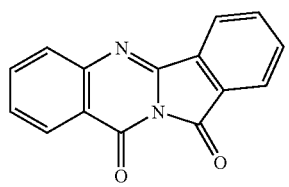
(XXI)
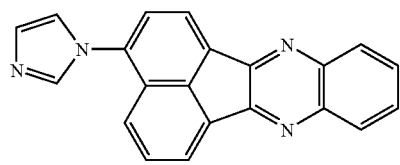
(XXII)
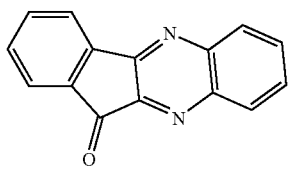
(XXIII)
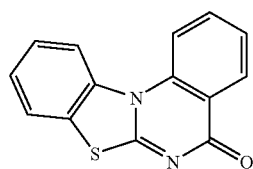
(XXIV)
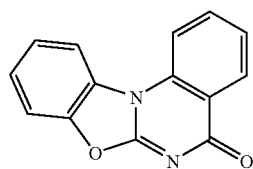
(XXV)
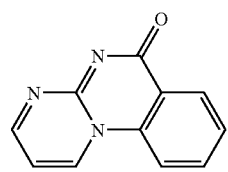
(XXVI)

TABLE 1-continued
Examples of at least partially conjugated substantially planar polycyclic molecular systems (Sys) which are substantially transparent in the visible spectral range
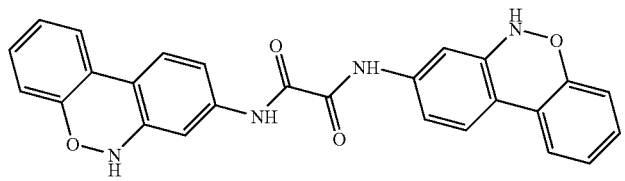 (XXVII)
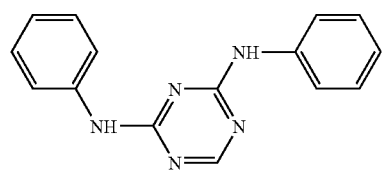 (XXVIII)
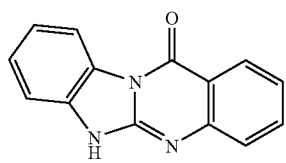 (XXIX)
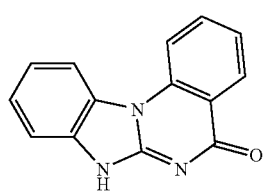 (XXX)
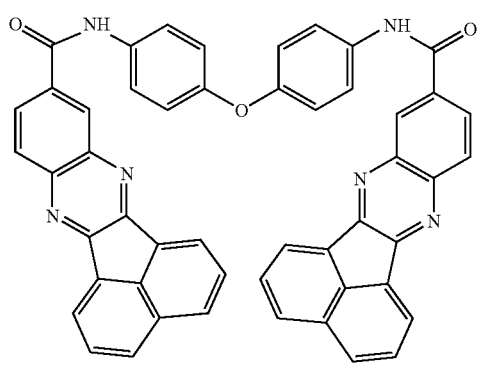 (XXXI)
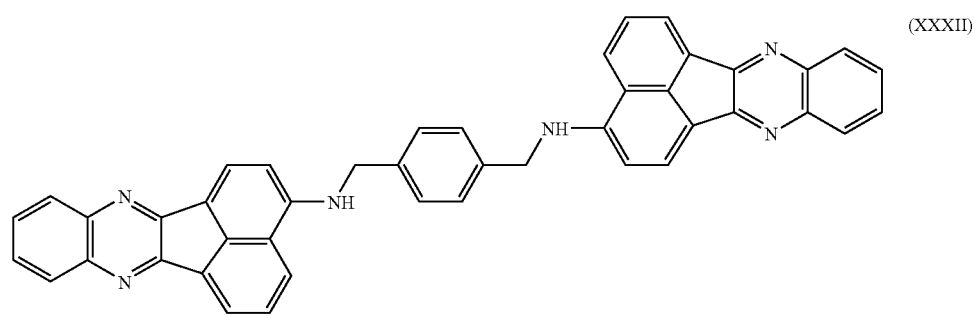 (XXXII)

TABLE 1-continued
Examples of at least partially conjugated substantially planar polycyclic molecular systems (Sys) which are substantially transparent in the visible spectral range
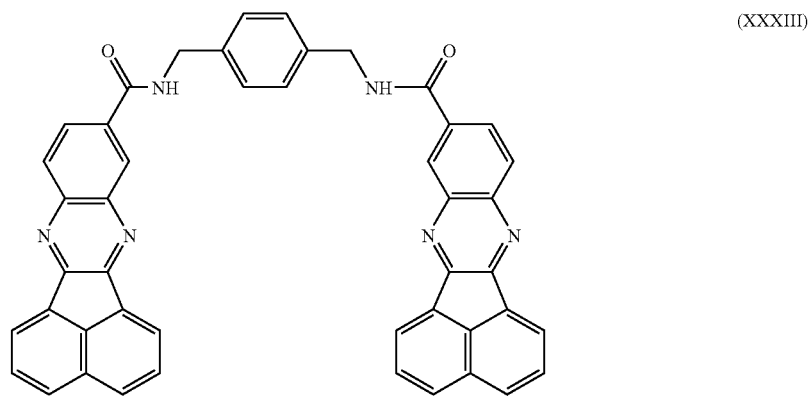
(XXXIII)
(XXXIV)
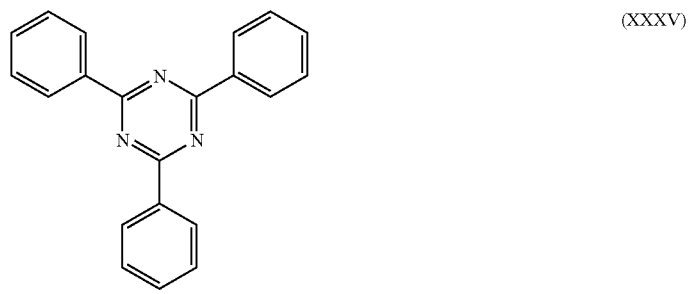
(XXXV)
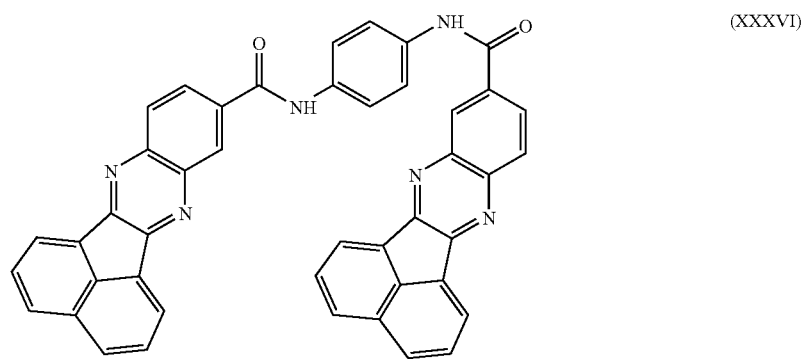
(XXXVI)

TABLE 1-continued
Examples of at least partially conjugated substantially planar polycyclic molecular systems (Sys) which are substantially transparent in the visible spectral range
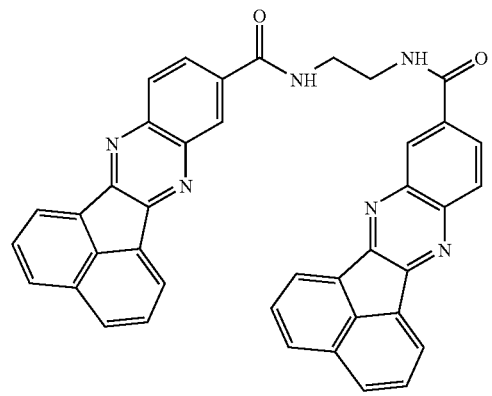
(XXXVII)
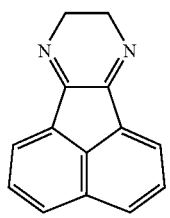
(XXXVIII)
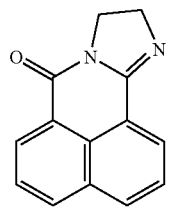
(XXXIX)
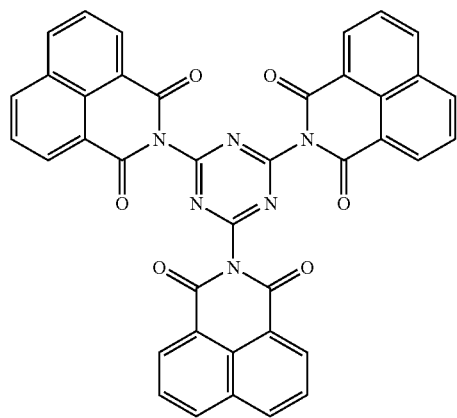
(XL)

TABLE 1-continued
Examples of at least partially conjugated substantially planar polycyclic molecular systems (Sys)
which are substantially transparent in the visible spectral range
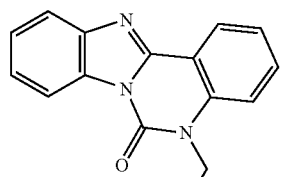
(XLI)
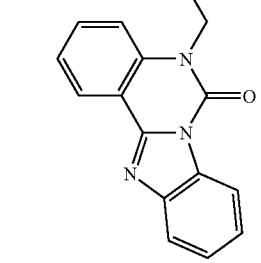
(XLII)
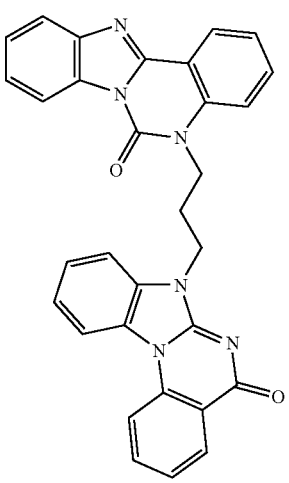
(XLIII)
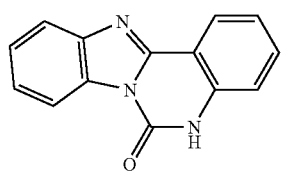
(XLIV)
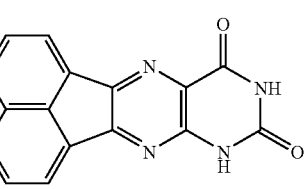
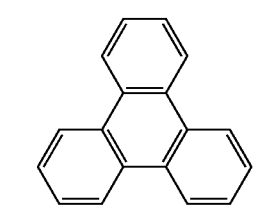
(XLV)

TABLE 1-continued

Examples of at least partially conjugated substantially planar polycyclic molecular systems (Sys) which are substantially transparent in the visible spectral range

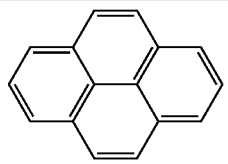
(XLVI)

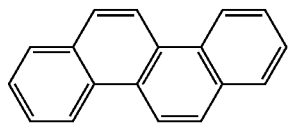
(XLVII)

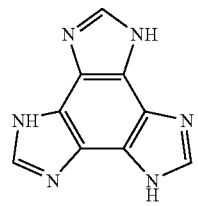
(XLVIII)

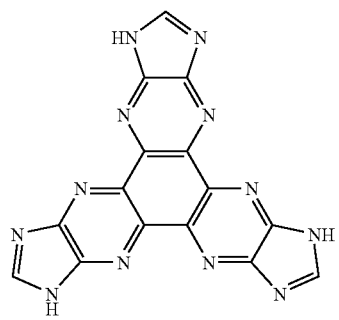
(XLIX)

In one preferred embodiment of the disclosed liquid crystal display, the organic compound is an oligophenyl derivative. Examples of the oligophenyl derivative having general structural formulas corresponding to structures 1-7 are given in Table 2.

TABLE 2

Examples of the oligophenyl derivatives

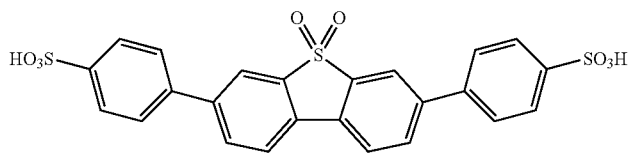
(1)

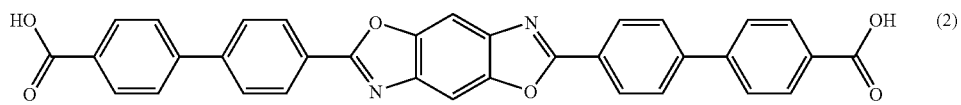
(2)

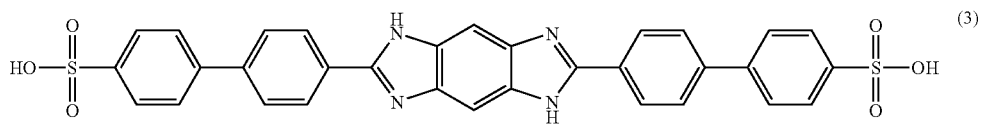
(3)

TABLE 2-continued

Examples of the oligophenyl derivatives (4) [Structure: HO-SO2-phenyl-phenyl-pyridine-phenyl-phenyl-SO2-OH]

(5) [Structure: HO-SO2-phenyl-phenyl-pyrazine-phenyl-phenyl-SO2-OH]

(6) [Structure: HOOC-phenyl-phenyl-pyrimidine-phenyl-phenyl-COOH]

(7) [Structure: HO-SO2-phenyl-phenyl-oxadiazole-phenyl-phenyl-SO2-OH]

In another preferred embodiment of the disclosed liquid crystal display, the organic compound is a bibenzimidazole derivative. Examples of the bibenzimidazole derivative having general structural formulas corresponding to structures 8-9 are given in Table 3.

TABLE 3

Examples of the bibenzimidazole derivatives (8) [Structure: HOOC-benzimidazole-benzimidazole-COOH]

(9) [Structure: HO-SO2-benzimidazole-benzimidazole-SO2-OH]

In still another preferred embodiment of the disclosed liquid crystal display, the organic compound is a "triazine" derivative. Examples of the "triazine" derivatives having general structural formulas corresponding to structures 10-12 are given in Table 4.

TABLE 4

Examples of the "triazine" derivatives

(10) [Tris-benzimidazole triazine structure with three COOH groups]

(11) [Tris-benzimidazole triazine structure with three COOH groups and N+-R substituents]

$R = CH_3, C_2H_5, C_3H_7, C_4H_9$

TABLE 4-continued

Examples of the "triazine" derivatives

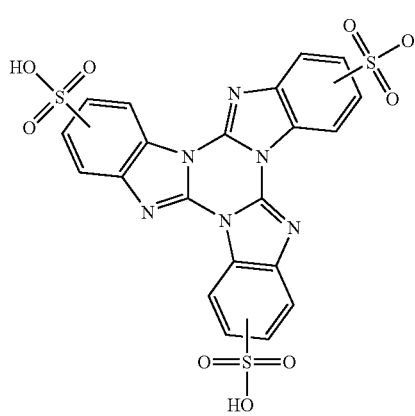
(12)

In one preferred embodiment of the disclosed liquid crystal display, the organic compound is an acenaphthoquinoxaline derivative. Examples of acenaphthoquinoxaline sulfonamide derivatives containing at least one carboxylic group (wherein m is equal to 1, 2, 3 or 4) and having general structural formulas corresponding to structures 13-19 which are given in Table 5.

TABLE 5

Examples of acenaphthoquinoxaline sulfonamide derivatives containing carboxylic groups

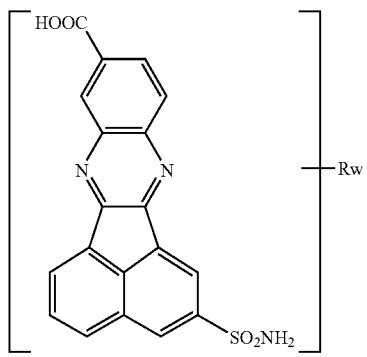
(13)

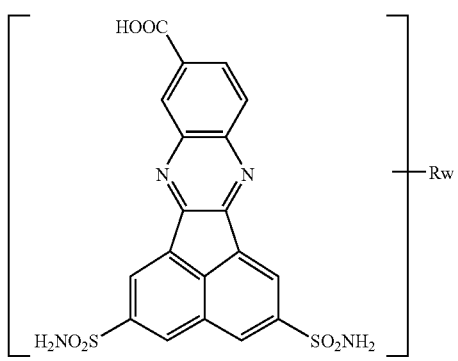
(14)

TABLE 5-continued

Examples of acenaphthoquinoxaline sulfonamide derivatives containing carboxylic groups

(15)

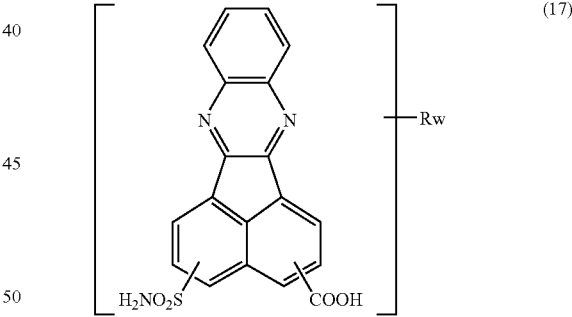
(16)

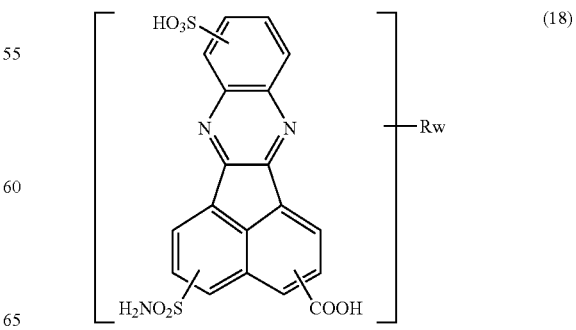
(17)

(18)

TABLE 5-continued

Examples of acenaphthoquinoxaline sulfonamide derivatives containing carboxylic groups

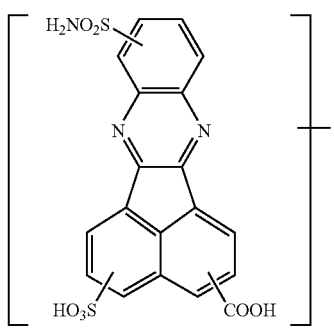
(19)

In another embodiment of the disclosed liquid crystal display the organic compound comprises at least one sulfonic group, wherein n is equal to 1, 2, 3 or 4. Examples of the acenaphthoquinoxaline sulfonamide derivative containing at least one sulfonic group and having general structural formulas corresponding to structures 20-31 are given in Table 6.

TABLE 6

Examples of acenaphthoquinoxaline sulfonamide derivatives containing sulfonic groups

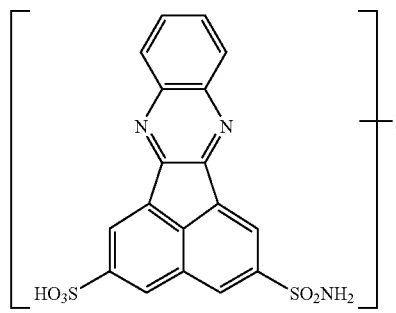
(20)

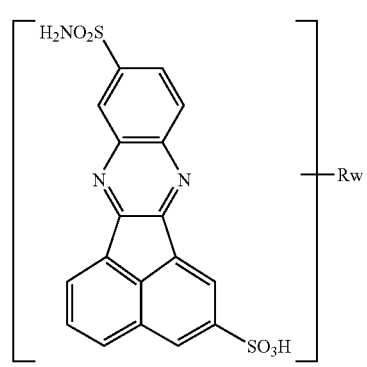
(21)

TABLE 6-continued

Examples of acenaphthoquinoxaline sulfonamide derivatives containing sulfonic groups

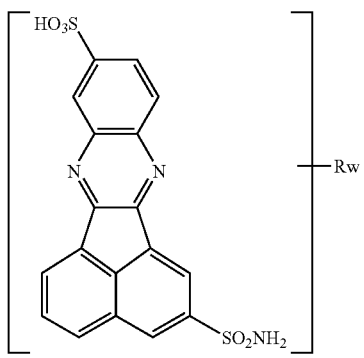
(22)

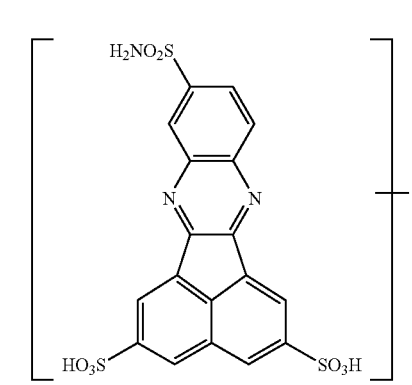
(23)

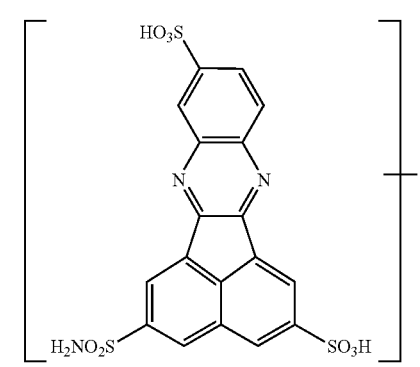
(24)

(25)

TABLE 6-continued

Examples of acenaphthoquinoxaline sulfonamide derivatives containing sulfonic groups

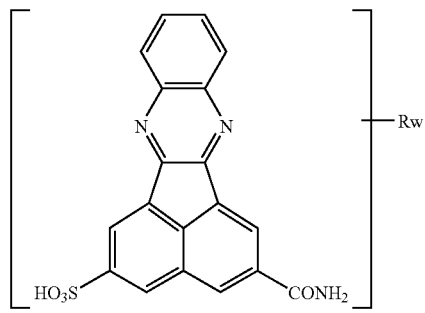
(26)

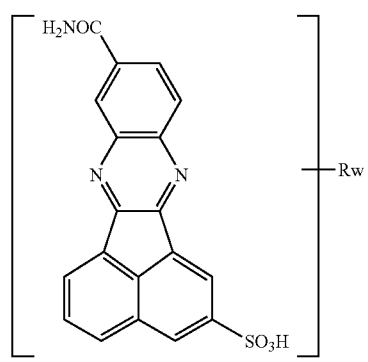
(27)

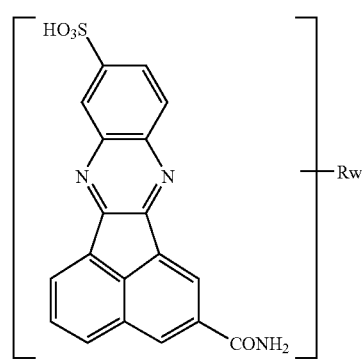
(28)

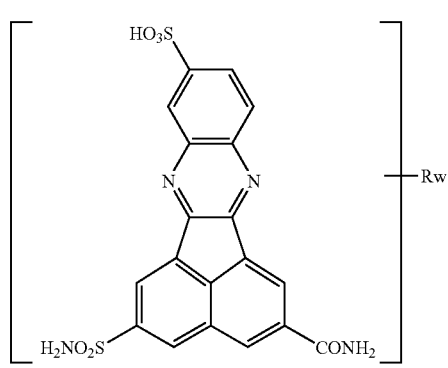
(29)

TABLE 6-continued

Examples of acenaphthoquinoxaline sulfonamide derivatives containing sulfonic groups

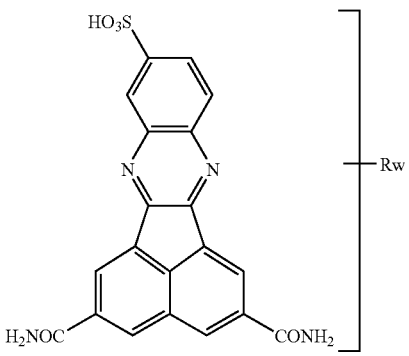
(30)

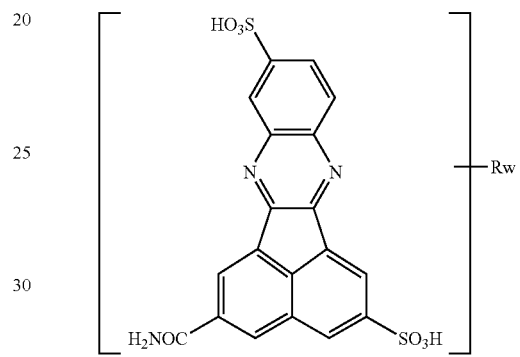
(31)

In another preferred embodiment of the liquid crystal display, the organic compound is a 6,7-dihydrobenzimidazo[1,2-c]quinazolin-6-one derivative having at least one carboxylic group or at least one acid amide group as the functional group.

In one preferred embodiment of the liquid crystal display, the 6,7-dihydrobenzimidazo[1,2-c]quinazolin-6-one derivative has at least one carboxyamide group ($CONH_2$) as the acid amide group. In another preferred embodiment of the disclosed liquid crystal display, the 6,7-dihydrobenzimidazo[1,2-c]quinazolin-6-one derivative has at least one sulfonamide group ($SO_2NH_2$) as the acid amide group. Examples of 6,7-dihydrobenzimidazo[1,2-c]quinazolin-6-one derivatives comprising at least one carboxylic group —COOH, wherein m is 1, 2 or 3 and said derivative has general structural formula from the group comprising structures 32 to 44, are given in Table 7.

TABLE 7

Examples of 6,7-dihydrobenzimidazo[1,2-c]quinazolin-6-one derivatives containing carboxylic groups

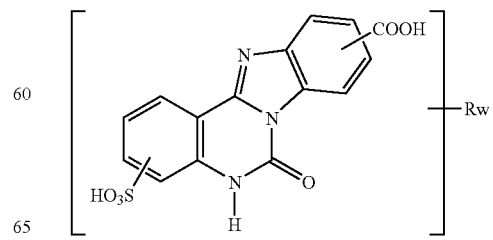
(32)

TABLE 7-continued
Examples of 6,7-dihydrobenzimidazo[1,2-c]quinazolin-6-one derivatives containing carboxylic groups
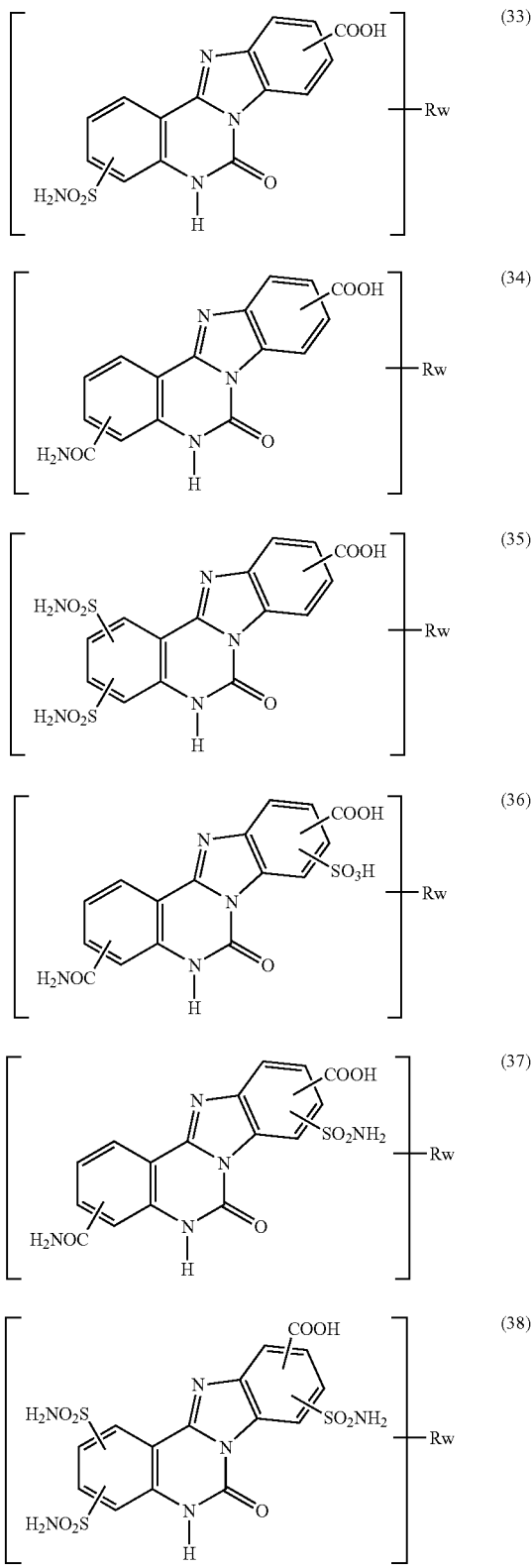
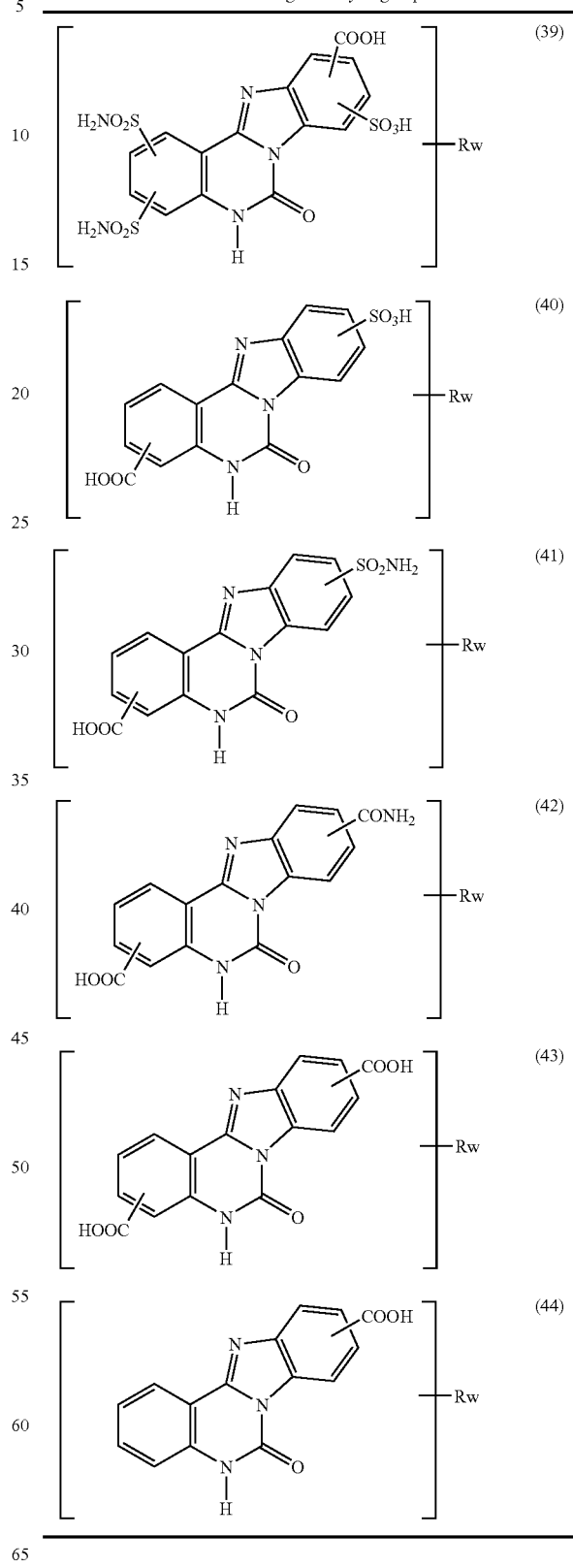
In another preferred embodiment of the liquid crystal display, the 6,7-dihydrobenzimidazo[1,2-c]quinazolin-6-one derivative comprises at least one sulfonic group —SO₃H. Examples of the 6,7-dihydrobenzimidazo[1,2-c]quinazolin-6-one derivatives comprising sulfonic groups —SO₃H, wherein n is 1, 2 or 3 and said derivative has the general structural formula from the list comprising structures 45 to 53, are given in Table 8.

TABLE 8

Example of 6,7-dihydrobenzimidazo[1,2-c]quinazolin-6-one derivatives containing sulfonic groups

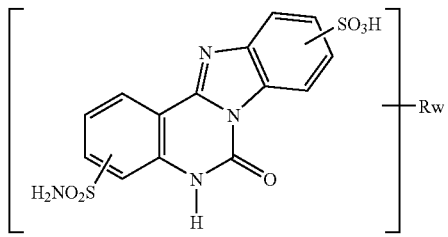
(45)

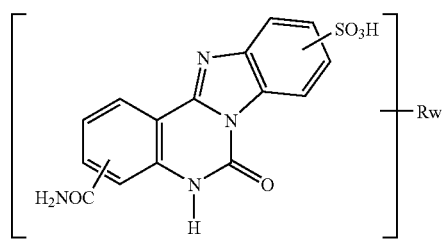
(46)

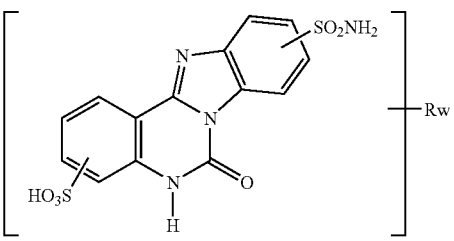
(47)

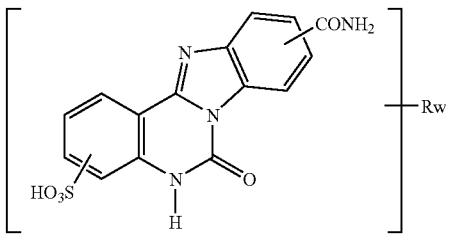
(48)

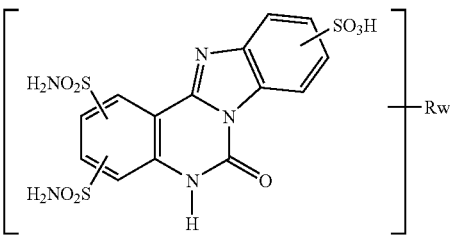
(49)

TABLE 8-continued

Example of 6,7-dihydrobenzimidazo[1,2-c]quinazolin-6-one derivatives containing sulfonic groups

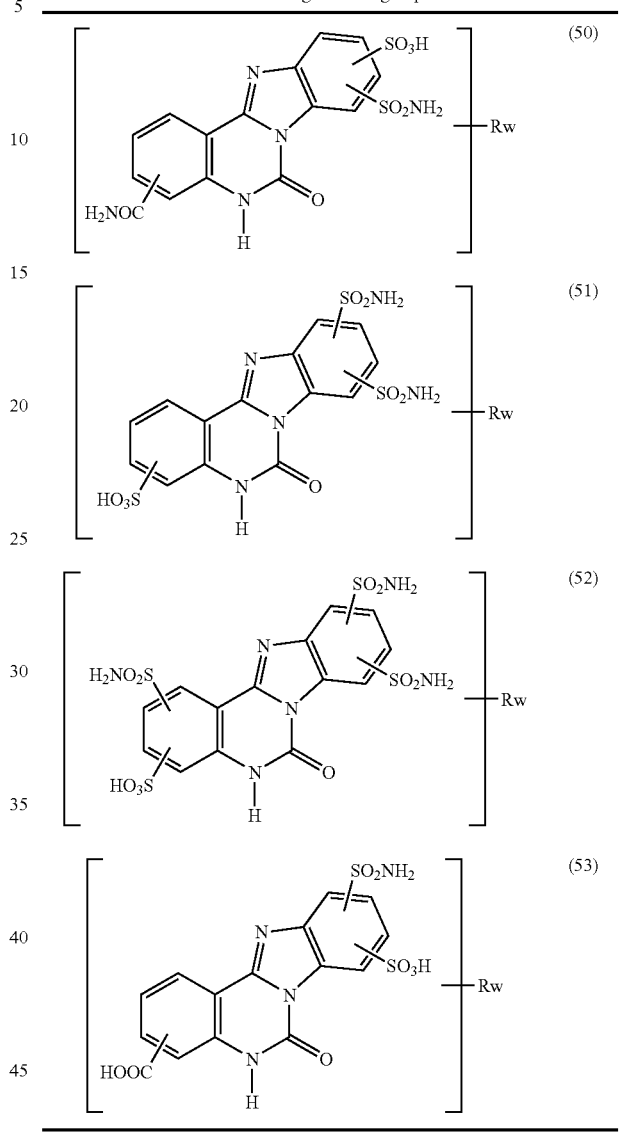

The supramolecule is an association of at least partially planar, more preferably substantially planar, π-conjugated molecules in a stack. The number of molecules in association is preferably defined by conditions of formation such as temperature, pressure, additives and so forth, and not precisely and definitively by the molecules' structure or the composition of functional groups.

In a preferred embodiment of the present invention, the supramolecules comprise at least one polycyclic organic compound with a conjugated π-system and functional groups which are capable of forming non-covalent bonds between said supramolecules. Functional groups of one molecule are preferably designed in such a way that they may interact with each other with formation of inter-stack non-covalent bonding, forming a fully saturated three dimensional network of non-covalent bonds. The retardation layers can be transparent for electromagnetic radiation only in a part of the visible wavelength range, rather than in the entire range, and this part of said wavelength band will be called a subrange. This subrange can be determined experimentally for each polycyclic organic compound with a conjugated π-system and functional groups.

In still another preferred embodiment of the present invention, the molecules of at least one organic compound comprise heterocycles. In yet another preferred embodiment of the present invention, at least one of said retardation layers is water non-soluble.

In another preferred embodiment of the present invention, at least one of said retardation layers is optically biaxial. In another preferred embodiment of the present invention, the supramolecules are oriented substantially parallel or perpendicular to the surface of the retardation layer. In still another preferred embodiment of the present invention, at least one of the non-covalent bonds is an H-bond. In yet another preferred embodiment of the present invention, at least one of the non-covalent bonds is a coordination bond.

In one embodiment of the liquid crystal display the organic compound has the general structural formula I, wherein if m is equal to 0, then both n and p are not equal to 0. In other words in absence of the carboxylic group the organic compound comprises at least one sulfonic group and at least one amide of a carboxylic acid group.

In another embodiment of the liquid crystal display the organic compound has the general structural formula I, wherein if m is equal to 0, then both n and v are not equal to 0. In other words in absence of the carboxylic group the organic compound comprises at least one sulfonic group and at least one amide of a sulfonic acid group.

In still another embodiment of the liquid crystal display the organic compound has the general structural formula I, wherein if n is equal to 0, then m is not equal to 0. In other words in absence of the sulfonic group the organic compound comprises at least one carboxylic group.

In one embodiment of the liquid crystal display, the liquid crystal cell comprises (i) first and second substrates opposing each other and being substantially parallel to each other; (ii) a first electrode provided on a first surface of said first substrate, said first surface facing said second substrate; (iii) a second electrode provided on a second surface of said second substrate, said second surface facing said first substrate; (iv) a first molecular alignment film provided on said first surface of said first substrate so as to cover said first electrode; (v) a second molecular alignment film provided on said second surface of said second substrate so as to cover said second electrode; and (vi) a liquid crystal layer confined between said first and second substrates, said liquid crystal layer containing liquid crystal molecules of a negative dielectric anisotropy.

In one embodiment of the liquid crystal display, the compensating structure comprises at least one retardation layer of a first type having slow and fast principal axes lying substantially in the plane of the first type retardation layer, and at least one retardation layer of a second type having an optical axis directed substantially perpendicular to the plane of the second type retardation layer.

In another embodiment of the liquid crystal display, the retardation layer of the first type is a uniaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: nn=ns>nf. In yet another embodiment of the liquid crystal display, the retardation layer of the first type is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1.

In still another embodiment of the liquid crystal display, the retardation layer of the first type comprises rod-like supramolecules which are oriented with their longitudinal axes substantially parallel to the fast principal axis. In yet another embodiment of the liquid crystal display, said rod-like supramolecules have approximately isotropic polarizability in planes which are perpendicular to their longitudinal axes.

In yet another embodiment of the liquid crystal display, the retardation layer of the first type is a biaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: ns>nn>nf. In still another embodiment of the liquid crystal display, the retardation layer of the first type comprises rod-like supramolecules which are oriented with their longitudinal axes substantially parallel to the fast principal axis, wherein said rod-like supramolecules have anisotropic polarizability in planes which are perpendicular to their longitudinal axes. In yet another embodiment of the liquid crystal display, the retardation layer of the first type is arranged such that the fast axis of said retardation layer is substantially perpendicular to the transmission axis of the adjacent polarizer. In one embodiment of the liquid crystal display, the retardation layer of the first type is arranged such that the fast axis of said retardation layer is substantially parallel to the transmission axis of the adjacent polarizer.

In one embodiment of the liquid crystal display, the retardation layer of the second type is a uniaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: nf=ns>nn. In another embodiment of the liquid crystal display, the retardation layer of the second type is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1.

In one embodiment of the liquid crystal display, the retardation layer of the second type comprises sheet-like supramolecules which are oriented with their plane substantially parallel to the surface of said retardation layer. In another embodiment of the liquid crystal display, the retardation layer of the second type comprises rod-like supramolecules which are oriented with their longitudinal axes substantially perpendicular to the surface of said retardation layer. In still another embodiment of the liquid crystal display, the retardation layer of the second type comprises flat polycyclic organic compounds, which are oriented with their plane substantially parallel to the surface of said retardation layer. In yet another embodiment of the liquid crystal display, the retardation layer of the second type comprises triacetyl cellulose (TAC).

In one embodiment of the liquid crystal display, the compensating structure comprises the retardation layer of the second type located closer to the liquid crystal cell as compared to the retardation layer of the first type. In another embodiment of the liquid crystal display, the compensating structure comprises the retardation layer of the first type located closer to the liquid crystal cell as compared to the retardation layer of the second type. In still another embodiment of the liquid crystal display, said compensating structure comprises first and second retardation layers of second type arranged on each side of one retardation layer of a first type. In another embodiment of the present invention, the liquid crystal display comprises at least two compensating structures each located between the liquid crystal cell and one of said polarizers.

A more complete assessment of the present invention and its advantages will be readily achieved as the same becomes better understood by reference to the following detailed description, considered in connection with the accompanying drawings and detailed specification, all of which forms a part of the disclosure. The subject of the invention is illustrated by the following Figures, of which:

Figure 28:
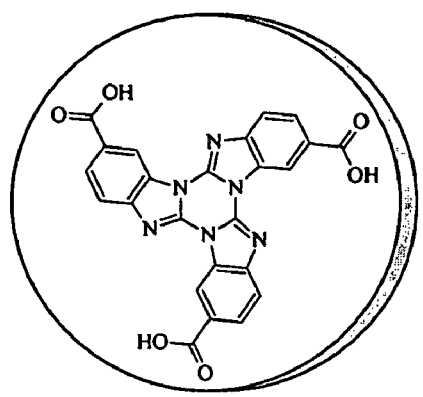

FIG. 28 schematically shows a flat molecule of polycyclic organic compound.

Figure 29:
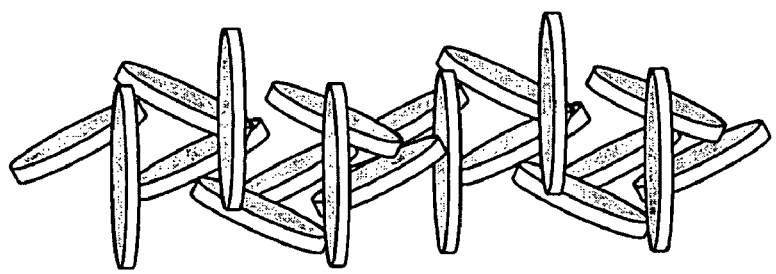

FIG. 29 schematically shows a solution of flat molecules.

Figure 30:
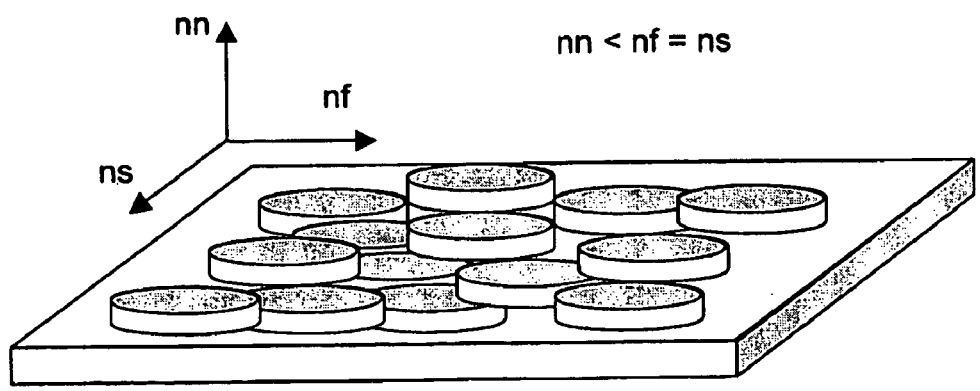

FIG. 30 schematically shows a molecular packing which cause negative C-plate formation.

Figure 31:
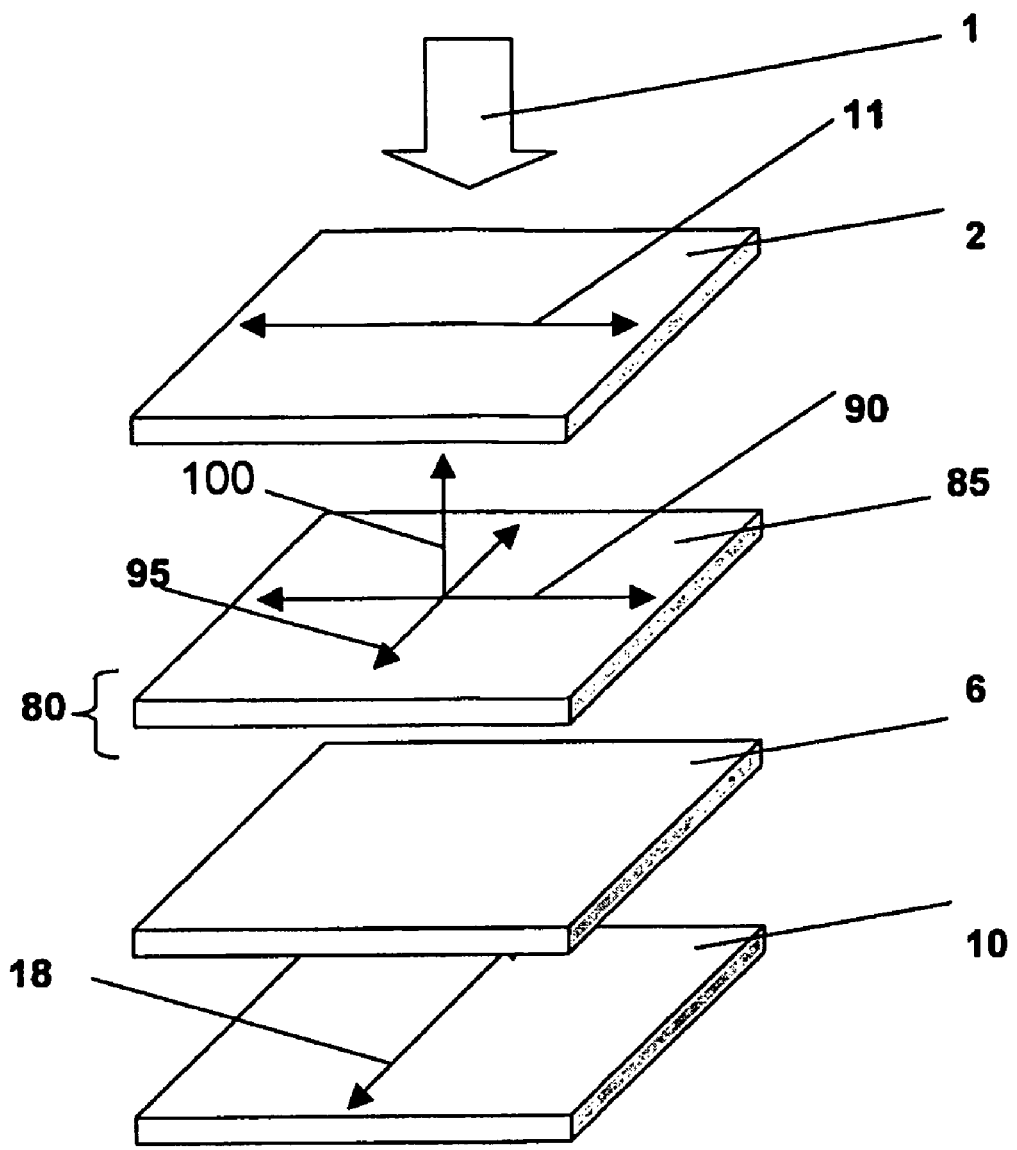

FIG. 31 is a diagram showing a construction of a liquid crystal display according to one embodiment of the present invention.

Figure 32:
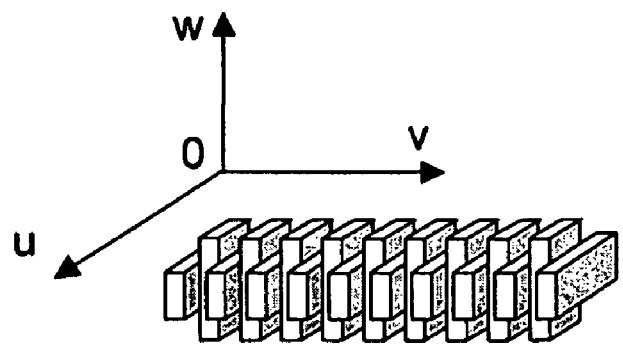

FIG. 32 schematically shows a rod-like supramolecule which solution forms negative A-plate.

Figure 33:
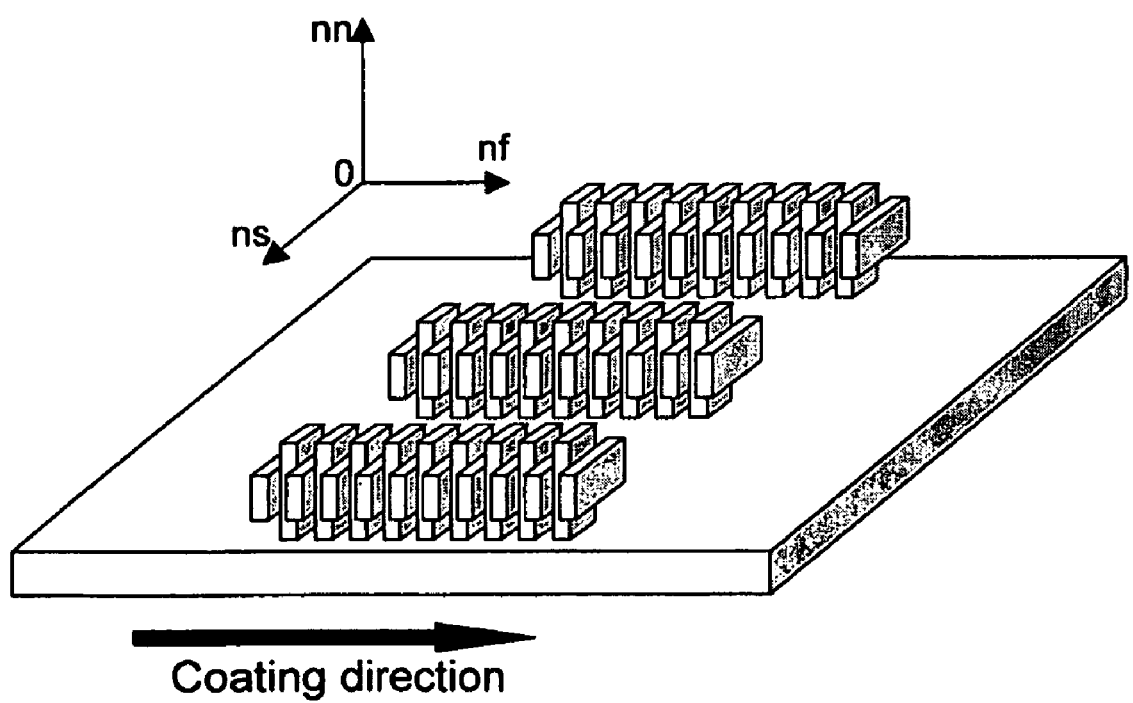

FIG. 33 schematically shows a molecular packing which cause negative A-plate formation.

Figure 34:
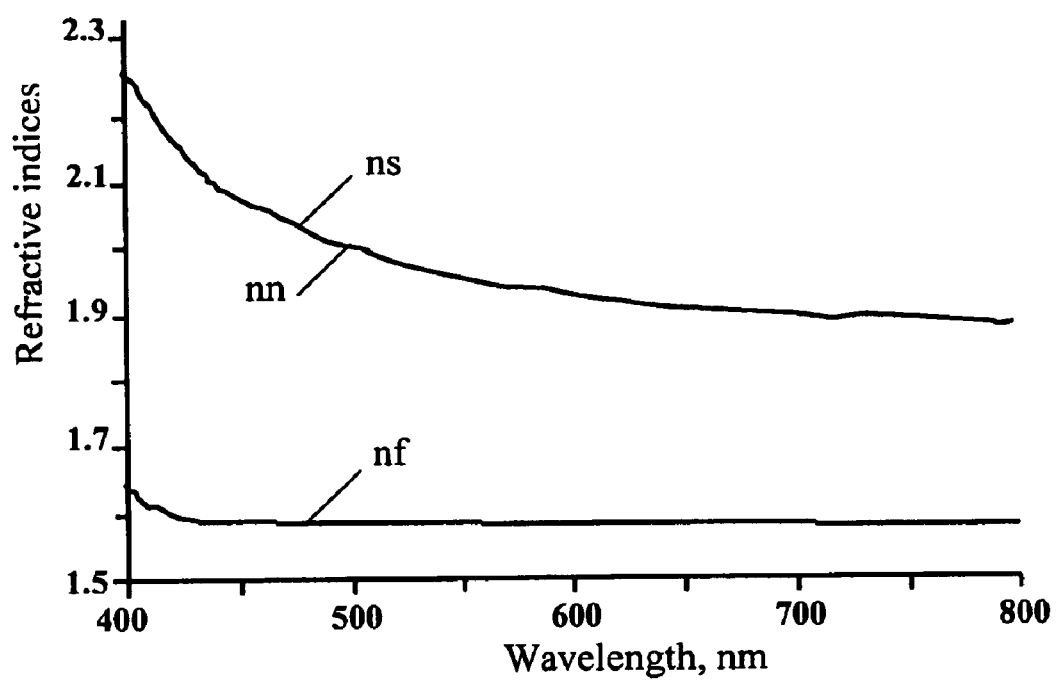

FIG. 34 shows spectral dependencies of the refractive indices of negative A-type retardation layer according to the present invention.

Figure 1:
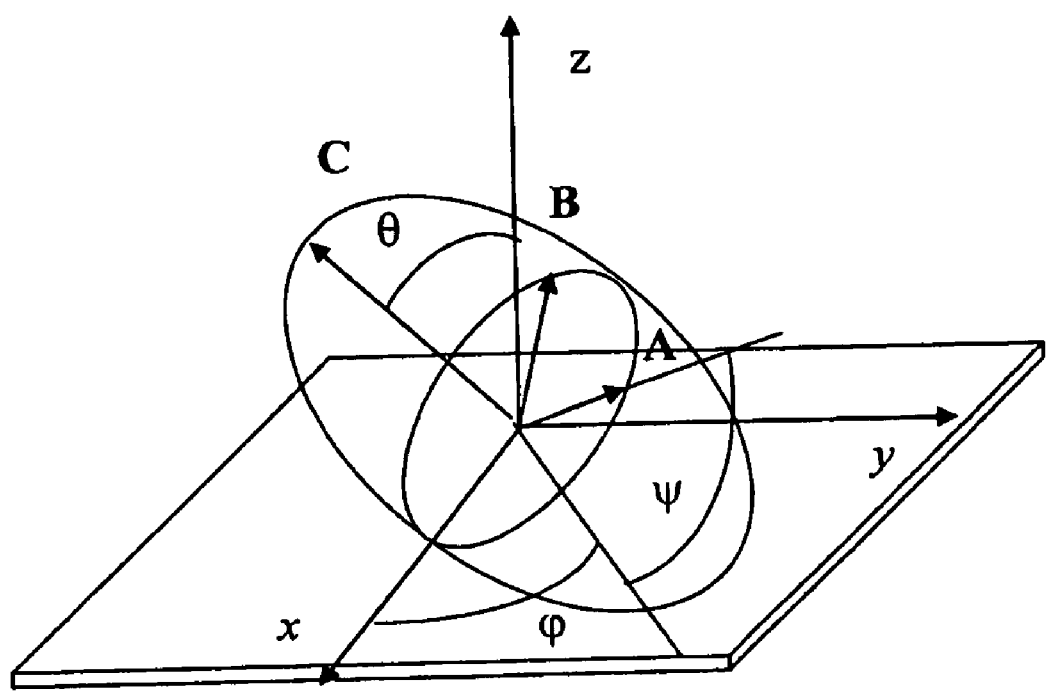
FIG. 1 shows the principal axes (A, B, C) of the dielectric permittivity tensor arbitrarily oriented with respect to the xyz frame associated with a film plane.
Figure 2:
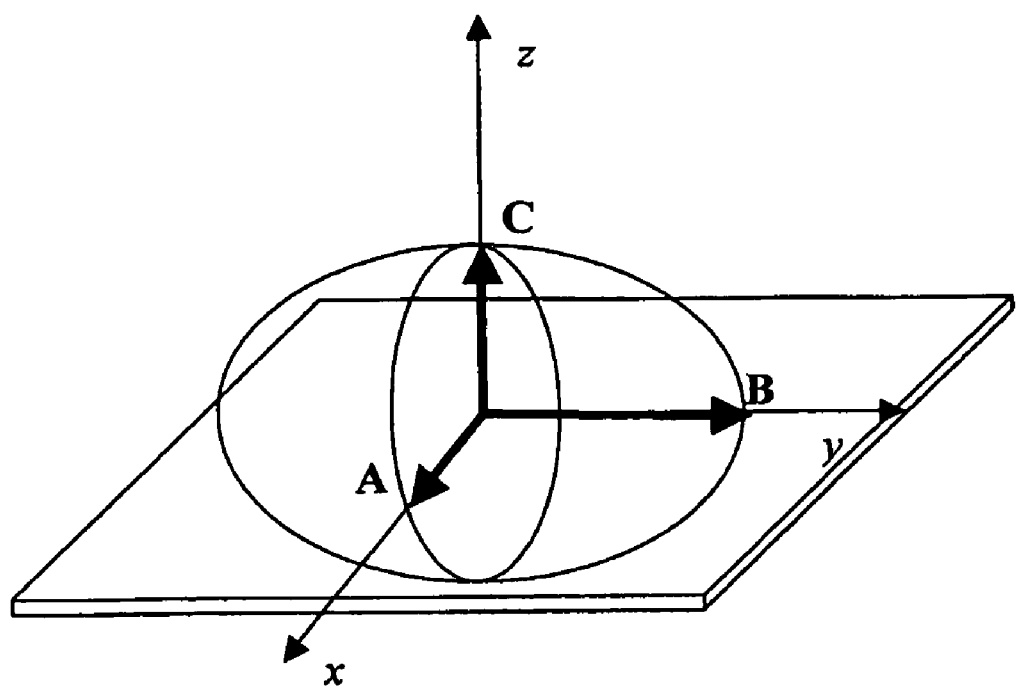
FIG. 2 shows the dielectric permittivity tensor for "$A_B$"-type or "$B_A$"-type plates.
Figure 3A:
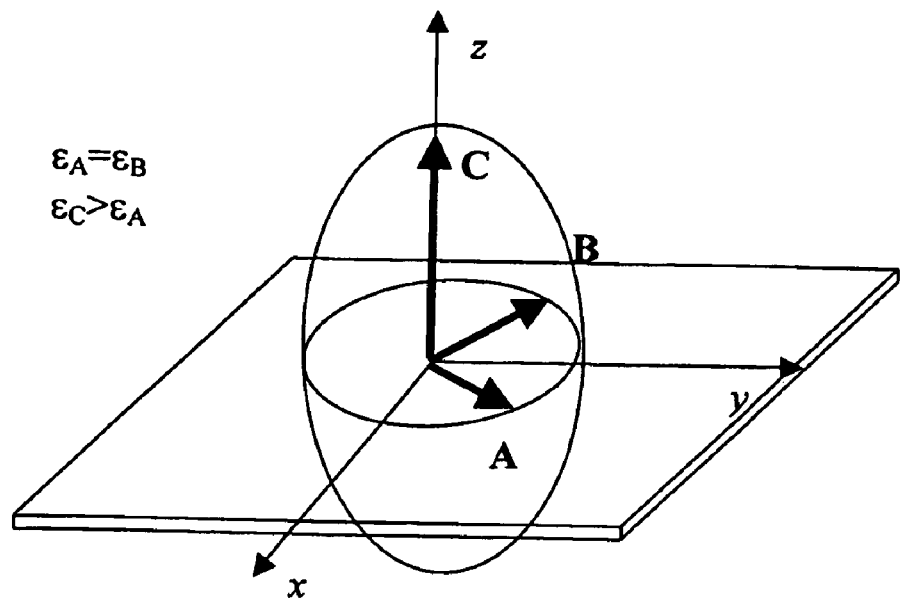
FIG. 3a shows the orientation of the principal axes and relation between the principal components of the dielectric tensor for a positive C-plate.
Figure 3B:
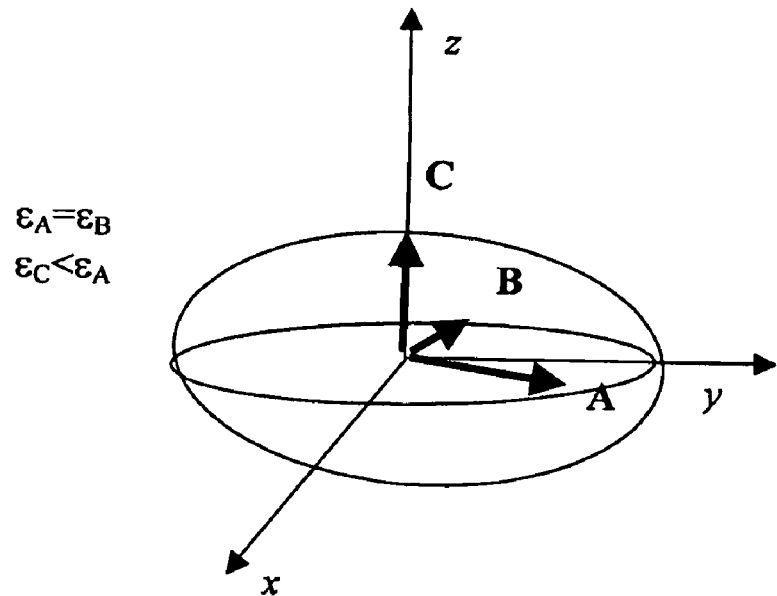
FIG. 3b shows the orientation of the principal axes and relation between the principal components of the dielectric tensor for a negative C-plate.
Figure 4A:
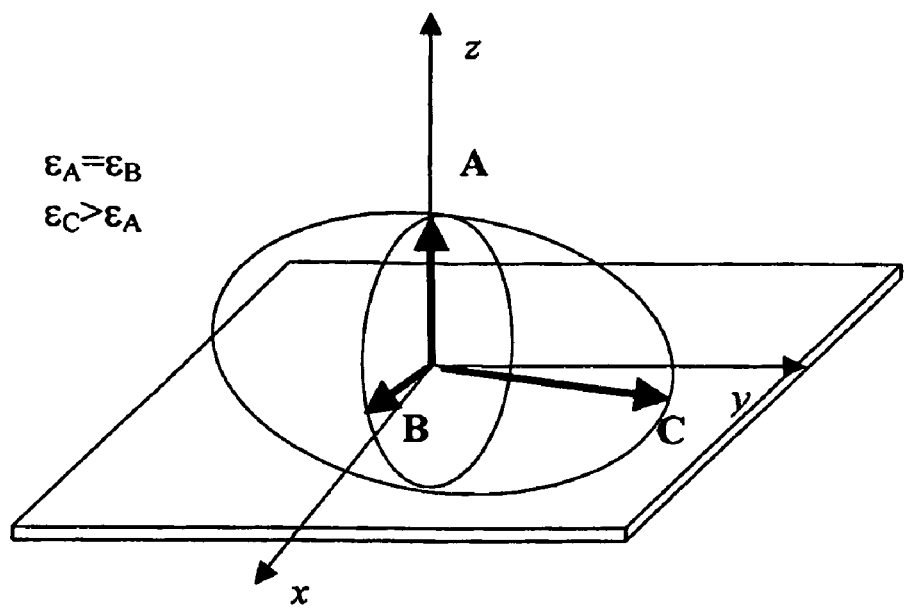
FIG. 4a shows the orientation of the principal axes and relation between the principal components of the dielectric tensor for a positive A-plate.
Figure 4B:
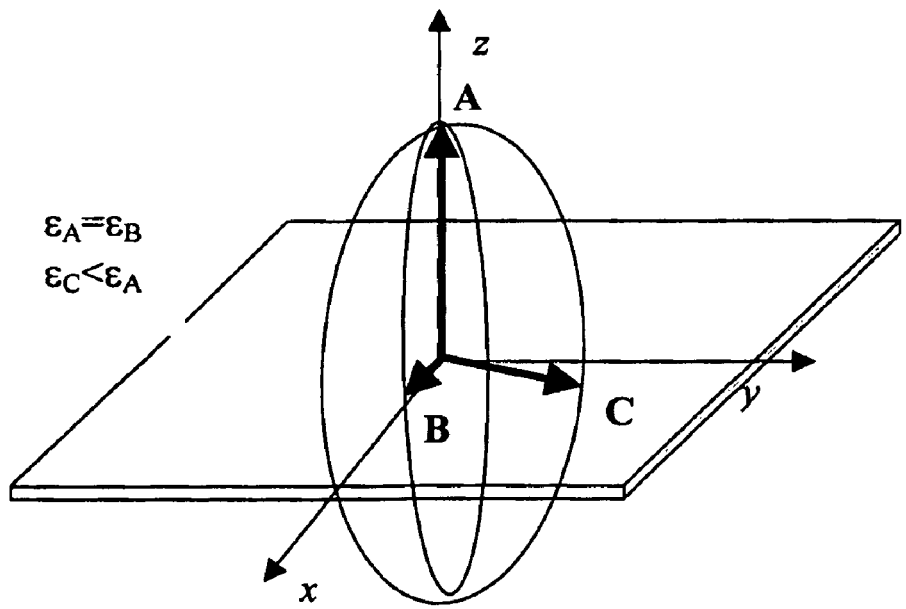
FIG. 4b shows the orientation of the principal axes and relation between the principal components of the dielectric tensor for the case of a negative A-plate.
Figure 5:
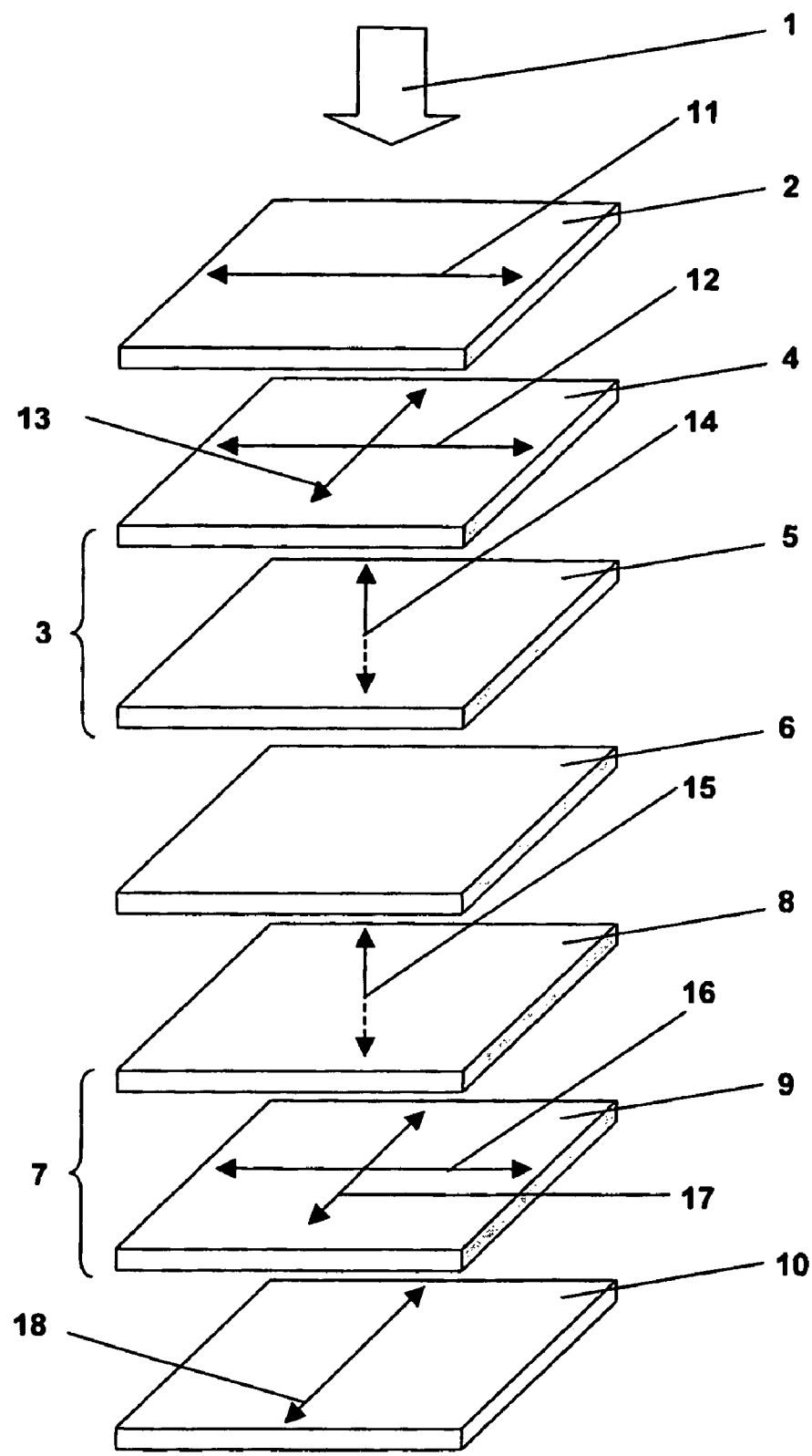
FIG. 5 is a diagram showing a construction of a liquid crystal display according to a first embodiment of the present invention.

FIG. 5 schematically shows a light beam (1) and a liquid crystal display which comprises a liquid crystal cell (6) in a vertical alignment mode, a pair of polarizers (2 and 10) arranged on each side of the liquid crystal cell, and two compensating structures (3 and 7) disposed between the liquid crystal cell and the first polarizer (2), and the liquid crystal cell and the second polarizer (10), respectively. The transmission axis (11) of the first polarizer is perpendicular to the transmission axis (18) of the second polarizer. The first compensating structures (3) comprises a retardation layer of the first type (4) having slow (12) and fast (13) principal axes (the principal axes correspond to the principal axes of the dielectric tensor) lying substantially in the plane of said retardation layer (4), and a retardation layer of the second type (5) as a negative C-plate with the optical axis (14) directed substantially perpendicularly to the plane of said retardation layer (5). The retardation layer (4) is arranged such that the fast principal axis (13), corresponding to lowest dielectric permittivity, of said retardation layer is perpendicular to the transmission axis (11) of the polarizer (2). The retardation layer (4) is a uniaxial retardation layer characterized by layer thickness d, two in-plane principal refractive indices corresponding to a fast principal axis and a slow principal axis (nf and ns) and one refractive index (nn) for the normal direction which obey the following condition for electromagnetic radiation in the visible spectral range: nn=ns>nf.

In another embodiment the retardation layer (4) is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1.

In still another embodiment the retardation layer of a second type (5) is a slightly biaxial retardation layer and it is characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1. The second compensating structure (7) comprises a retardation layer of the first type (9) having slow (17) and fast (16) principal axes lying substantially in the plane of said retardation layer (9), and a retardation layer of the second type (8) as a negative C-plate with the optical axis (15) directed substantially perpendicularly to the plane of said retardation layer (8). The retardation layer of the first type (9) is arranged such that the fast principal axis (16) of said retardation layer is perpendicular to the transmission axis (18) of the polarizer (10). The retardation layer of the first type (9) is an uniaxial retardation layer characterized by layer thickness d, two in-plane refractive indices corresponding to a fast and a slow principal axes (nf and ns) and one refractive index (nn) in the normal direction which obey the following condition for electromagnetic radiation in the visible spectral range: nn=ns>nf.

In another embodiment the retardation layer (9) is a slightly biaxial retardation layer and it is characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1.

In still another embodiment the retardation layer of the second type (8) is a slightly biaxial retardation layer and it is characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1.

Figure 6:
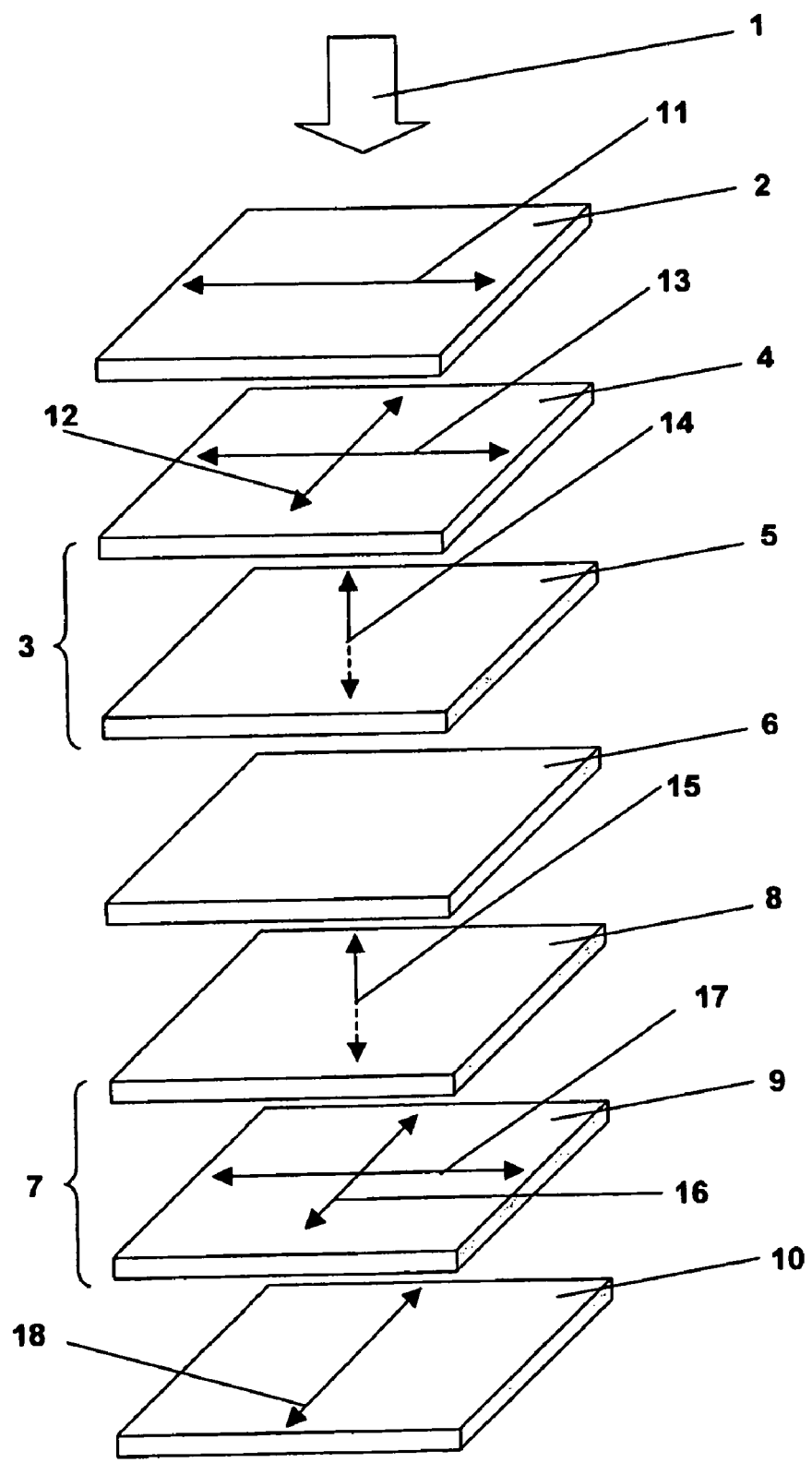
FIG. 6 is a diagram showing a construction of a liquid crystal display according to a second embodiment of the present invention.

FIG. 6 schematically shows a liquid crystal display similar to the display shown in FIG. 5. The difference is in an orientation of principal axes (slow and fast) of the retardation layers of the first type (4 and 9). The retardation layer (4) is arranged such that the slow principal axis (12) of said retardation layer is perpendicular to the transmission axis (11) of the polarizer (2) and the retardation layer of the first type (9) is arranged such that the slow principal axis (17) of said retardation layer is perpendicular to the transmission axis (18) of the polarizer (10). In another embodiment the retardation layers (4 and 9) are slightly biaxial retardation layers being characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1.

Figure 7:
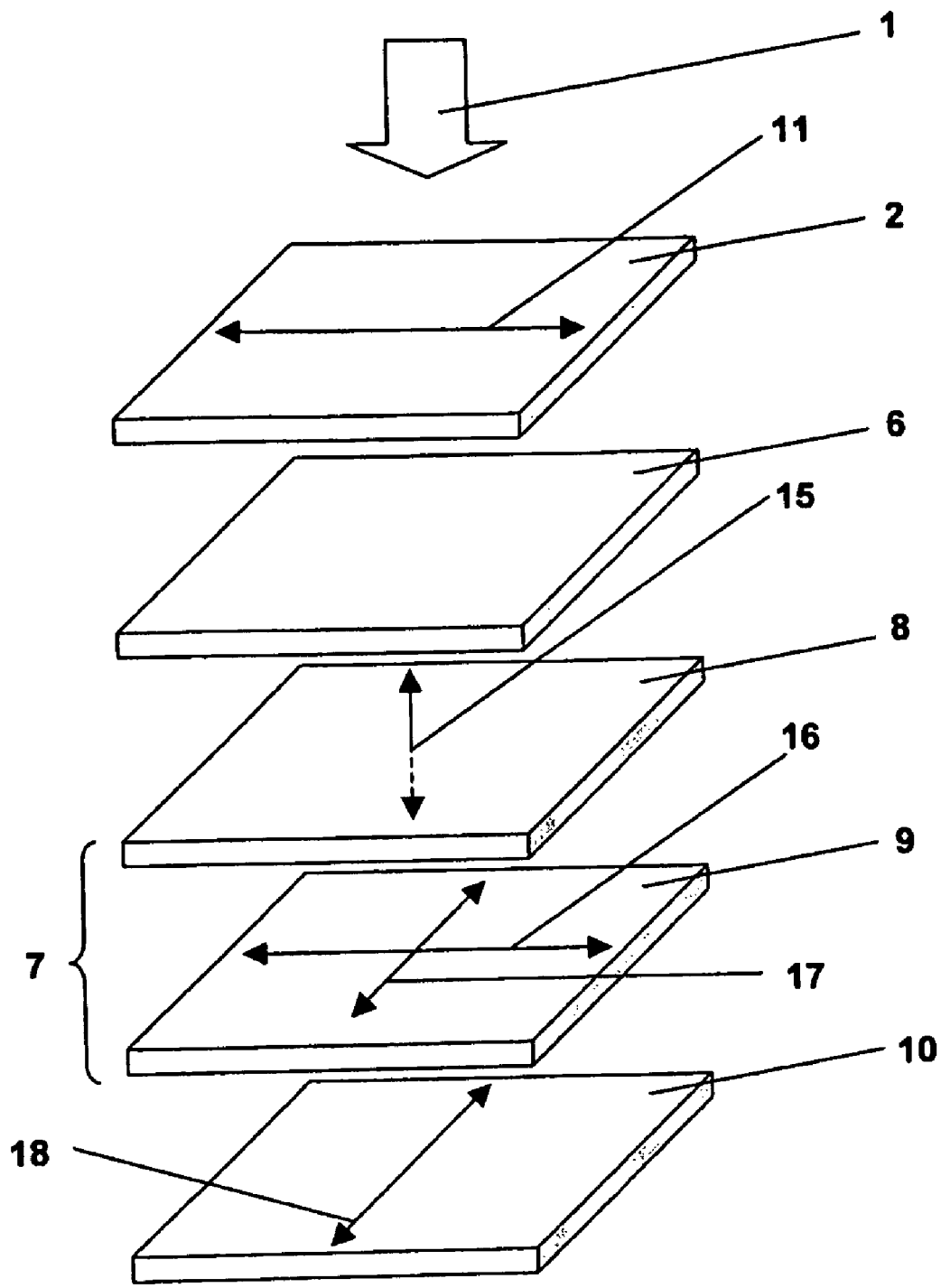
FIG. 7 is a diagram showing a construction of a liquid crystal display according to a third embodiment of the present invention.

FIG. 7 schematically shows a light beam (1) and a liquid crystal display which comprises a liquid crystal cell (6) in a vertical alignment mode, a pair of polarizers (2 and 10) arranged on each side of the liquid crystal cell, and one compensating structure (7) disposed between the liquid crystal cell and the second polarizer (10). The compensating structure (7) comprises a retardation layer of the first type (9) having slow (17) and fast (16) axes lying substantially in the layer plane, and a retardation layer of the second type (8) as a negative C-plate with the optical axis (15) directed substantially perpendicular to the layer plane. The retardation layer (9) is arranged such that the fast principal axis (16) of said retardation layer is perpendicular to the transmission axis (18) of the polarizer (10). The retardation layer (9) is a uniaxial retardation layer characterized by layer thickness d, two in-plane refractive indices corresponding to a fast principal axis and a slow principal axis (nf and ns) and one refractive index (nn) in the normal direction which obey the following condition for electromagnetic radiation in the visible spectral range: nn=ns>nf. In another embodiment the retardation layer (9) is a slightly biaxial retardation layer being characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1. In still another embodiment the retardation layer of a second type (8) is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1.

Figure 8:
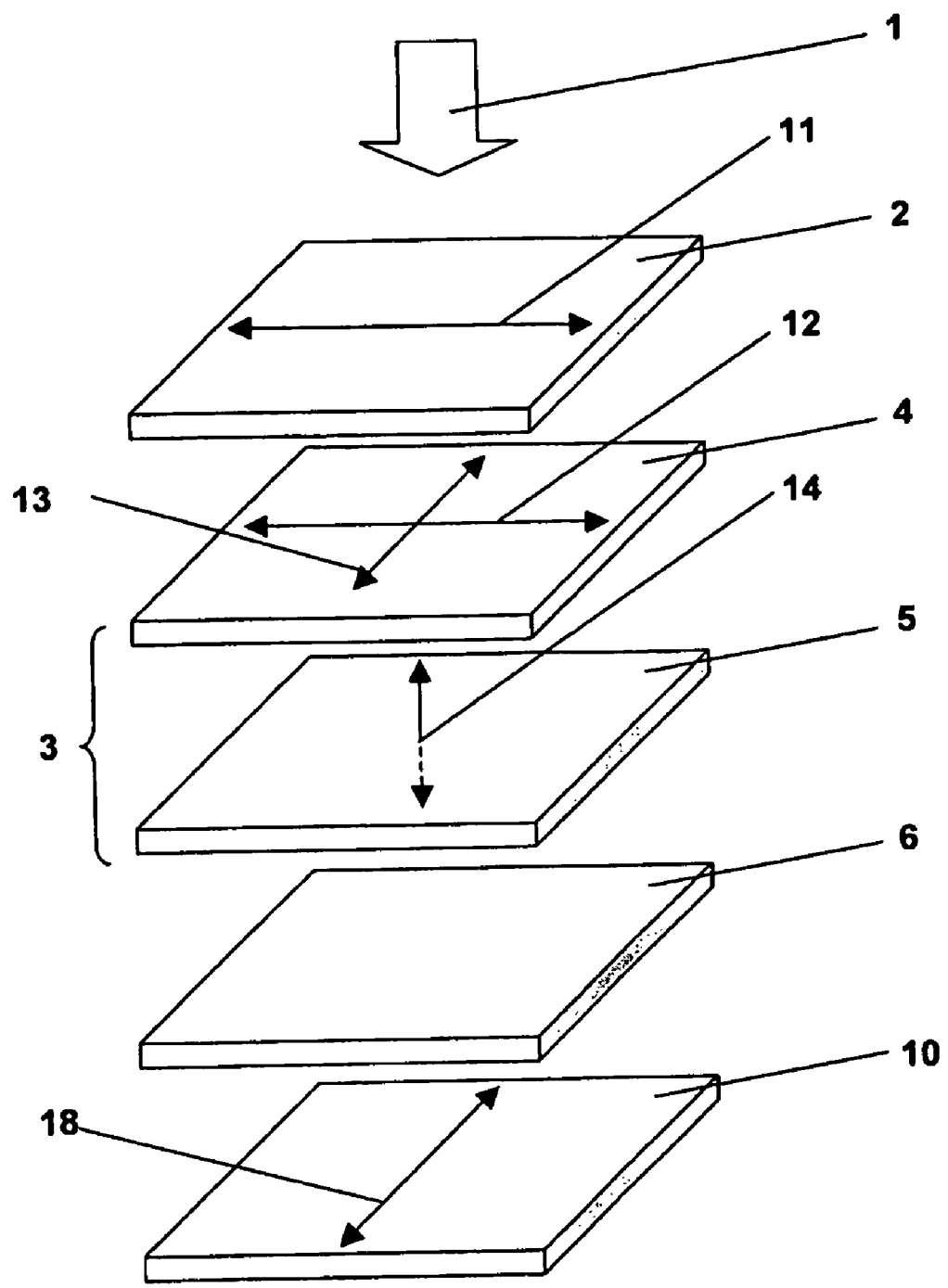
FIG. 8 is a diagram showing a construction of a liquid crystal display according to a fourth embodiment of the present invention.

FIG. 8 schematically shows a light beam (1) and a liquid crystal display which comprises a liquid crystal cell (6) in a vertical alignment mode, a pair of polarizers (2 and 10) arranged on each side of the liquid crystal cell, and one compensating structure (3) disposed between the liquid crystal cell and the first polarizer (2). The transmission axis (11) of the first polarizer is perpendicular to the transmission axis (18) of the second polarizer. The first compensating structure (3) comprises a retardation layer of the first type (4) having slow (12) and fast (13) axes lying substantially in the layer plane, and a retardation layer of the second type (5) as a negative C-plate with the optical axis (14) directed substantially perpendicular to the retardation layer plane. The retardation layer (4) is arranged such that the fast principal axis (13) of said retardation layer is perpendicular to the transmission axis (11) of the polarizer (2). The retardation layer (4) is a uniaxial retardation layer characterized by layer thickness d, two in-plane refractive indices corresponding to a fast principal axis and a slow principal axis (nf and ns) and one refractive index (nn) in the normal direction which obey the following condition for electromagnetic radiation in the visible spectral range: nn=ns>nf. In another embodiment the retardation layer (4) is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1. In still another embodiment the retardation layer of a second type (5) is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1.

In order that the invention may be more readily understood, reference is made to the following examples, which are intended to be illustrative of the invention, but are not intended to be limiting in scope.

EXAMPLE 1

Figure 9:
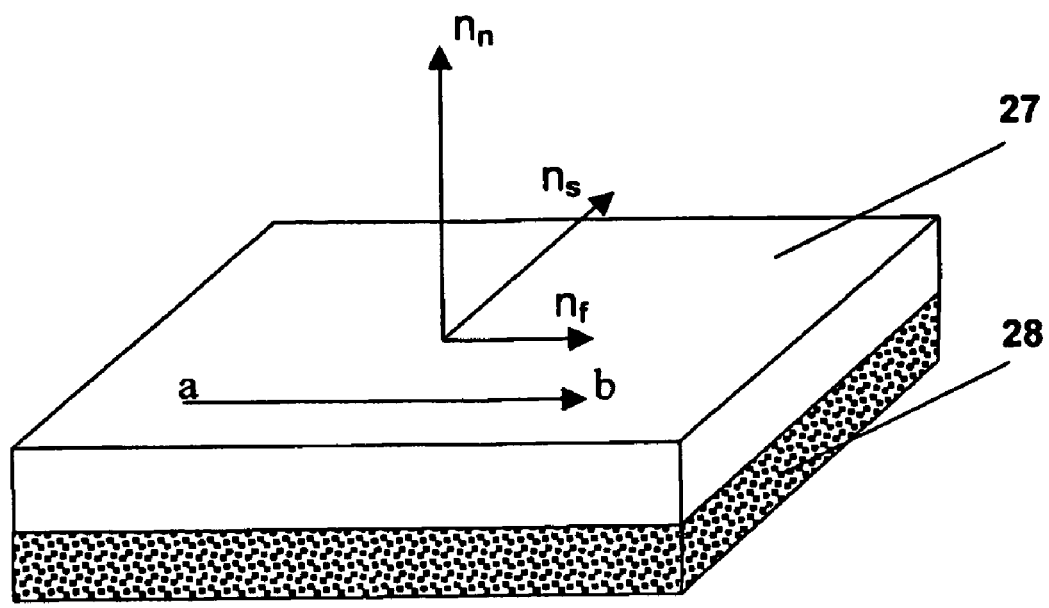
FIG. 9 shows the structure of compensating structures comprising retardation layers of first and second types.

This example describes the preparation of an organic retardation layer (27) as shown in FIG. 9. A mixture of 6-oxo-3-sulfo-5,6-dihydrobenzimidazo[1,2-c]quinazoline-10-carboxylic acid and 6-oxo-3-sulfo-5,6-dihydrobenzimidazo[1,2-c]quinazoline-9-carboxylic acid (1 g) was stirred for 1 h at a temperature of 20° C. in a mixture of 15.0 ml of deionized water with 0.6 ml of a 10% aqueous ammonia solution until a lyotropic liquid crystal solution was formed. The obtained solution was applied at a temperature of 20° C. and a relative humidity of 65% onto the substrate surface with a Mayer rod #2.5 moved at a linear velocity of 15 mm/s along the direction designated as ab in FIG. 9. The substrate (28) was made of triacetyl cellulose (TAC). Then, the organic retardation layer was dried at the same humidity and temperature. In order to determine the optical characteristics of the organic retardation layer, thickness, optical retardation and transmission spectra were measured in a wavelength range from approximately 400 to 700 nm using Dectak³ST, Axometrics and Cary 500 Scan spectrophotometer respectively. The optical transmission of the organic retardation layer was measured using light beams linearly polarized parallel and perpendicular to the coating direction ($T_{par}$ and $T_{per}$, respectively). The obtained data were used to calculate the refractive indices (nf, ns, and nn) shown in FIG. 9. The obtained retardation layer was anisotropic (nf<ns≈nn). The fast principal axis is parallel to the coating direction (ab), and the slow principal axis is perpendicular to the coating direction (ab). The two in-plane refractive indices (nf and ns) and one refractive index (nn) in the normal direction obey the following conditions for electromagnetic radiation in the visible spectral range: $\Delta n_{fs} = \Delta n_{fn} = 0.328$ at $\lambda = 633$ nm; $\Delta n_{fs} = \Delta n_{fn} = 0.332$ at $\lambda = 550$ nm; $\Delta n_{fs} = \Delta n_{fn} = 0.338$ at $\lambda = 450$ nm, where $\Delta n_{fs} = ns - nf$, $\Delta n_{fn} = nn - nf$. The measurements showed substantially small values of the absorption coefficients of the organic retardation layer in a visible spectral range of 380-780 nm.

EXAMPLE 2

Figure 10A:
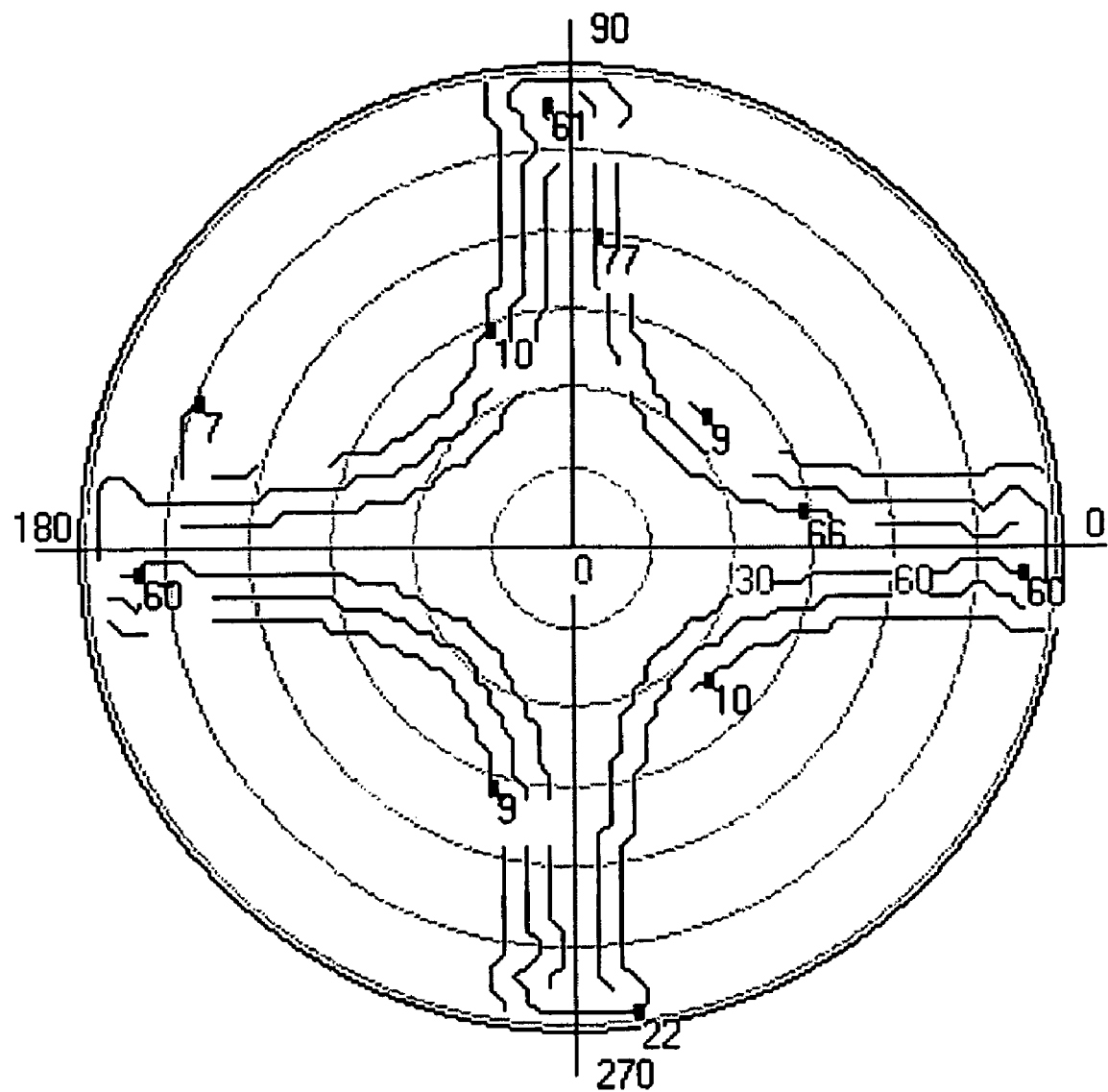
FIG. 10a shows the contrast ratio of a non-compensated liquid crystal display, calculated at a wavelength of incident light equal to 450 nm.
Figure 10B:
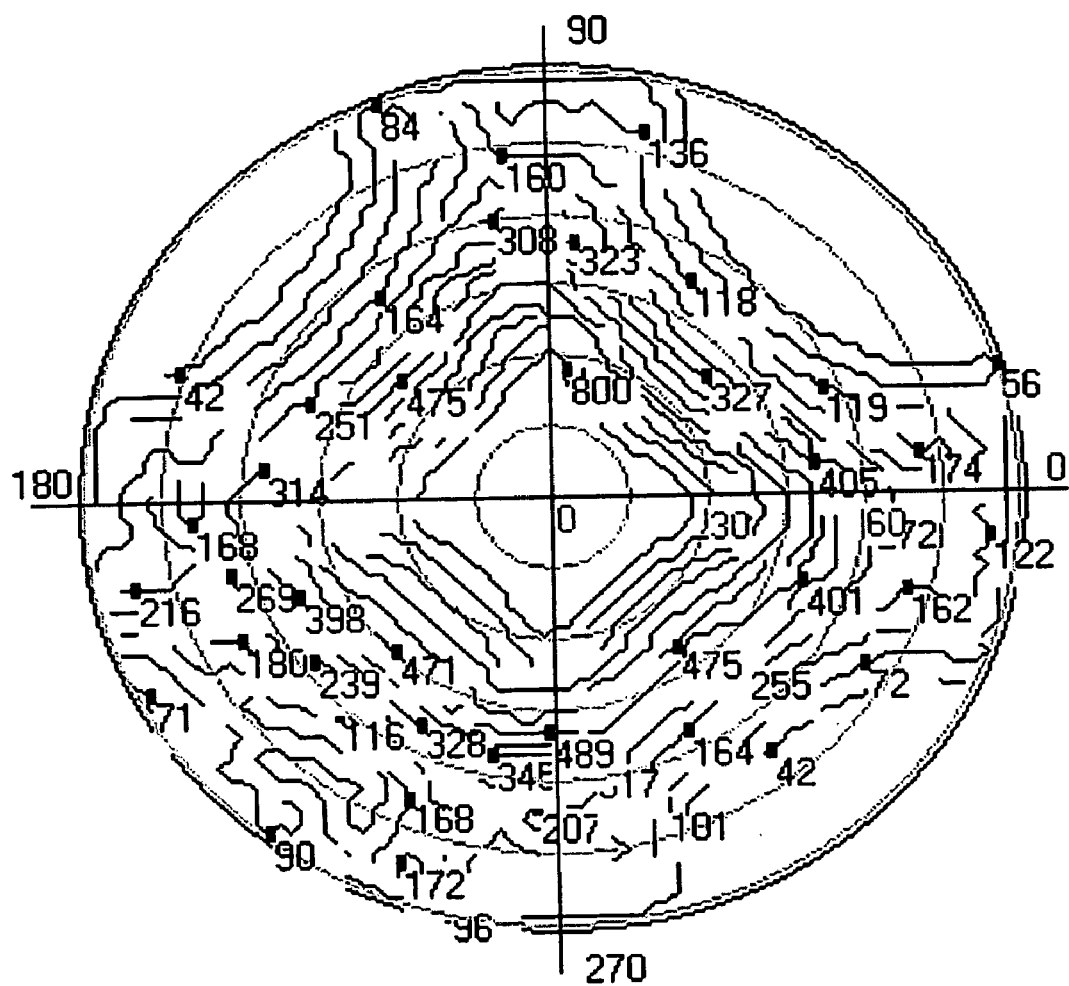
FIG. 10b shows the contrast ratio of the liquid crystal display according to the embodiment of the present invention shown in FIG. 5, calculated at a wavelength of incident light equal to 450 nm.
Figure 11A:
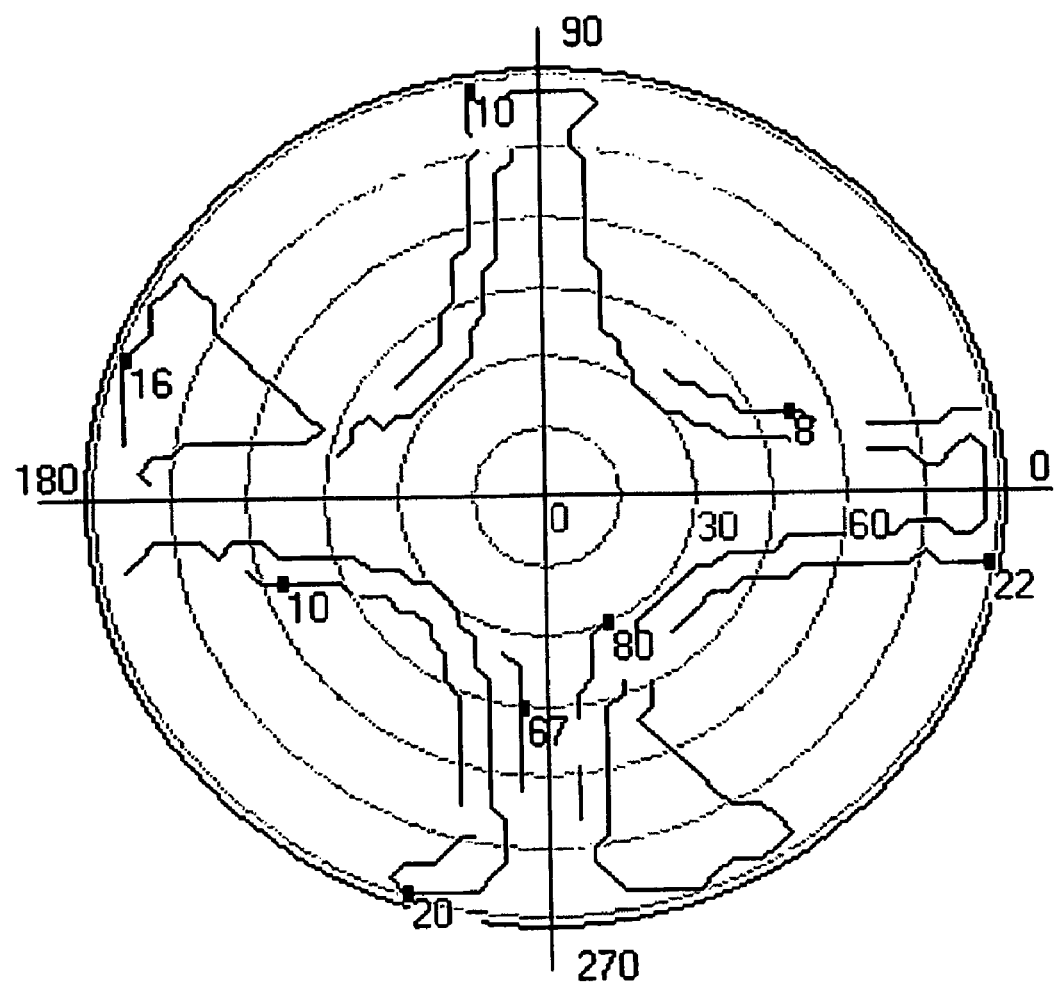
FIG. 11a shows the contrast ratio of a non-compensated liquid crystal display, calculated at a wavelength of incident light equal to 550 nm.
Figure 11B:
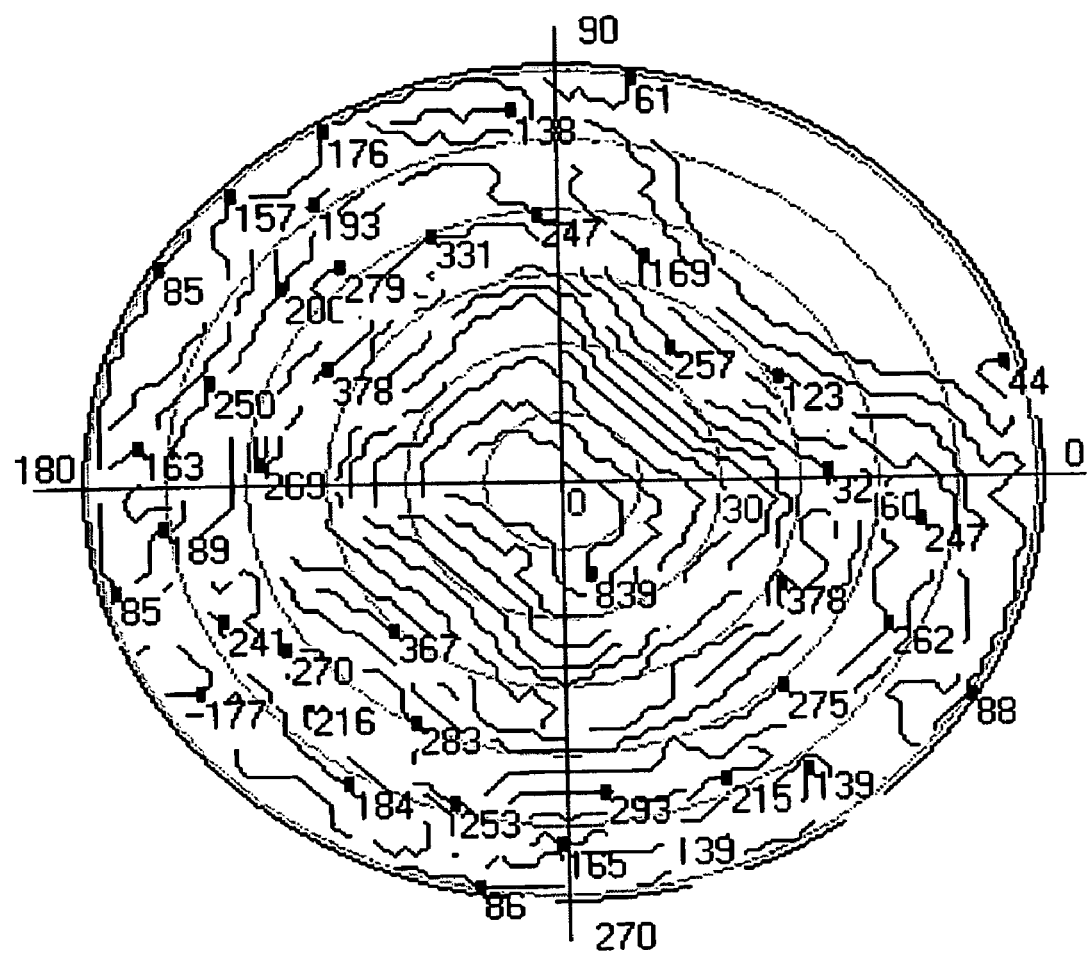
FIG. 11b shows the contrast ratio of the liquid crystal display according to the embodiment of the present invention shown in FIG. 5, calculated at a wavelength of incident light equal to 550 nm.
Figure 12A:
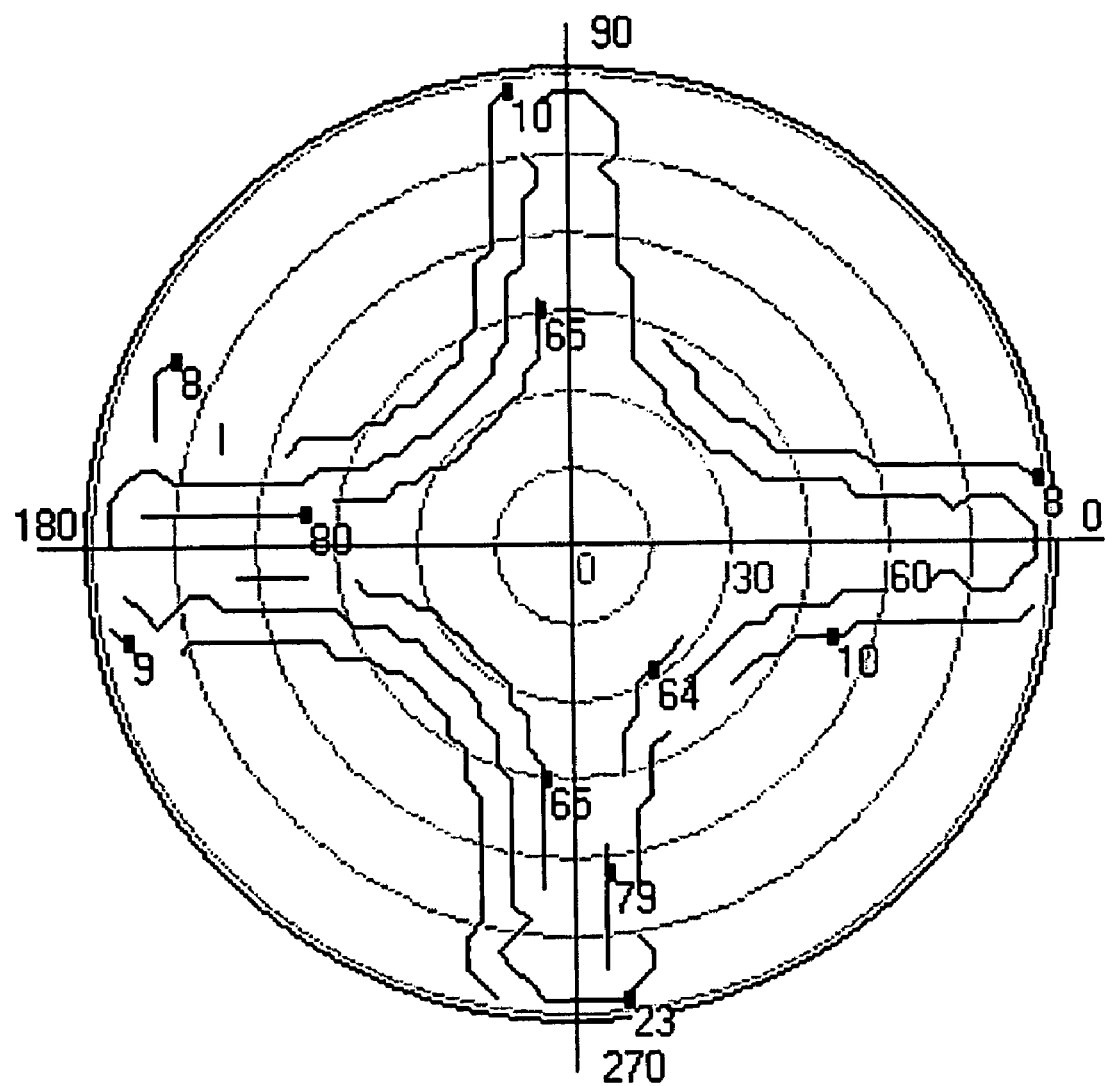
FIG. 12a shows the contrast ratio of a non-compensated liquid crystal display, calculated at a wavelength of incident light equal to 650 nm.
Figure 12B:
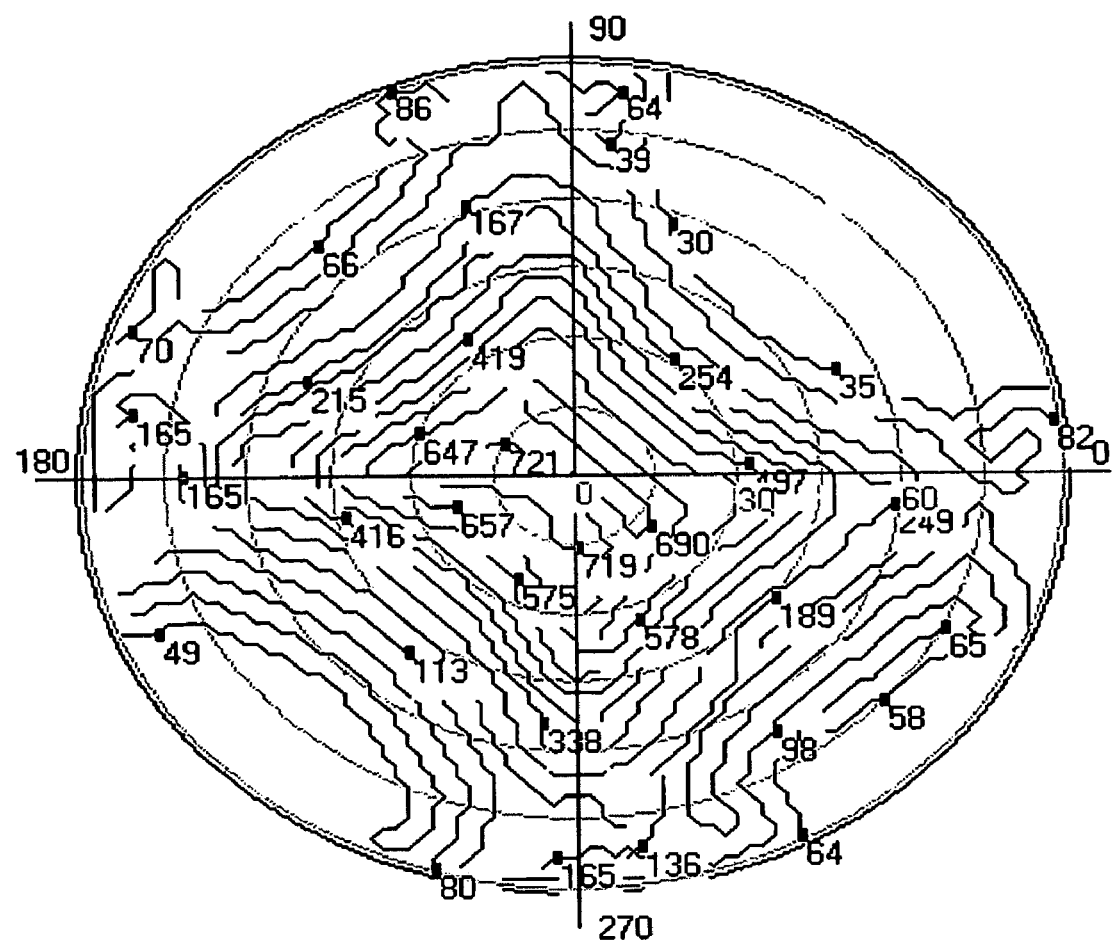
FIG. 12b shows the contrast ratio of the liquid crystal display according to the embodiment of the present invention shown in FIG. 5, calculated at a wavelength of incident light equal to 650 nm.

This example describes one preferred embodiment of the liquid crystal display according to the present invention. A schematic diagram of said liquid crystal display is shown in FIG. 5. The liquid crystal display is based on a liquid crystal cell (6) of the vertical alignment type, which represents a liquid crystal layer with retardation equal to 275 nm. The pair of polarizers (2 and 10) are arranged on each side of the liquid crystal cell, and two compensating structures (3 and 7) are formed—one between the liquid crystal cell and the first polarizer (2) and another between the liquid crystal cell and the second polarizer (10). The transmission axis (11) of the first polarizer is perpendicular to the transmission axis (18) of the second polarizer. The first compensating structure (3) comprises a retardation layer (4) of the first type, having slow (12) and fast (13) axes lying substantially in the plane of layer (4), and a retardation layer (5) of the second type representing a negative C-plate with the optical axis (14) directed substantially perpendicular to the plane of layer (5). The retardation layer (4) is arranged so that its fast principal axis (13) is perpendicular to the transmission axis (11) of polarizer (2). The retardation layer (4) was formed using the method described in Example 1. This retardation layer is characterized by the retardation parameter $R_A$ equal to 250 nm. There are two optimal sets of values for the retardation parameter $R_{TAC} = R_C$ of retardation layer (5) of the second type made of triacetyl cellulose (TAC): 130 nm and 790 nm. The second compensating structure (7) comprises a retardation layer (9) of the first type, having slow (17) and fast (16) axes lying substantially in the plane of layer (9), and a retardation layer (8) of the second type representing a negative C-plate with the optical axis (15) directed substantially perpendicular to the plane of layer (8). The retardation layer (9) of the first type is arranged so that the fast principal axis (16) of this layer is perpendicular to the transmission axis (18) of polarizer (10). The retardation layer (9) of the first type, as well as retardation layer (4), was formed using the method described in Example 1. The retardation layer (9) is characterized by the retardation parameter $R_A$ equal to 250 nm. The retardation layer (8) of the second type was also made of TAC. The retardation parameter $R_{TAC}$ of retardation layer (8) was the same as the retardation parameter $R_{TAC}$ of retardation layer (5). Retardation layers of the second type (5 and 8) are situated closer to liquid crystal cell (6) than the retardation layers of the first type (4 and 9). The contrast ratio versus a viewing angle calculated for the light with a wavelength of 450 nm is shown in FIG. 10a for a non-compensated liquid crystal display, and in FIG. 10b for a liquid crystal display (VA-LCD) according to the present invention. FIGS. 11a and 11b show the contrast ratios calculated for an incident light wavelength of 550 nm. The calculations were performed for a non-compensated liquid crystal display (FIG. 11a) and for a liquid crystal display according to the present invention (FIG. 11b). The contrast ratios calculated for the incident light with a wavelength of 650 nm are shown in FIGS. 12a and 12b for non-compensated and compensated liquid crystal display respectively. The lower contrast ratio for large angles at azimuth of +45 degrees is a consequence of single domain LC cell with the director reorientation plane at azimuth of +45°. In case of multidomain cells (MVA mode) this degradation of the contrast is absent. The viewing angle color shift characteristics of the liquid crystal display according to the present invention are given in Table 8. The liquid crystal display was in the field-On (bright) state at U=5V. The calculations were performed for an azimuthal viewing angle of −45 deg.

TABLE 8

Viewing angle color shift characteristics of a VA-LCD in the bright state at U = 5 V for an azimuthal viewing angle of −45 deg

| Zenithal viewing angle, deg | Color coordinates (x, y) according to CIE for a Standard Colorimetric Observer | | |
|---|---|---|---|
| | Light source (D65) | Non-compensated design | Present VA-LCD |
| 0 | (0.316, 0.335) | (0.301, 0.327) | (0.300, 0.328) |
| 45 | (0.316, 0.335) | (0.307, 0.335) | (0.340, 0.368) |
| 65 | (0.316, 0.335) | (0.314, 0.342) | (0.398, 0.414) |

The viewing angle color shift characteristics of the liquid crystal display according to the present invention calculated for an azimuthal viewing angle of 0 deg are given in Table 10.

TABLE 10

Viewing angle color shift characteristics of VA-LCD in the
bright state at U = 5 V for an azimuthal viewing angle of 0 deg

| Zenithal viewing angle, deg | Color coordinates (x, y) according to CIE for a Standard Colorimetric Observer | | |
|---|---|---|---|
| | Light source (D65) | Non-compensated design | Present VA-LCD |
| 0 | (0.316, 0.335) | (0.301, 0.327) | (0.300, 0.328) |
| 45 | (0.316, 0.335) | (0.307, 0.335) | (0.289, 0.313) |
| 65 | (0.316, 0.335) | (0.314, 0.342) | (0.288, 0.308) |

Thus, the liquid crystal display according to the present invention provides high contrast ratio for the entire visible spectral range in a very broad interval of viewing angles. The properties of the present design allow a roll-to-roll fabrication procedure to be used for making the retardation layers and polarizers in one process.

EXAMPLE 3

Figure 13:
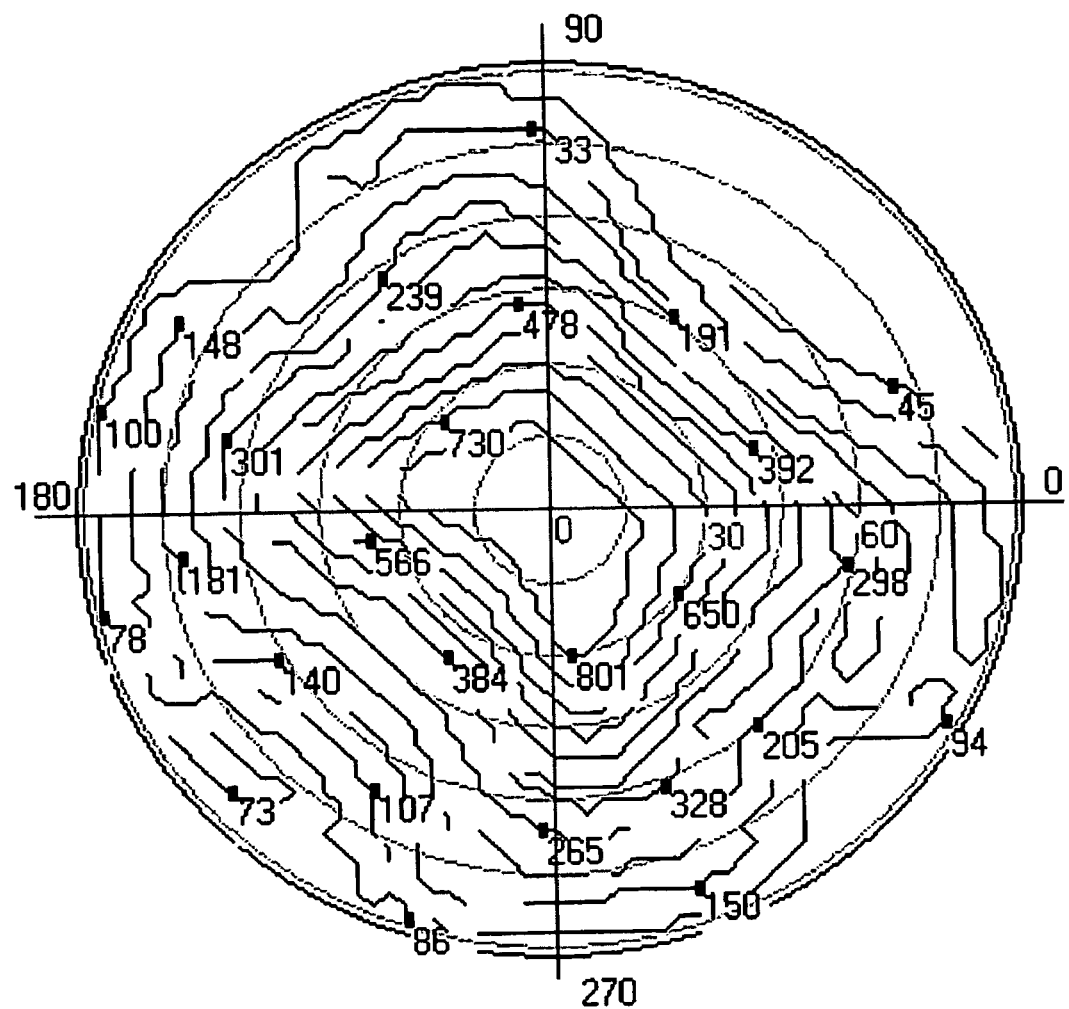
FIG. 13 shows the contrast ratio of the liquid crystal display according to the embodiment of the present invention shown in FIG. 6, calculated at a wavelength of incident light equal to 550 nm (the retardation layers of the second type have the retardation parameter $R_{TAC}$=180 nm and retardation layers of the first type have the retardation parameter $R_A$=98 nm).
Figure 14:
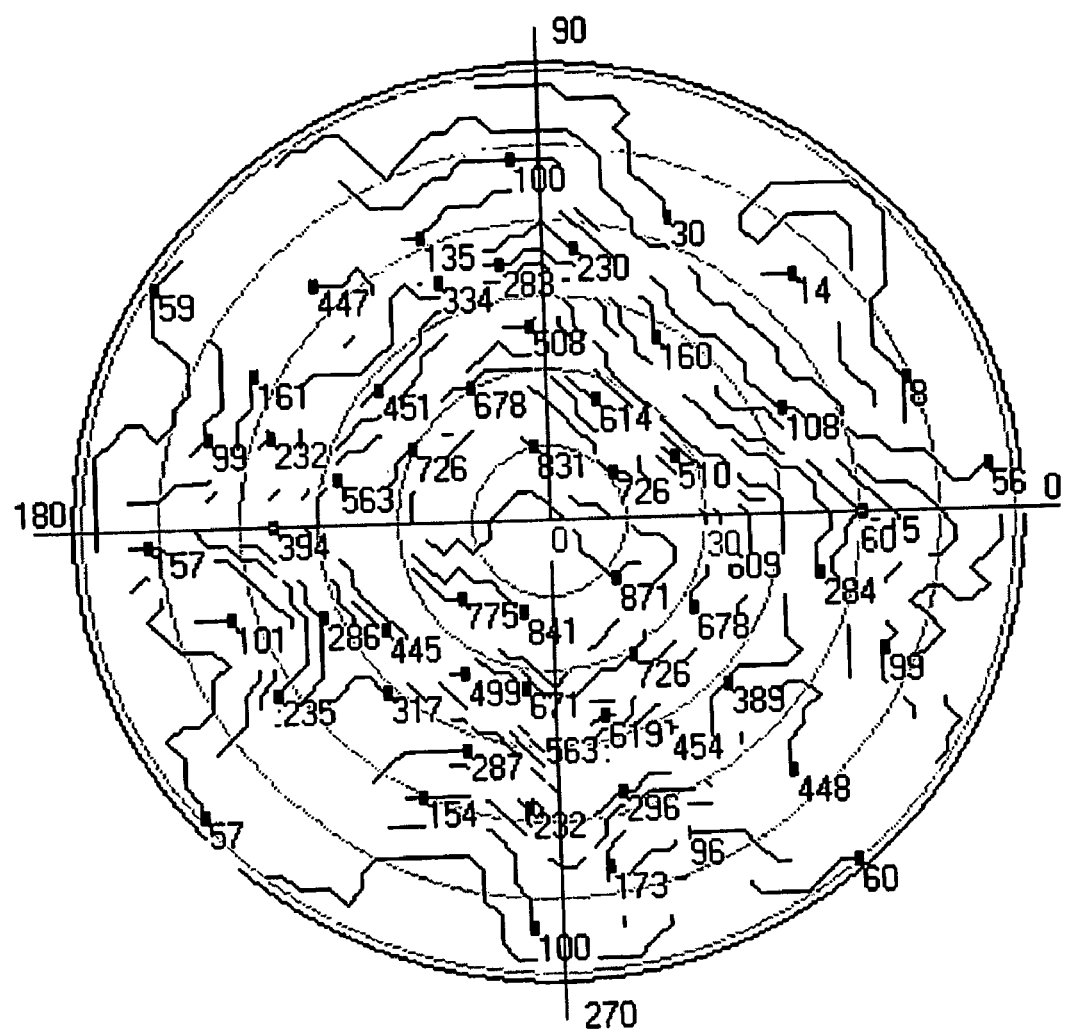
FIG. 14 shows the contrast ratio of the liquid crystal display according to the second embodiment of the present invention shown in FIG. 6, calculated at a wavelength of incident light equal to 550 nm (the retardation layers of the second type have the retardation parameter $R_{TAC}$=60 nm and the retardation layers of the first type have the retardation parameter $R_A$=424 nm).

This example describes another preferred embodiment of the liquid crystal display according to the present invention. The schematic diagram of said liquid crystal display is shown in FIG. 6. The liquid crystal display is based on a liquid crystal cell (6) of the vertical alignment type, which represents a liquid crystal layer with retardation equal to 275 nm. The pair of polarizers (2 and 10) are arranged on both sides of the liquid crystal cell, and two compensating structures (3 and 7) are formed—one between the liquid crystal cell and the first polarizer (2) and another between the liquid crystal cell and the second polarizer (10). The transmission axis (11) of the first polarizer is perpendicular to the transmission axis (18) of the second polarizer. The first compensating structure (3) comprises a retardation layer (4) of a first type, having slow (12) and fast (13) axes lying substantially in the plane of layer (4), and a retardation layer (5) of a second type representing a negative C-plate with the optical axis (14) directed substantially perpendicular to the plane of layer (5). The retardation layer (4) is arranged so that the slow principal axis (12) of this layer is perpendicular to the transmission axis (11) of polarizer (2). The retardation layer (4) was formed using the method described in Example 1. The retardation layer (4) is characterized by the retardation parameter $R_A$ equal to 98 nm, while the value of retardation parameter for retardation layer (5) of the second type made of TAC is $R_{TAC}=R_C=180$ nm. In another variant of this embodiment, the retardation layer (4) is characterized by the retardation parameter $R_A$ equal to 424 nm, while the value of this parameter for retardation layer (5) of the second type made of TAC is $R_{TAC}=60$ nm. The second compensating structure (7) comprises a retardation layer (9) of a first type, having slow (17) and fast (16) axes lying substantially in the plane of layer (9), and a retardation layer (8) of a second type representing a negative C-plate with the optical axis (15) directed substantially perpendicular to the plane of layer (8). The retardation layer (9) of the first type is arranged so that the slow principal axis (17) of this layer is perpendicular to the transmission axis (18) of polarizer (10). The retardation layer of the first type (9), as well as the retardation layer (4), was formed by the method described in Example 1. The retardation layer (9) is characterized by the retardation parameter $R_A$ equal to 98 nm or 424 nm. The retardation layer (8) of the second type was also made of TAC. The retardation parameter $R_{TAC}$ of retardation layer (8) was equal to the value of $R_{TAC}$ for the retardation layer (5). The retardation layers of the second type (5 and 8) are located closer to the liquid crystal cell (6) than the retardation layers of the first type (4 and 9). The contrast ratio calculated for an incident light wavelength of 550 nm is shown in FIG. 13 for a system with retardation layers of the second type (5 and 8) having the retardation parameter $R_{TAC}=180$ nm and retardation layers of the first type (4 and 9) having the retardation parameter $R_A=98$ nm. FIG. 14 shows the contrast ratios calculated for the incident light with a wavelength of 550 nm for liquid crystal display according to present invention with retardation layers of the second type (5 and 8) having the retardation parameters $R_{TAC}=60$ nm, and for retardation layers of the first type (4 and 9) having the retardation parameters $R_A=424$ nm.

EXAMPLE 4

The example describes preparation of an organic compound having general structural formula 1 shown in Table 2. A 4,4'-(5,5-Dioxidodibenzo[b,d]thiene-3,7-diyl)dibenzenesulfonic acid was prepared by sulfonation of 1,1':4',1":4",1'''-quaterphenyl.

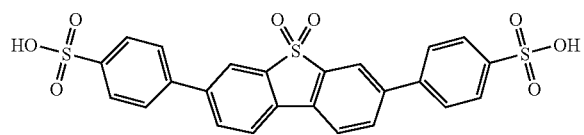

A 1,1':4',1":4",1'''-Quaterphenyl (10 g) was charged into 20% oleum (100 ml). Reaction mass was agitated for 5 hours at ambient conditions. After that the reaction mixture was diluted with water (170 ml). The final sulfuric acid concentration became ~55%. The precipitate was filtered and rinsed with an acetic acid (~200 ml). Filter cake was dried in oven at ~110° C. The process yielded 8 g of 4,4'-(5,5-Dioxidodibenzo[b,d]thiene-3,7-diyl)dibenzenesulfonic acid. H$^1$NMR (Brucker Avance-600, DMSO-d$_6$, δ, ppm): 7.735 (d, 4H, 4CH$^{Ar}$(3,3',5,5')); 7.845 (d, 4H, 4CH$^{Ar}$(2,2',6,6')); 8.165 (dd, 2H, 2CH$^{Ar}$(2,8)); 8.34 (m, 4H, 4CH$^{Ar}$(1,9,4,6)). The lectron spectrum (Spectrometer UV/VIS Varian Cary 500 Scan, aqueous solution): $\lambda_{max1}=218$ nm (∈=3.42*10$^4$); $\lambda_{max2}=259$ nm (∈=3.89*10$^4$); $\lambda_{max3}=314$ nm (∈=4.20*10$^4$). Mass spectrum (Brucker Daltonics Ultraflex TOF/TOF): molecular ion (M$^-$=529), FW=528.57.

EXAMPLE 5

The example shows the preparation of organic thin biaxial layer formed from lyotropic liquid crystal solution. A 4,4'-(5,5-Dioxidodibenzo[b,d]thiene-3,7-diyl)benzenesulfonic acid (1 g) obtained as described in Example 4 was mixed with 3.8 ml of distilled water and 1.1 ml of 10-w % aqueous sodium solution and then stirred at room temperature (23° C.) until a lyotropic liquid solution was formed (for about 1 hour).

LCD-grade Soda Lime glass substrates were prepared for coating. The substrate was placed in Ultrasonic bath with water solution of NaOH (w/w 10%) and KMnO$_4$ (w/w 0.1%) for 30 min, then rinsed with deionized water, and subjected to compressed air stream drying. The lyotropic liquid crystal was coated onto the pretreated glass substrate with Mayer Rod #1.5 moved at linear velocity of 200 mm/s (humidity=30%, temperature=23° C.). The coated solution was subjected to compressed air stream drying and thin retardation layer of the first type was formed as the result.

The thickness of retardation layer formed was between 420 and 450 um, but it depends on the desired optical function and may vary controlling the concentration of compound in the water solution. The retardation layer formed is clear (colorless) and transparent in the optical spectral range.

Figure 15:
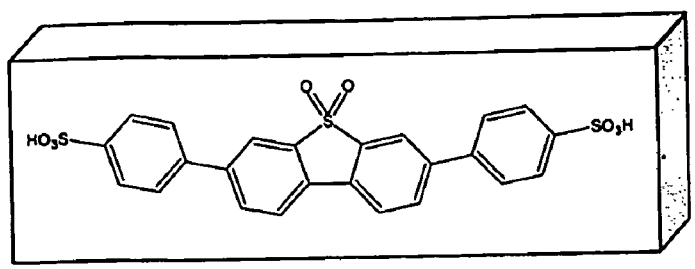
FIGS. 15-18 show a formation of biaxial retarder layer and wavelength dependence of refractive indices for thin birefringent plate according to the present invention.
Figure 16:
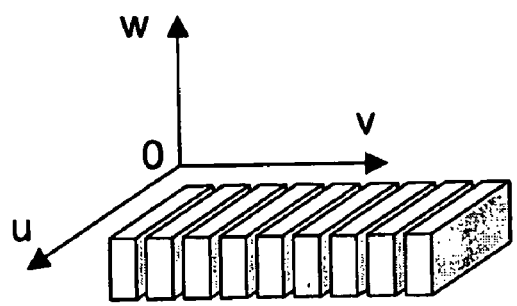
Figure 17:
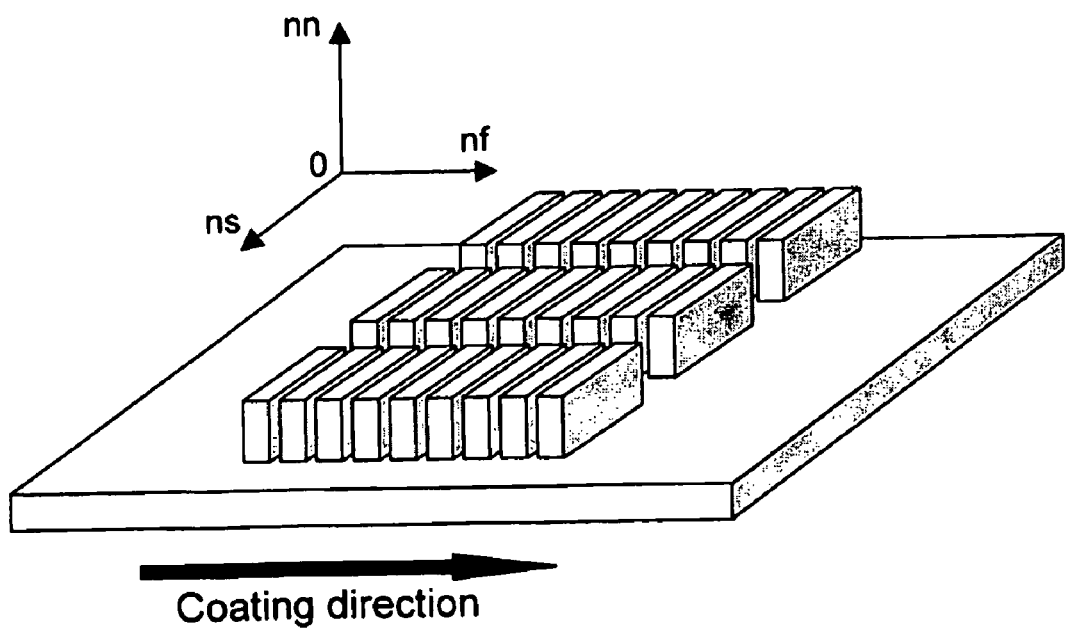
Figure 18:
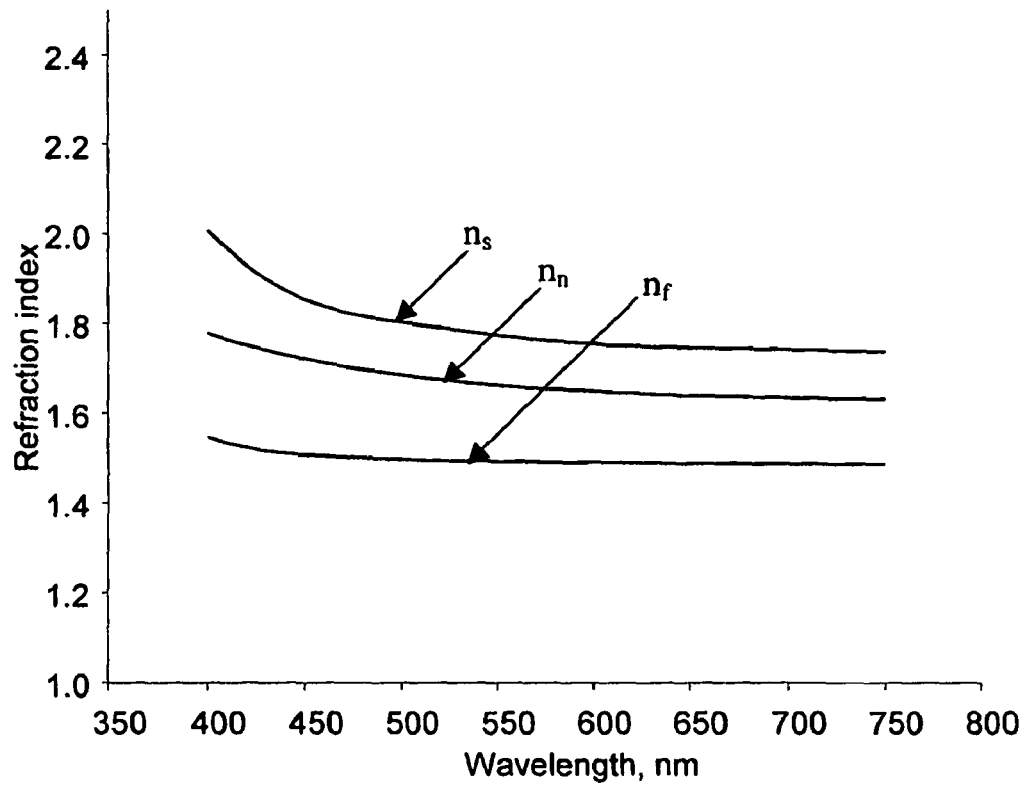

The retardation layer based on material as shown in Example 4 is characterized by fast principal axis lying in the layer plane along the coating direction. The slow principal axis lies in the layer plane also and is directed perpendicularly to the coating direction. The refractive indices directed along the fast principal axis ($n_f$), along slow principal axis ($n_s$), and along the perpendicular direction relative to layer plane ($n_n$) are found to be different. FIGS. 15-17 show a simplified sketch of molecular and supramolecular packing in solution and in dried films with respect to the substrate planes in case of biaxial retardation layer. In solution the molecules schematically shown in FIG. 15 are assembled in rod-like supramolecules as shown in FIG. 16 and can form lyotropic liquid crystal (LLC) in nematic phase. Said rod-like supramolecules have anisotropic polarizability in plane (u0w) which is perpendicular to their longitudinal axis directed along 0v-axis. During the deposition process the supramolecules are oriented under shear stress. The result is a retardation layer with supramolecules aligned in plane of a substrate along the coating direction, as shown in FIG. 17. FIG. 18 shows a wavelength dependence of refractive indices for thin biaxial plate.

EXAMPLE 6

Figure 19:
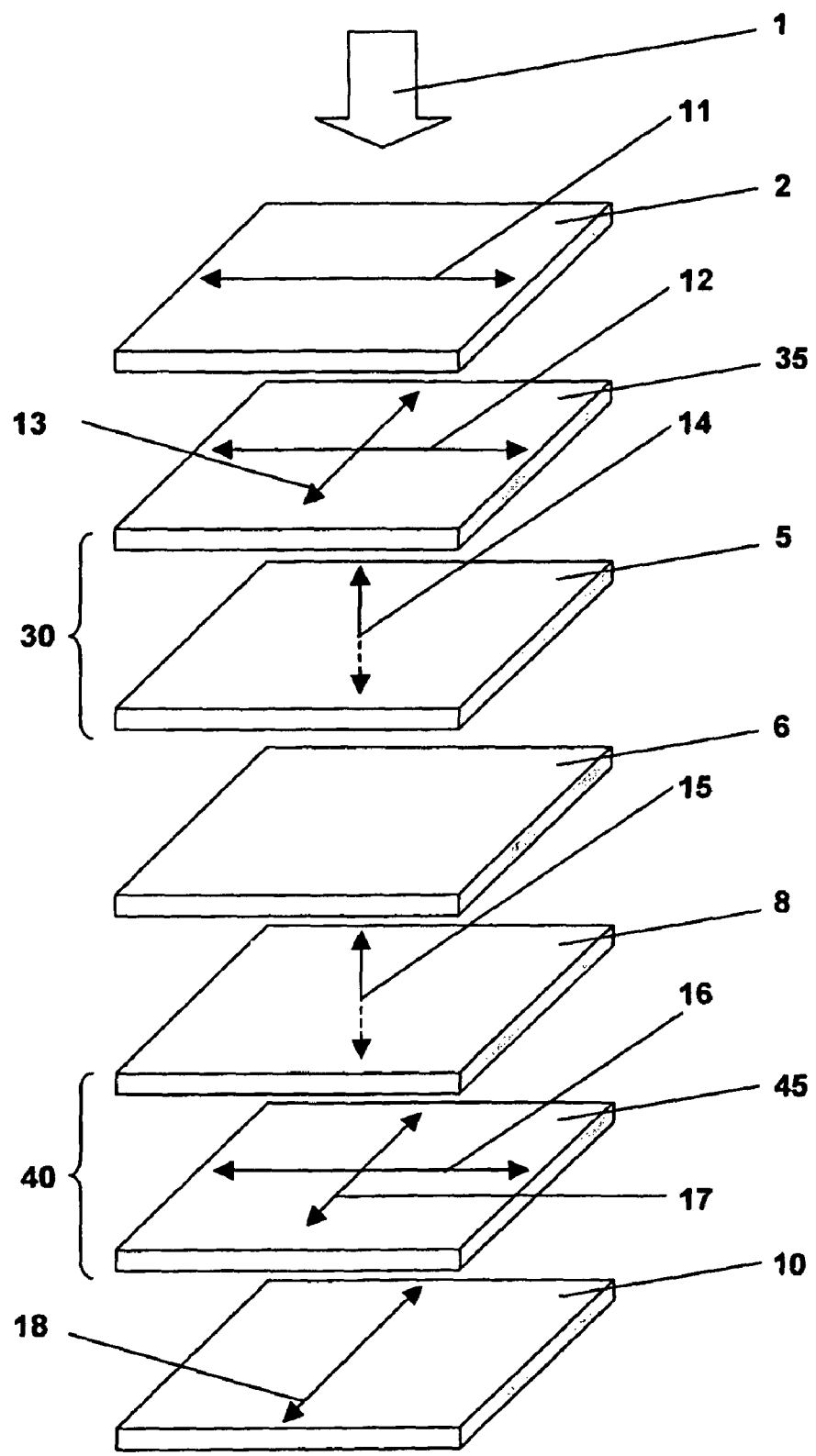
FIG. 19 is a diagram showing a construction of a liquid crystal display according to one embodiment of the present invention.
Figure 20:
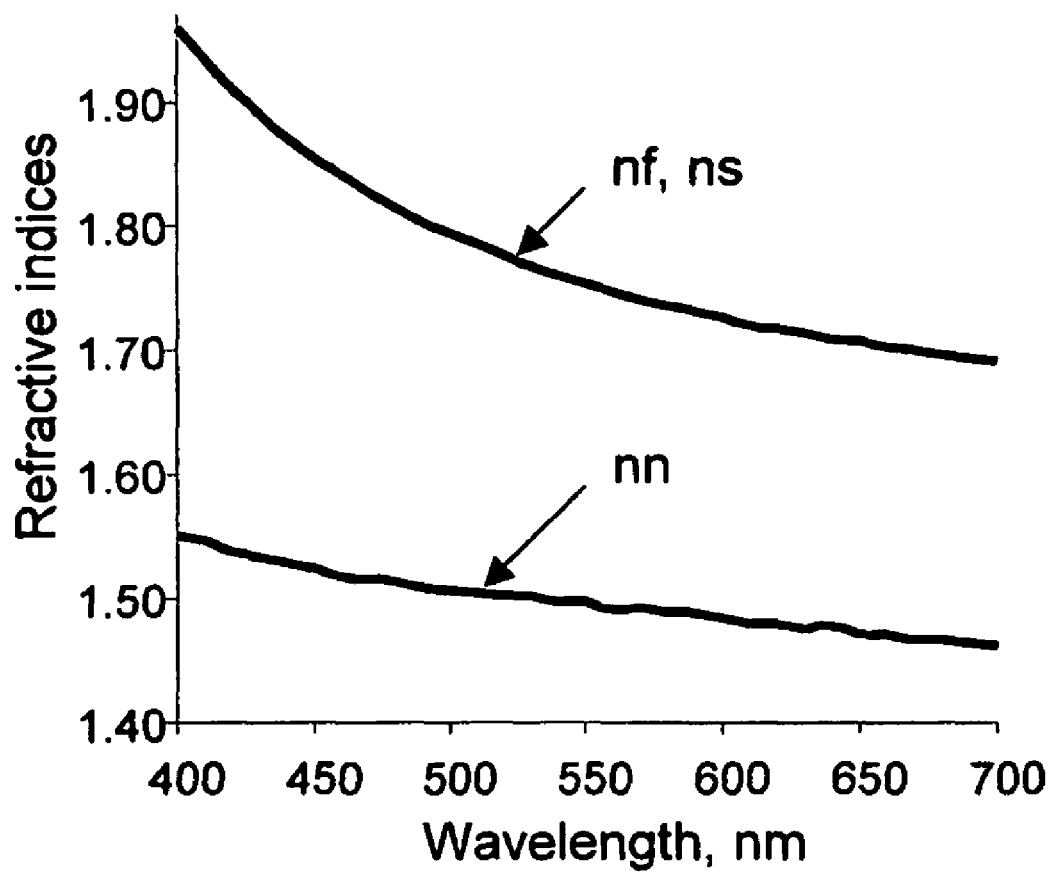
FIG. 20 shows spectral dependencies of the refractive indices of the retardation layer of the second type according to the present invention.
Figure 21:
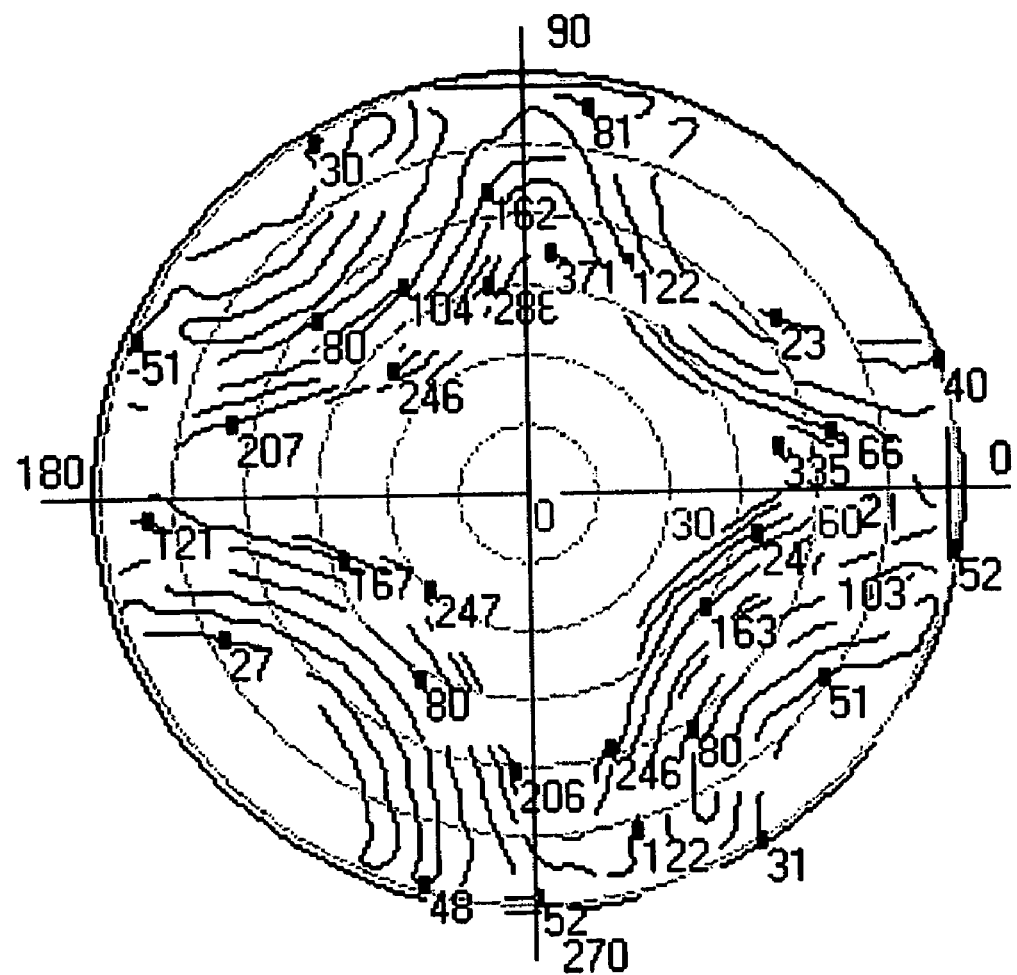
FIG. 21 shows a calculated viewing angle performance of a fifth embodiment of the present invention as shown in FIG. 19.

This example describes still another preferred embodiment of the liquid crystal display according to the present invention. FIG. 19 schematically shows a light beam (1) and a liquid crystal display which comprises a liquid crystal cell (6) of a vertical alignment mode, a pair of polarizers (2 and 10) arranged on each side of the liquid crystal cell, and two compensating structures (30 and 40) disposed between the liquid crystal cell and the first polarizer (2), and the liquid crystal cell and second polarizer (10), consequently. The transmission axis (11) of the first polarizer is perpendicular to the transmission axis (18) of the second polarizer. The first compensating structure (30) comprises a retardation layer of the first type (35) having slow (12) and fast (13) axes lying substantially in the plane of said retardation layer (35), and a retardation layer of the second type (5) as a negative C-plate with the optical axis (14) directed substantially perpendicularly to the plane of said retardation layer (5). The retardation layer (35) is arranged such that the fast principal axis (13) of said retardation layer is perpendicular to the transmission axis (11) of the polarizer (2). The retardation layer (35) is a biaxial retardation layer characterized by two in-plane refractive indices (ns and nf) and one refractive index (nn) in the normal direction which obey the following condition for electromagnetic radiation in the visible spectral range: ns>nn>nf. The second compensating structure (40) comprises a retardation layer of the first type (9) having slow (17) and fast (16) axes lying substantially in the plane of said retardation layer (45), and a retardation layer of the second type (8) as a negative C-plate with the optical axis (15) directed substantially perpendicularly to the plane of said retardation layer (8). The retardation layer of the first type (45) is arranged such that the fast principal axis (16) of said retardation layer is perpendicular to the transmission axis (18) of the polarizer (10). The retardation layer of the first type (45) is a biaxial retardation layer being characterized by two in-plane refractive indices (nf and ns) and one refractive index (nn) in the normal direction which obey the following condition for electromagnetic radiation in the visible spectral range: ns>nn>nf. The retardation layer of the first type may be made of the organic compound (4,4'-(5,5-Dioxidodibenzo[b,d]thiene-3,7-diyl) dibenzenesulfonic acid) prepared according to Example 4 and by method described in Example 5. For the retardation layer of the first type (35 and 45) all of the three principal refractive indices are different (see FIG. 18). The lowest ($n_f$=1.496 at λ=550 nm) and highest ($n_s$=1.777 at λ=550 nm) values correspond to the fast and slow principal axes respectively, which belong to the retardation layer plane. The refractive index (nn) in the normal direction is equal to 1.663 at λ=550 nm. Spectral dependencies for the principal refractive indices of a uniaxial retardation layer of the second type (-C-plate) are shown in FIG. 20. The optimal retardation $R_C$ of the second type retarder is 50 nm. Such small value of retardation allows replacing the negative C-type retardation layer by an inexpensive polymer—TAC films. The optimal retardation of a single crystal VA LC and thickness of the first type retardation layer are found to be 250 nm and 450 nm respectively. The calculated viewing angle performance of such design is illustrated in FIG. 21.

EXAMPLE 7

Figure 22:
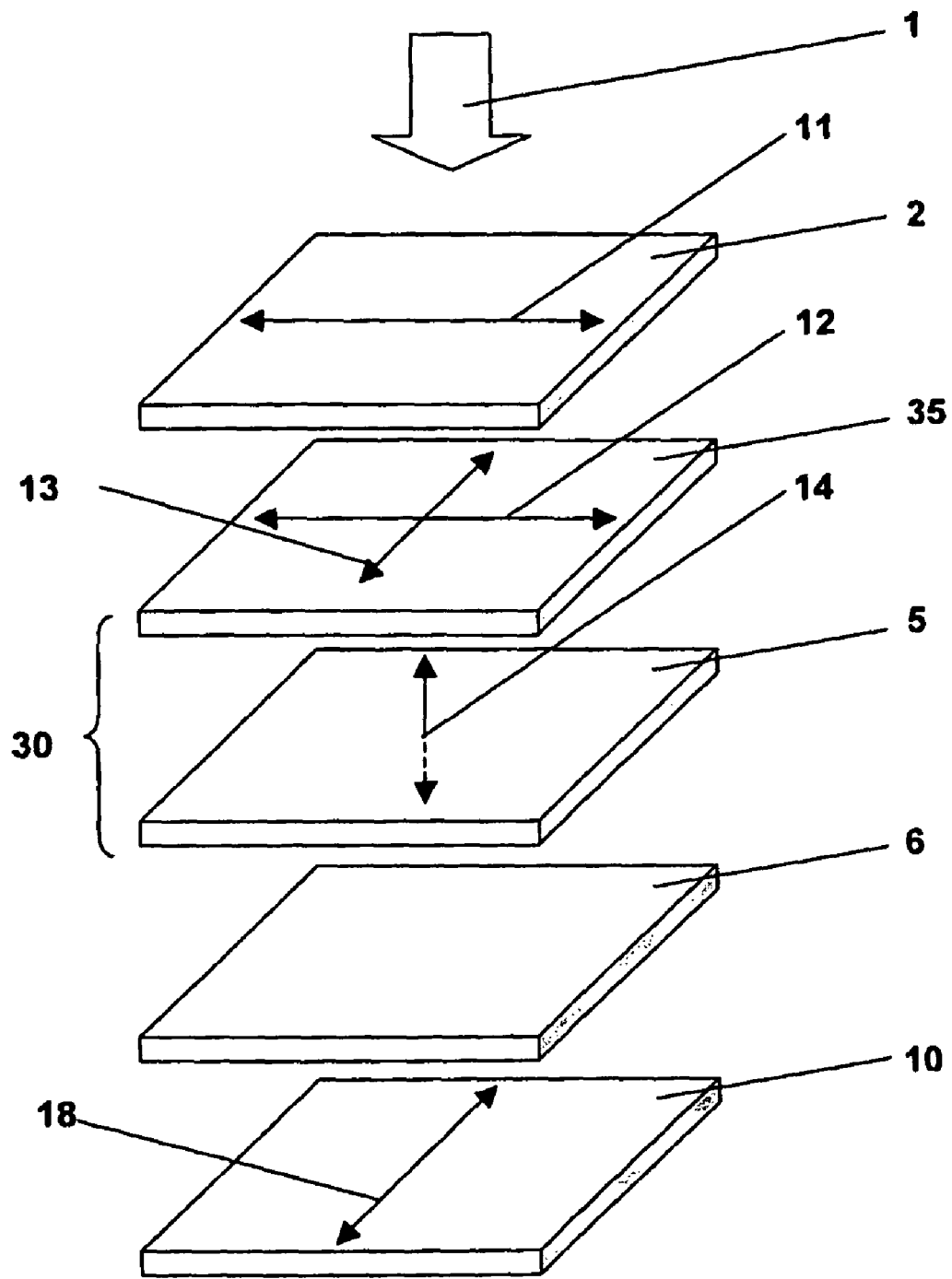
FIG. 22 is a diagram showing a construction of a liquid crystal display according to one embodiment of the present invention.
Figure 23:
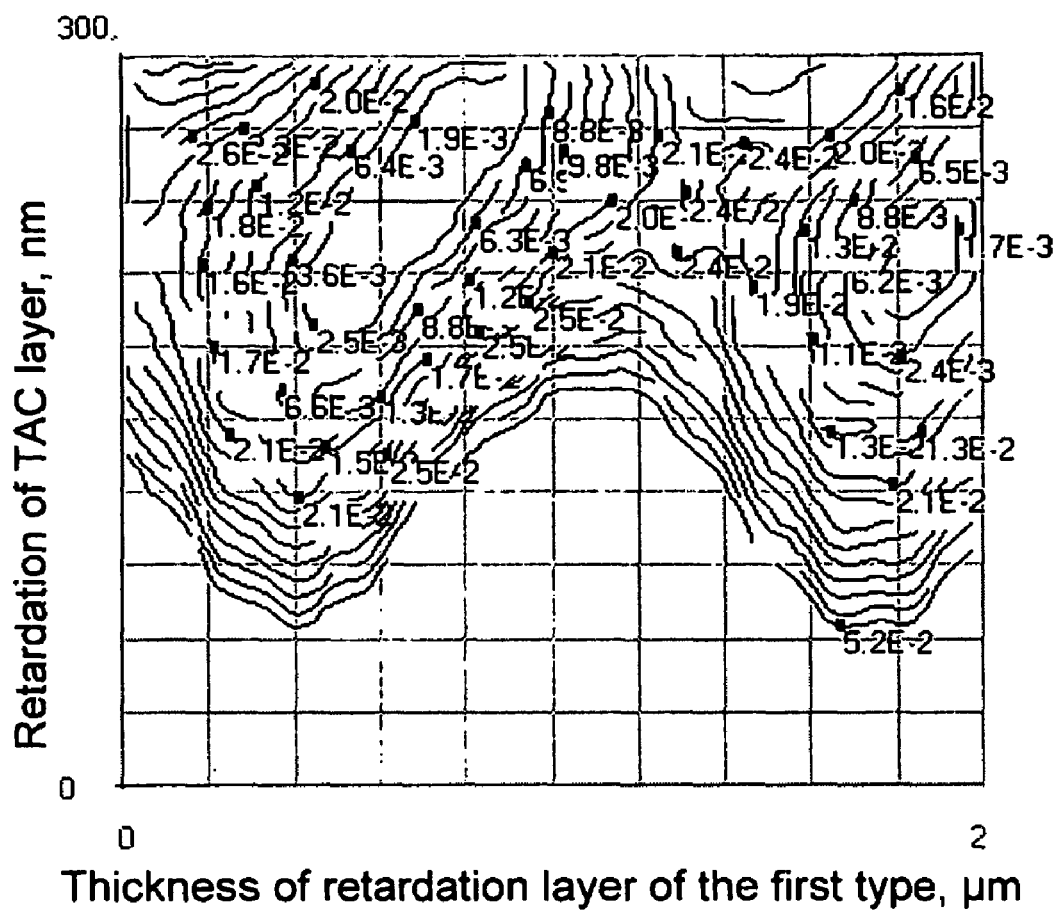
FIG. 23 shows results of numerical optimization of a liquid crystal display as shown in FIG. 22.

The example describes yet another preferred embodiment of the liquid crystal display according to the present invention. FIG. 22 schematically shows a light beam (1) and a liquid crystal display which comprises a liquid crystal cell (6) of a vertical alignment mode, a pair of polarizers (2 and 10) arranged on each side of the liquid crystal cell, and one compensating structure (30) disposed between the liquid crystal cell and the first polarizer (2). The transmission axis (11) of the first polarizer is perpendicular to the transmission axis (18) of the second polarizer. The first compensating structure (30) comprises a retardation layer of the first type (35) having slow (12) and fast (13) axes lying substantially in the layer plane, and a retardation layer of the second type (5) as a negative C-plate with the optical axis (14) directed substantially perpendicular to the retardation layer plane. The retardation layer (35) is arranged such that the fast principal axis (13) of said retardation layer is perpendicular to the transmission axis (11) of the polarizer (2). The retardation layer (35) is a biaxial retardation layer characterized by two in-plane refractive indices (ns and nf) and one refractive index (nn) in the normal direction which obey the following condition for electromagnetic radiation in the visible spectral range: ns>nn>nf. For the retardation layer of a first type (35) all of the three principal refractive indices nf, ns and nn are different and equal to 1.595, 2.005 and 1.826 respectively at λ=550 nm. The retardation layer of the retarder of the second type is made of polymer TAC film with retardation equal to 50 nm. Results of numerical optimization are shown in FIG. 23. Optimization was carried out with respect to light leakage in the field-off state for viewing angle θ=70° at λ=550 nm. The minimal leakage is at a thickness of retardation layer of the first type equal to 0.65 µm and retardation of TAC of 230 nm.

EXAMPLE 8

Figure 24:
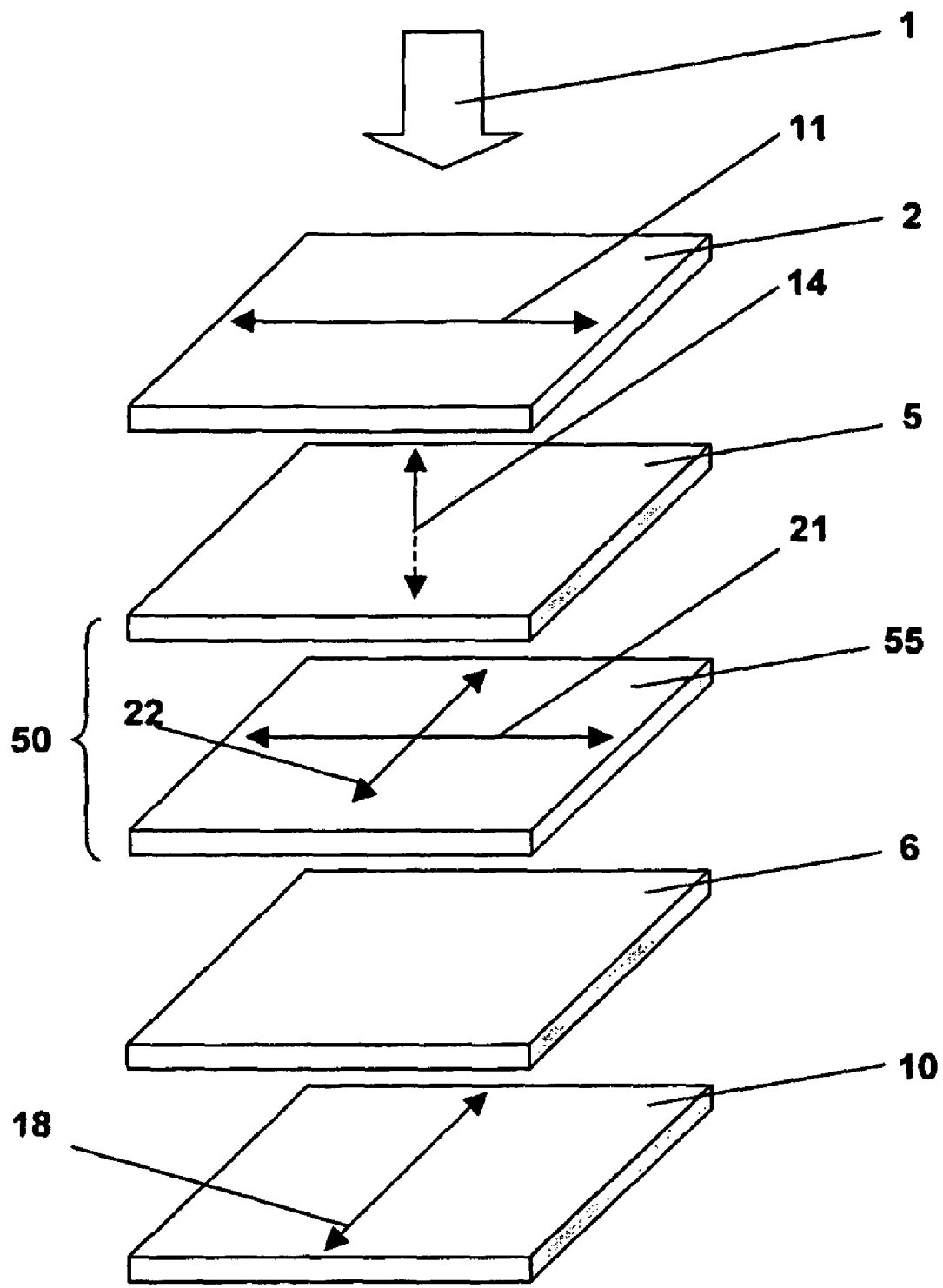
FIG. 24 is a diagram showing a construction of a liquid crystal display according to one embodiment of the present invention.
Figure 25:
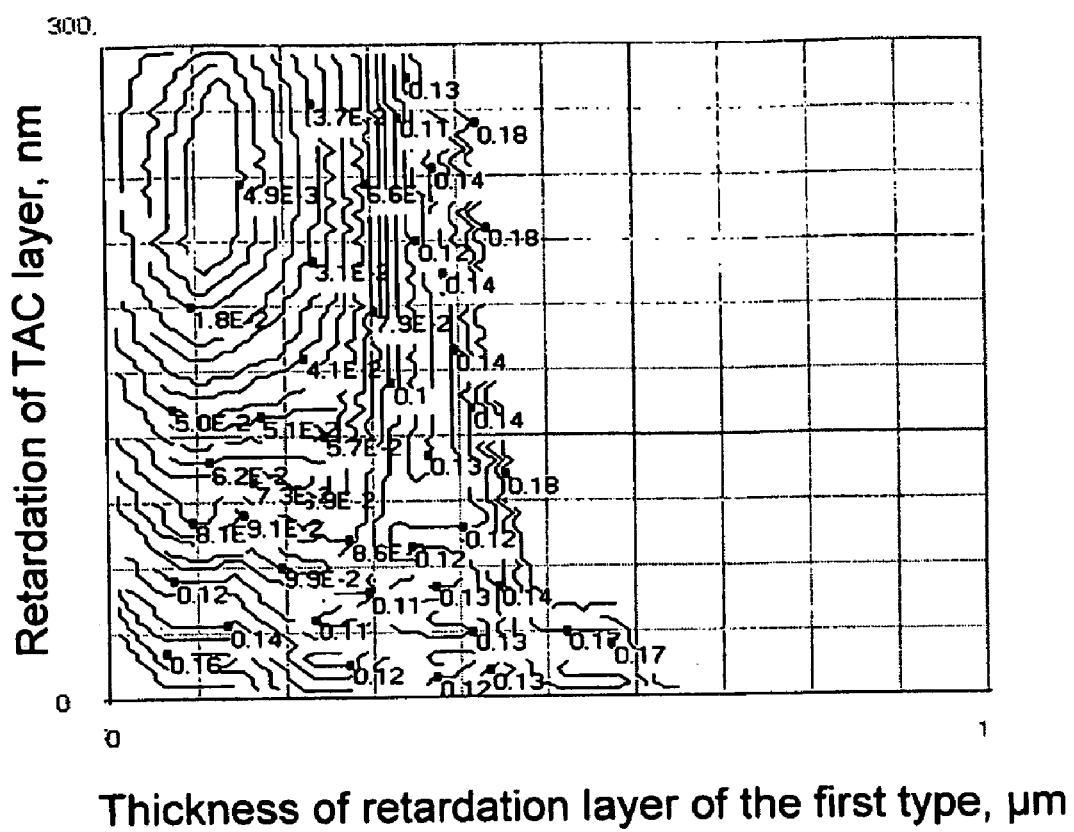
FIG. 25 shows results of numerical optimization of a liquid crystal display as shown in FIG. 24.

The example describes one preferred embodiment of the liquid crystal display according to the present invention. FIG. 24 schematically shows a light beam (1) and a liquid crystal display which comprises a liquid crystal cell (6) of a vertical alignment mode, a pair of polarizers (2 and 10) arranged on each side of the liquid crystal cell, and one compensating structure (50) disposed between the liquid crystal cell and the first polarizer (2). The transmission axis (11) of the first polarizer is perpendicular to the transmission axis (18) of second polarizer. The compensating structure (50) comprises a retardation layer of the first type (55) having slow (21) and fast (22) axes lying substantially in the layer plane, and a retardation layer of the second type (5) as a negative C-plate with the optical axis (14) directed substantially perpendicular to the layer plane. The retardation layer (55) is arranged such that the fast principal axis (22) of said retardation layer is perpendicular to the transmission axis (11) of the polarizer (2). The retardation layer (55) is a biaxial retardation layer characterized by two in-plane refractive indices (ns and nf) and one refractive index (nn) in the normal direction which obey the following condition for electromagnetic radiation in the visible spectral range: ns>nn>nf. For the retardation layer of the first type (55) all of the three principal refractive indices nf, ns and nn are different and equal to 1.595, 2.005 and 1.826 respectively at λ=550 nm. The retardation layer of the retarder of the second type is made of polymer TAC film with retardation $d \cdot \Delta n_{TAC}$=230 nm. Results of numerical optimization are shown in FIG. 25. The minimal leakage is at thickness of retardation layer of the first type equal to 0.1-0.12 μm.

EXAMPLE 9

Figure 26:
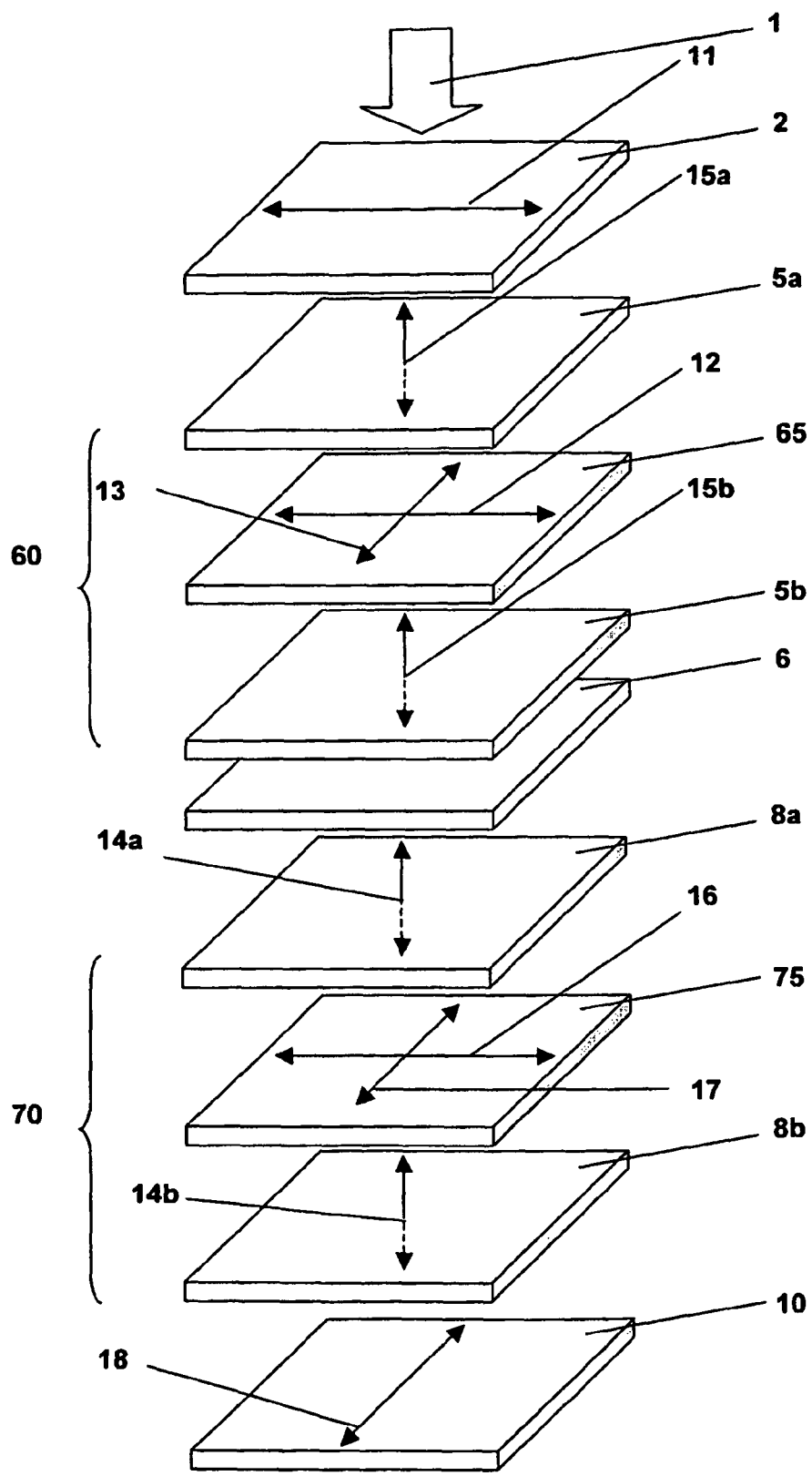
FIG. 26 is a diagram showing a construction of a liquid crystal display according to one embodiment of the present invention.
Figure 27:
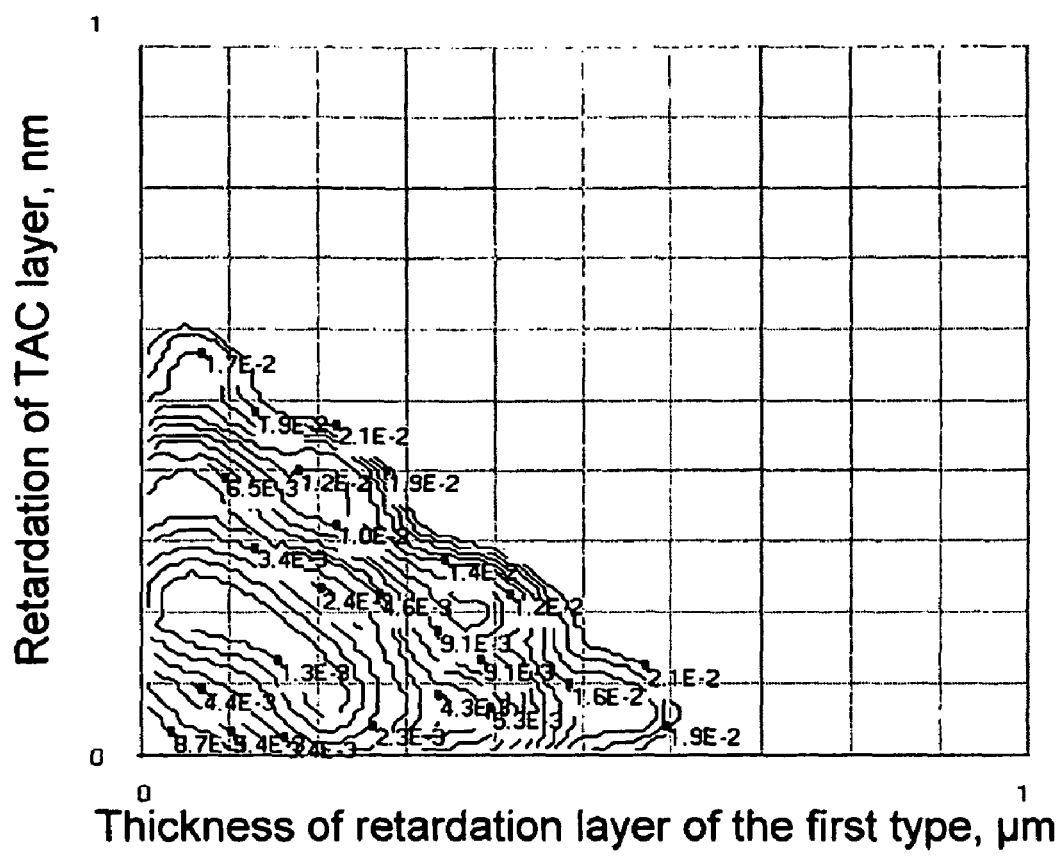
FIG. 27 shows results of numerical optimization of a liquid crystal display as shown in FIG. 26.

The example describes another preferred embodiment of the liquid crystal display according to the present invention. FIG. 26 schematically shows a light beam (1) and a liquid crystal display which comprises a liquid crystal cell (6) of a vertical alignment mode, a pair of polarizers (2 and 10) arranged on each side of the liquid crystal cell, and two compensating structures (60 and 70) disposed between the liquid crystal cell and the first polarizer (2) and the liquid crystal cell and second polarizer (10) respectively. The transmission axis (11) of the first polarizer is perpendicular to the transmission axis (18) of the second polarizer. The first compensating structure (60) comprises a retardation layer of the first type (65) having slow (12) and fast (13) axes lying substantially in the plane of said retardation layer (65), and two retardation layers of the second type (5a and 5b) as a negative C-plates with the optical axes (15a and 15b) directed substantially perpendicularly to the plane of said retardation layers (5a and 5b) respectively. The retardation layer (65) is arranged such that the fast principal axis (13) of said retardation layer is perpendicular to the transmission axis (11) of the polarizer (2). The compensating structure (60) comprises first (5a) and second (5b) retardation layers of the second type arranged on each side of one (65) retardation layer of the first type. The retardation layer (65) is a biaxial retardation layer characterized by two in-plane refractive indices (ns and nf) and one refractive index (nn) in the normal direction which obey the following condition for electromagnetic radiation in the visible spectral range: ns>nn>nf. The second compensating structure (70) comprises a retardation layer of the first type (75) having slow (17) and fast (16) axes lying substantially in the plane of said retardation layer (75), and two retardation layers of the second type (8a and 8b) as a negative C-plates with the optical axes (14a and 14b) directed substantially perpendicularly to the plane of said retardation layers (8a and 8b). The compensating structure (70) comprises the first (8a) and the second (8b) retardation layers of the second type arranged on each side of one (75) retardation layer of the first type. The retardation layer of the first type (75) is arranged such that the fast principal axis (16) of said retardation layer is perpendicular to the transmission axis (18) of the polarizer (10). The retardation layer of the first type (75) is a biaxial retardation layer and it is characterized by two in-plane refractive indices (nf and ns) and one refractive index (nn) in the normal direction which obey the following condition for electromagnetic radiation in the visible spectral range: ns>nn>nf. For the retardation layers of the first type (65 and 75) all of the three principal refractive indices nf, ns and nn are different and equal to 1.595, 2.005 and 1.826 respectively at λ=550 nm. The retardation layer of the retarder of the second type is made of polymer TAC film with retardation $d \Delta n_{TAC}$=50 nm. Results of numerical optimization are shown in FIG. 27. The minimal leakage is at thickness of retardation layer of the first type equal to 0.15 μm.

EXAMPLE 10

The example describes syntheses of the mixture of bisbenzimidazo[1',2':3,4;1'',2'':5,6][1,3,5]triazino[1,2-a]benzimidazole-tricarboxylic acids:

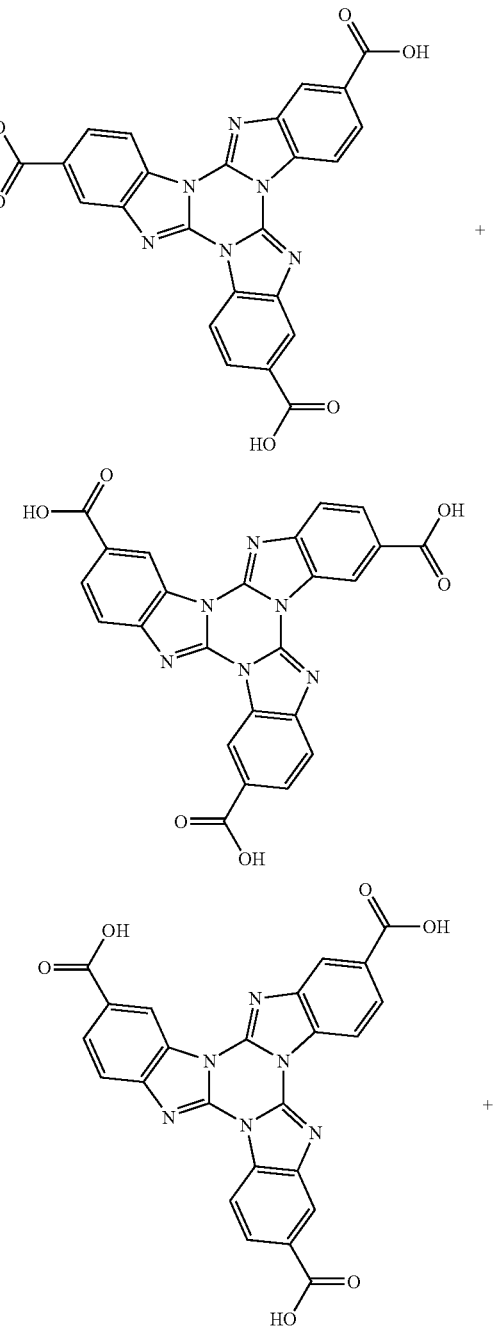

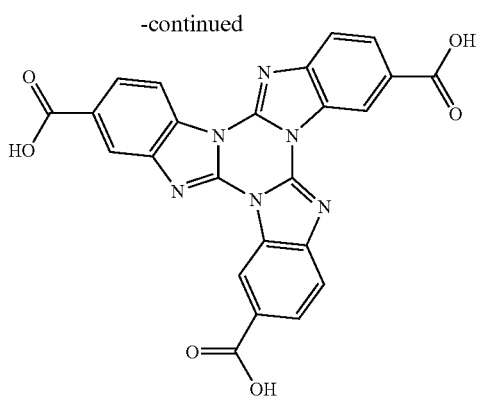

A. Synthesis of methyl 2-oxo-2,3-dihydro-1H-benzimidazole-6-carboxylate

Methyl 3,4-diaminobenzoate dihydrochloride (20 g, 0.08 mol) was mixed with urea (6.54 g, 0.11 mol). Reaction mixture was heated at ~150° C. for 7 hours. After cooling powder was suspended in water (400 ml) and pH of the last one was adjusted to 0.45 with hydrochloric acid. Precipitate was filtered and rinsed with water and hydrochloric acid (pH=1.5). Obtained filter cake was dried at ~100° C. Yield 15.7 g (97%).

B. Synthesis of methyl 2-chloro-1H-benzimidazole-6-carboxylate

Methyl 2-oxo-2,3-dihydro-1H-benzimidazole-6-carboxylate (43 g, 0.22 mol) was charged into Phosphorus oxychloride (286 ml). Dry hydrogen chloride was bubbled through the boiling reaction mass for 12 hours. After cooling reaction mass was poured in mixture of ice and water (2 kg). Precipitate was filtered out. Filtrate was diluted with water (1.25 l) and ammonia solution (~800 ml). After that pH was adjusted to 5.6 with use of ammonia solution. Precipitate was filtered and rinsed with water. Yield 39.5 g (84%).

C. Synthesis of trimethyl bisbenzimidazo[1',2':3,4;1'',2'':5,6][1,3,5]triazino[1,2-a]benzimidazole-tricarboxylates Methyl 2-chloro-1H-benzimidazole-6-carboxylate (38 g, 0.18 mol) was heated at 185-190° C. for 10 hours. Yield 30.3 g (96%).

D. Synthesis of bisbenzimidazo[1',2':3,4;1'',2'':5,6][1,3,5]triazino[1,2-a]benzimidazoletricarboxylic acids Trimethyl bisbenzimidazo[1',2':3,4;1'',2'':5,6][1,3,5]triazino[1,2-a]benzimidazole-tricarboxylates (30 g, 0.06 mol) was charged into 5% solution of potassium hydroxide (250 ml) and boiled for 1.5 hour. After cooling obtained solution was filtered and neutralized with hydrogen chloride solution. Then pH of solution was adjusted to 1.25 with hydrochloric acid. Precipitate was filtered, rinsed with water and dried at ~100° C. Mass spectrum (Ultraflex TOF/TOF (Bruker Daltonics, Bremen, Germany)): M/Z=480 (FW=480.39). Yield 26.3 g (95%).

EXAMPLE 11

The next example describes the preparation of a retardation layer from a solution of polycyclic organic compound schematically shown in FIG. 28: 10 g of a mixture of bisbenzimidazo[1',2':3,4;1'',2'':5,6][1,3,5]triazino[1,2-a]benzimidazole-tricarboxylic acids obtained as in Example 10 is dissolved in 90 g dimethylformamide and stirred at 20° C. until total dissolution of the solid phase and the mixture is stirred for 1 hr under ambient conditions. Then received mixture is filtered. The soda-lime LCD quality glass slides are prepared for coating by treating in a 10% NaOH solution for 30 min, rinsing with deionised water, and drying in airflow with the aid of a compressor. The obtained isotropic solution schematically shown in FIG. 29 is applied onto a glass plate with a Mayer rod #2.5 at a temperature of 20 centigrade and relative humidity of 50%. The layer is dried at the same humidity and temperature in gentle flow of a hot air. Due to specific intermolecular interactions the shear stress is not a main alignment force. As a result, during the drying stage the "flat" molecules are oriented with their plane parallel to the surface of substrate, as shown in FIG. 30. Some kinds of post-treatment procedures (e. g. annealing) may be applied to improve molecules ordering. The refractive indices spectra of the obtained retardation layer are presented in FIG. 20. The obtained retardation layer is optically isotropic in the plane (nf=ns) and exhibits high retardation $R_C$ in the vertical direction. The normal refraction index nn is much lower than the in-plane refraction indices nf and ns. Said retardation layer is named a negative C-plate. Such plate results in optical retardation only for oblique incidence of light. The value of the birefringence (ns−nn) is relatively large (0.25 at λ=550 nm).

EXAMPLE 12

The example describes another preferred embodiment of the liquid crystal display according to the present invention. FIG. 31 schematically shows a light beam (1) and a liquid crystal display which comprises a liquid crystal cell (6) of a vertical alignment mode, a pair of polarizers (2 and 10) arranged on each side of the liquid crystal cell, and one compensating structure (80) disposed between the liquid crystal cell and the first polarizer (2). The transmission axis (11) of the first polarizer is perpendicular to the transmission axis (18) of second polarizer. The compensating structure (80) comprises at least one biaxial retardation layer (85) characterized by two in-plane refractive indices (nf and ns) corresponding to a slow principal axis (90) and a fast principal axis (95) respectively, and one refractive index (nn) in the normal direction (100) which obey the following condition for electromagnetic radiation in the visible spectral range: ns>nn>nf. The retardation layer (85) is arranged such that the fast principal axis (95) of said retardation layer is perpendicular to the transmission axis (11) of the polarizer (2). For the biaxial retardation layer (85) all of the three principal refractive indices nf, ns and nn are different. In still another embodiment of the liquid crystal display, the compensating structure comprising at least one biaxial retardation layer may be disposed between the liquid crystal cell and the second polarizer (10). In yet another embodiment of the present invention, the liquid crystal display comprises two compensating structures. Each of the structures comprises at least one biaxial retardation layer and they are located on each side of the liquid crystal cell.

EXAMPLE 13

The example schematically describes the preparation of a retardation layer from a solution of polycyclic organic compound. FIGS. 32 and 33 demonstrates a simplified sketch of molecular and supramolecular packing in the solution and in the retardation layers with respect to the substrate planes in cases of a uniaxial retardation layer (negative A-plate) which is characterized by two in-plane refractive indices (nf and ns) corresponding to a fast principal axis and a slow principal axis respectively, and one refractive index (nn) in the normal direction which obey the following condition for electromagnetic radiation in the visible spectral range: nn=ns>nf. In solution, the molecules are assembled in rod-like supramolecules as schematically shown in FIG. 32 and can form lyotropic liquid crystal (LLC) in nematic phase. Said rod-like supramolecules have approximately isotropic polarizability in plane (u0w) which is perpendicular to their longitudinal axis directed along 0v-axis. During the deposition process the supramolecules are oriented under shear stress. The result is an ordered uniaxial retardation layer with supramolecules aligned in plane of a substrate along the coating direction, as shown in FIG. 33. FIG. 34 shows a wavelength dependence of refractive indices for said uniaxial thin negative A-plate.

What is claimed is:

1. A liquid crystal display comprising
a vertical alignment mode liquid crystal cell,
two polarizers arranged on each side of the liquid crystal cell, and
at least one compensating structure located between the liquid crystal cell and one of said polarizers,
wherein the polarizers have transmission axes which are perpendicular to each other, and
the compensating structure comprises at least one retardation layer comprising
supramolecules comprising at least one polycyclic organic compound with a conjugated π-system and functional groups which are capable of forming non-covalent bonds between said supramolecules,
the organic compound having a general structural formula I

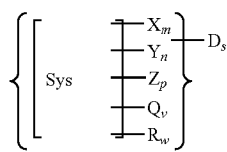
(I)

where Sys is an at least partially conjugated substantially planar polycyclic molecular system,
X is a carboxylic group —COOH,
m is 0, 1, 2, 3 or 4;
Y is a sulfonic group —SO$_3$H,
n is 0, 1, 2, 3 or 4;
Z is a carboxamide,
p is 0, 1, 2, 3 or 4;
Q is a sulfonamide,
v is 0, 1, 2, 3 or 4;
D is a counterion;
s is the number of counterions providing neutral state of the molecule;
R is a substituent selected from the list comprising CH$_3$, C$_2$H$_5$, Cl, Br, NO$_2$, F, CF$_3$, CN, OH, OCH$_3$, OC$_2$H$_5$, OCOCH$_3$, OCN, SCN, NH$_2$, and NHCOCH$_3$, and
w is 0, 1, 2, 3 or 4,
wherein Sys is substantially transparent in the visible spectral range having the general structural formula from the list comprising structures II to IV and VI to XLIX

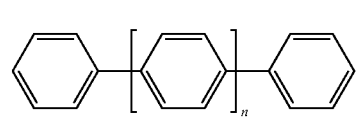
(II)

where n is the number in the range from 1 to 8

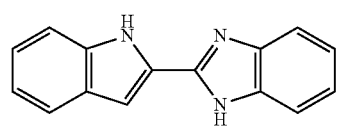
(III)

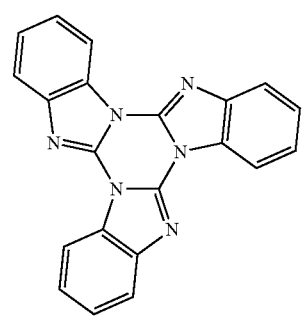
(IV)

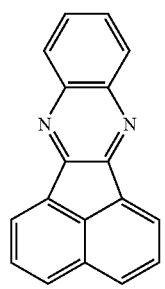
(V)

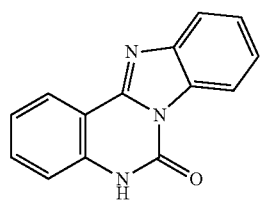
(VI)

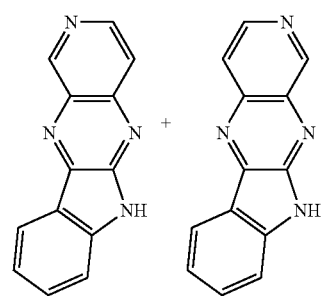
(VII)

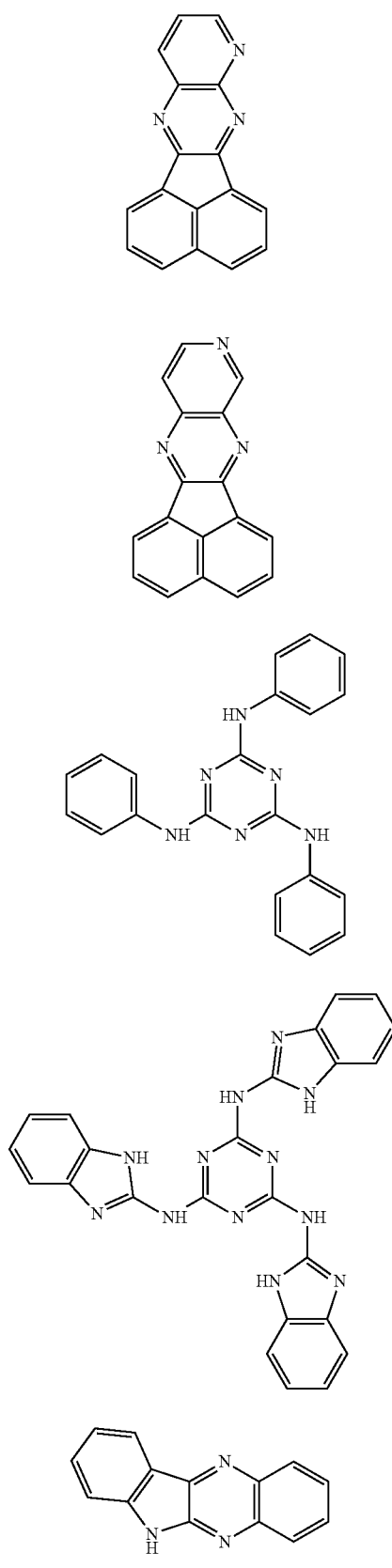

-continued
(XX)
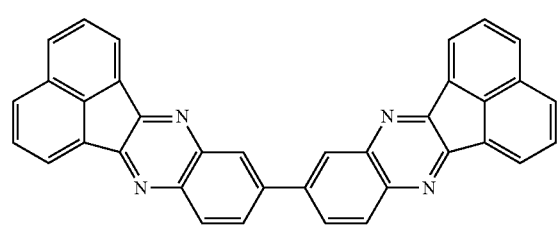
(XXI)
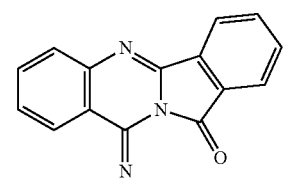
(XXII)
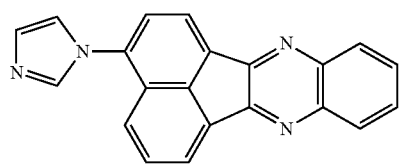
(XXIII)
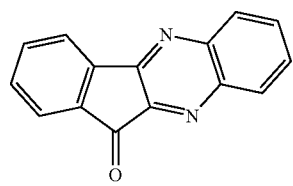
(XXIV)
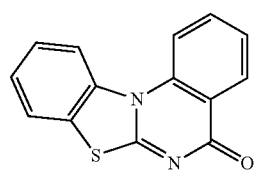
(XXV)
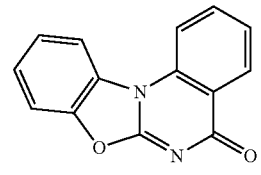
(XXVI)
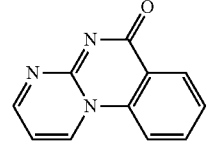
(XXVII)
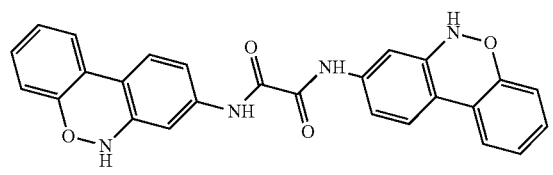
-continued
(XXVIII)
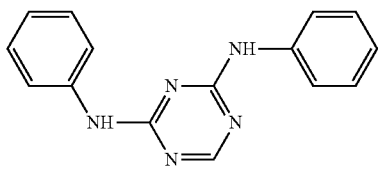
(XXIX)
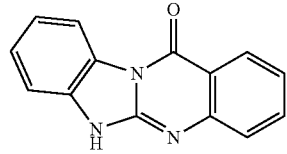
(XXX)
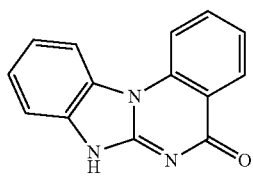
(XXXI)
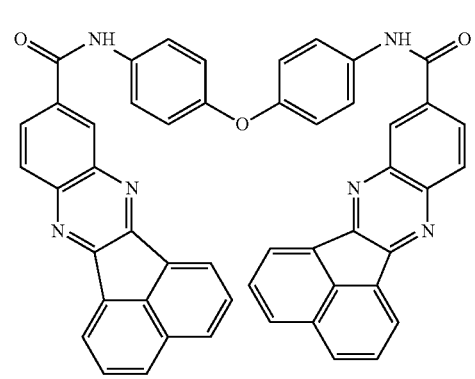
(XXXII)
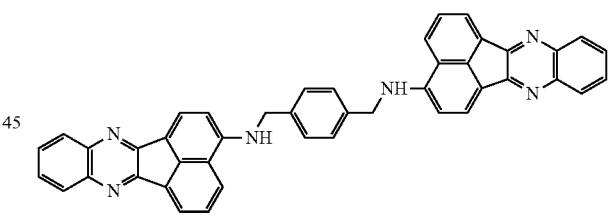
(XXXIII)
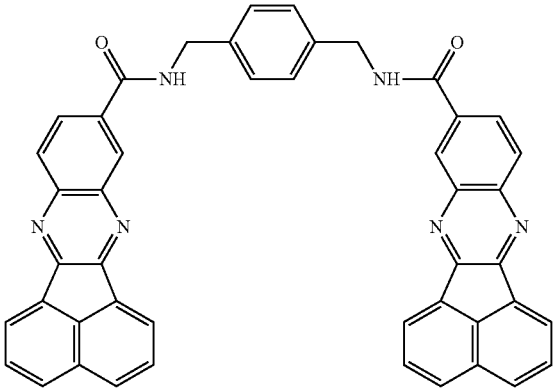

-continued
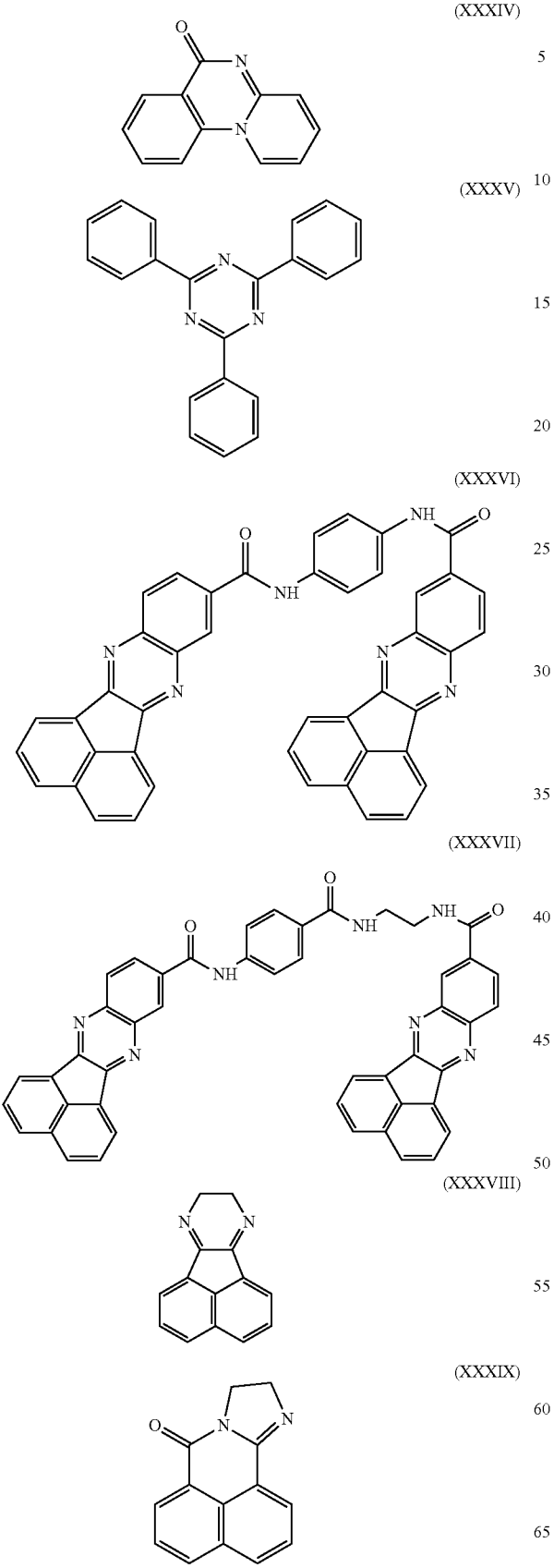
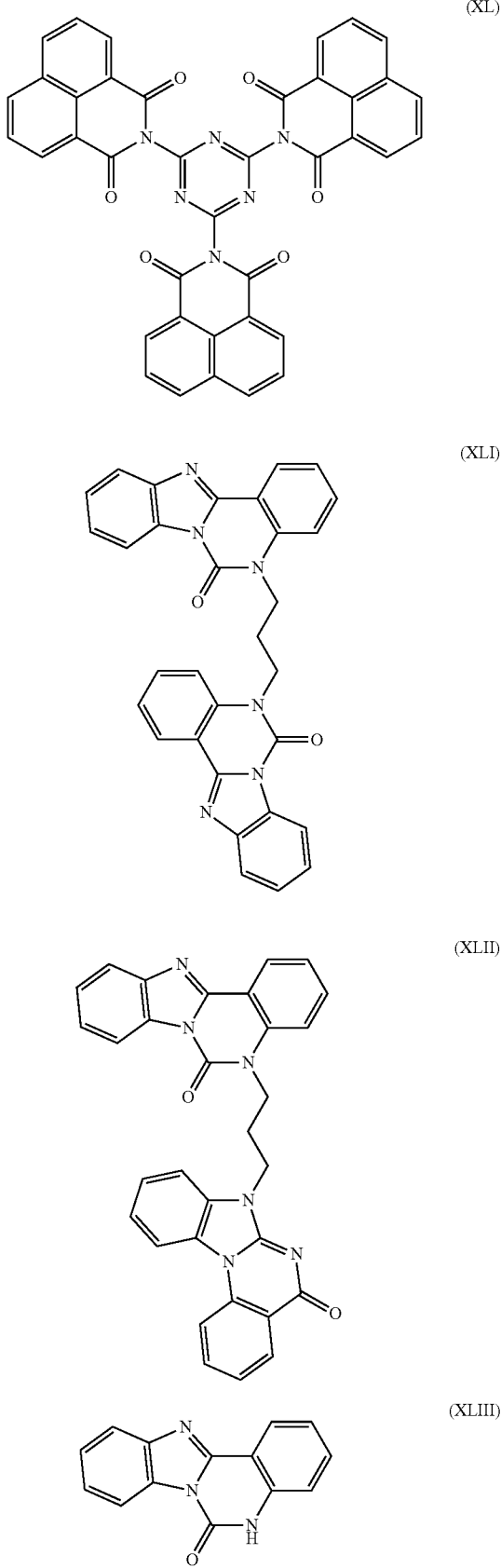

(XLIV)
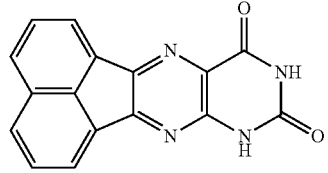
(XLV)
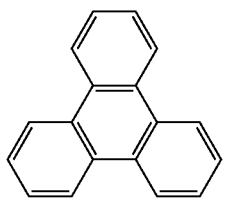
(XLVI)
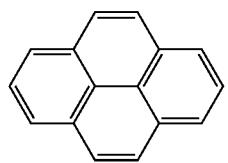
(XLVII)
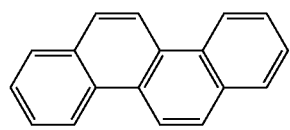
(XLVIII)
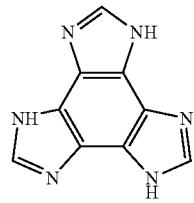
(XLIX)
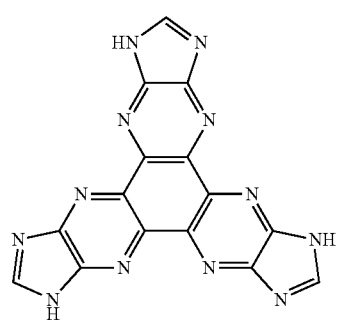
or wherein the organic compound is an acenaphthoquinoxaline derivative having a general structural formula corresponding to one of structures 13 to 25:
(13)
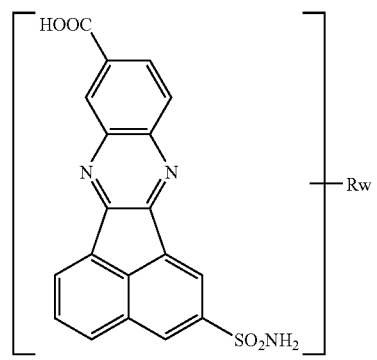
(14)
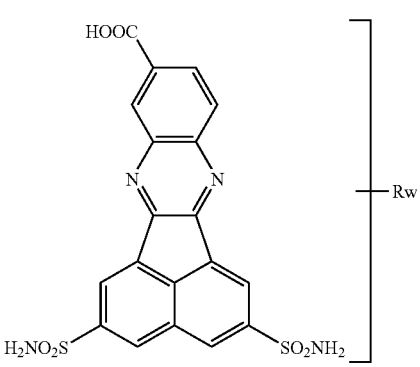
(15)
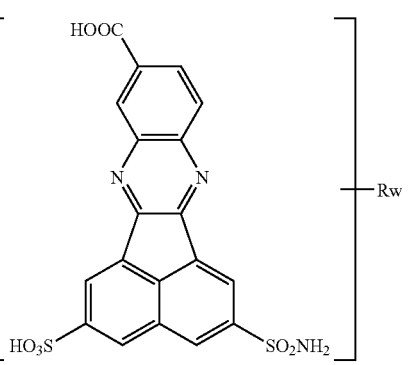
(16)
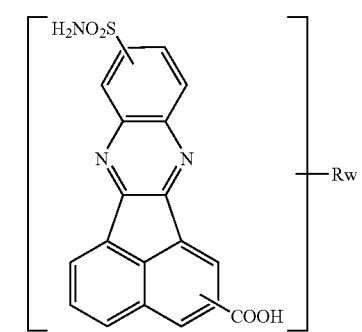

-continued
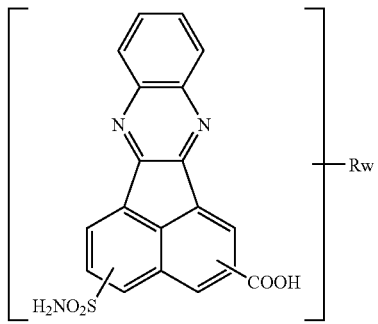
(17)
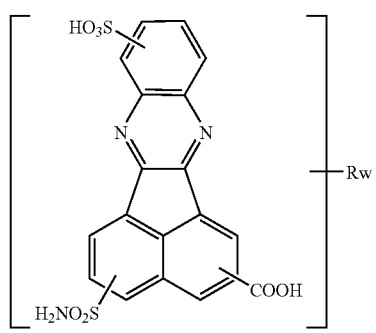
(18)
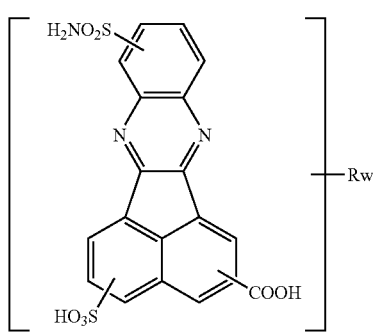
(19)
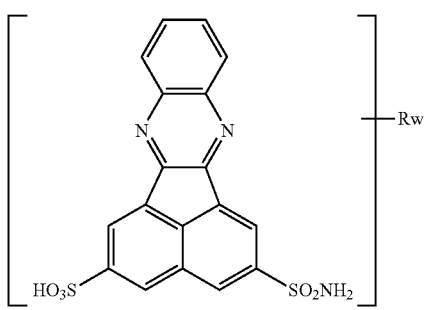
(20)
-continued
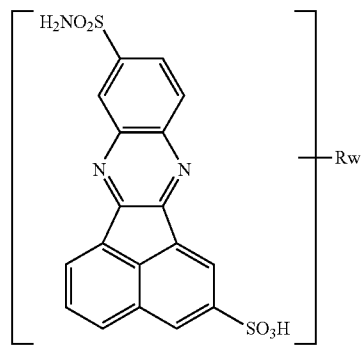
(21)
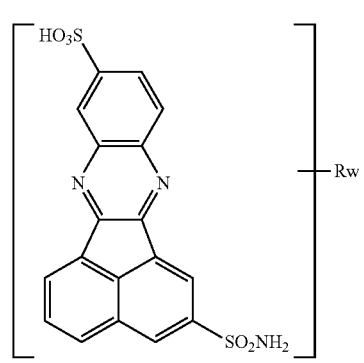
(22)
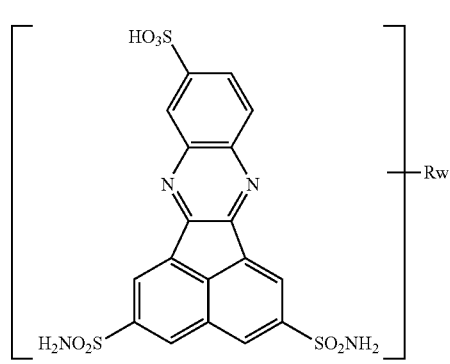
(23)
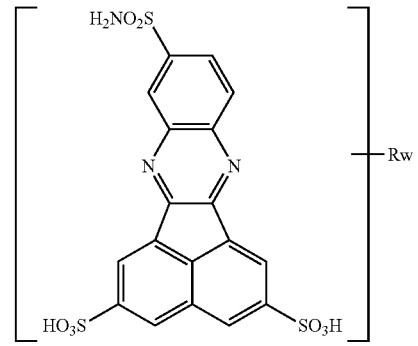
(24)

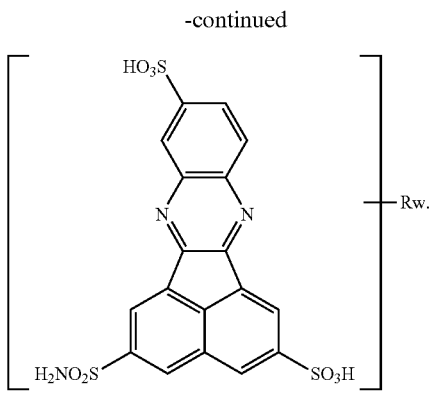
(25)
2. A liquid crystal display according to claim 1, wherein the counterion is selected from the list comprising ions of H⁺, NH₄⁺, Na⁺, K⁺, Li⁺, Ba⁺⁺, Ca⁺⁺, Mg⁺⁺, Sr⁺⁺, Cs⁺, Pb⁺⁺, and Zn⁺⁺.
3. A liquid crystal display according to claim 1, wherein the organic compound is an oligophenyl derivative, having a general structural formula corresponding to one of structures 1 to 7:
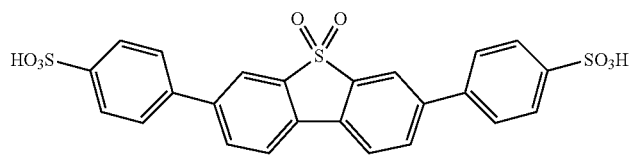
(1)
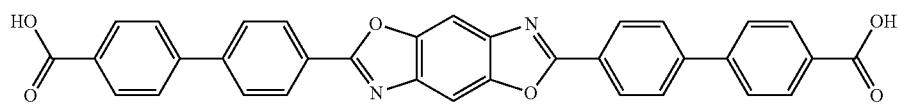
(2)
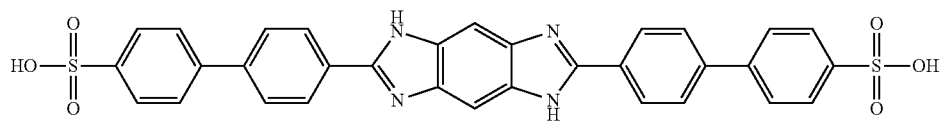
(3)
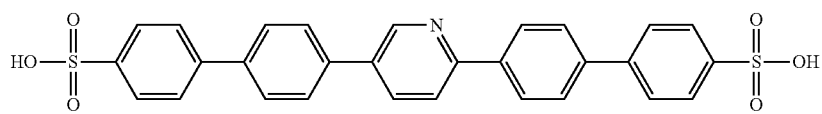
(4)
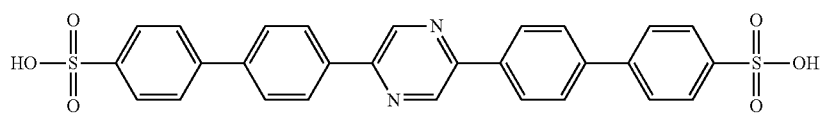
(5)
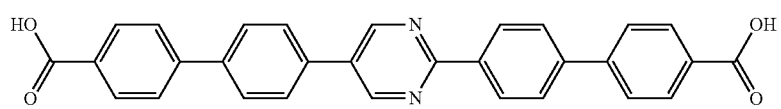
(6)
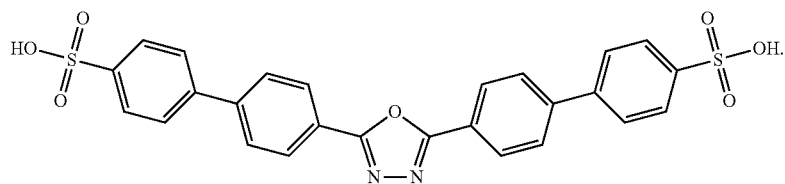
(7)

4. A liquid crystal display according to claim 1, wherein the organic compound is a bibenzimidazole derivative and has a general structural formula corresponding to one of structures 8 to 9:

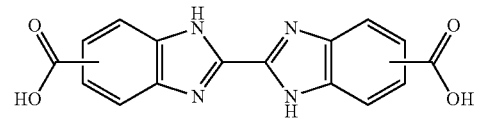
(8)

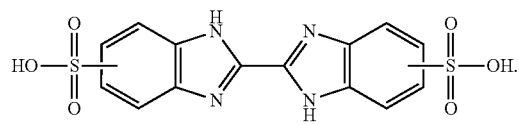
(9)

5. A liquid crystal display according to claim 1, wherein the organic compound is a "triazine" derivative and has a general structural formula corresponding to one of structures 10 to 12:

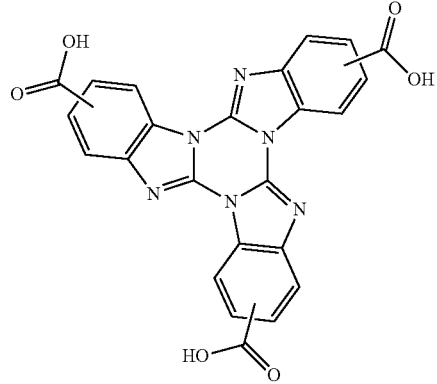
(10)

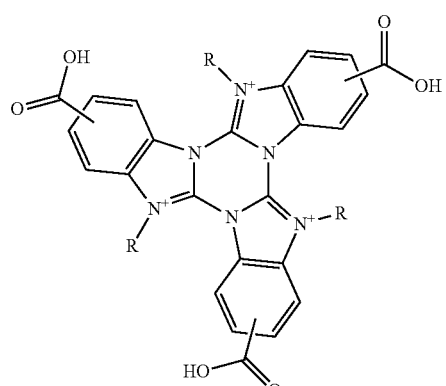
(11)

R = CH₃, C₂H₅, C₃H₇, C₄H₉

-continued

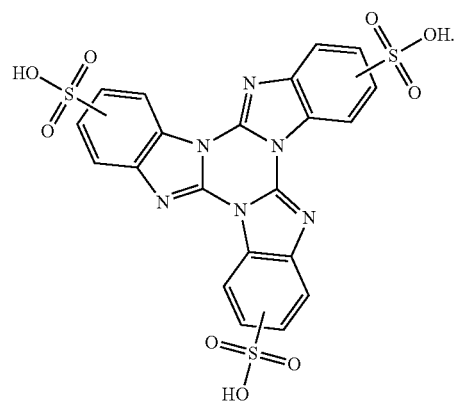
(12)

6. A liquid crystal display according to claim 1, wherein the organic compound is a 6,7-dihydrobenzimidazo[1,2-c]quinazolin-6-one derivative comprising at least one carboxylic group —COOH, m is 1, 2 or 3, and said derivative has a general structural formula from the group comprising structures 32 to 44:

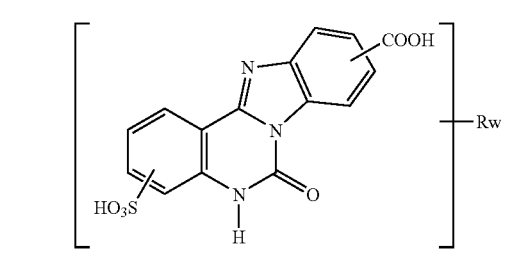
(32)

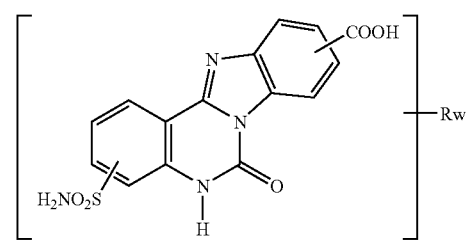
(33)

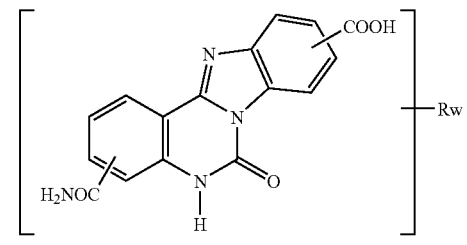
(34)

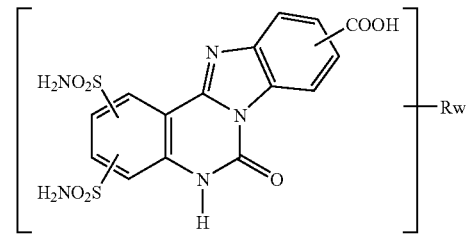
(35)

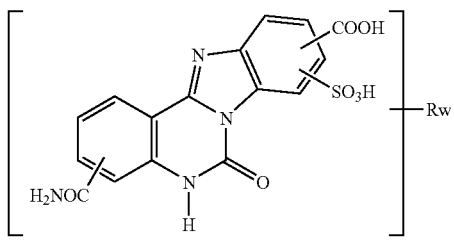 (36)
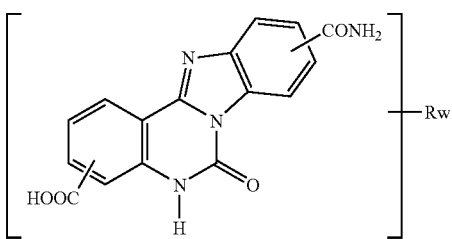 (42)
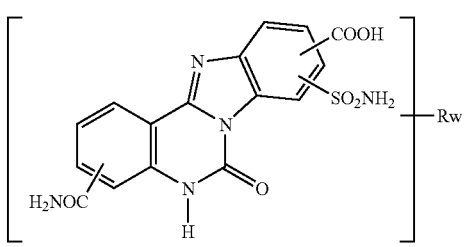 (37)
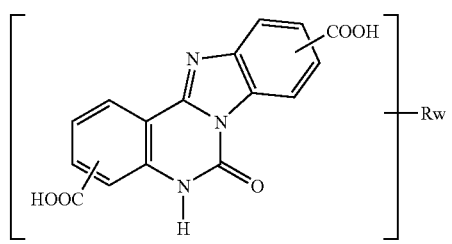 (43)
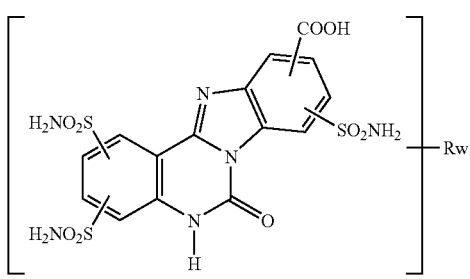 (38)
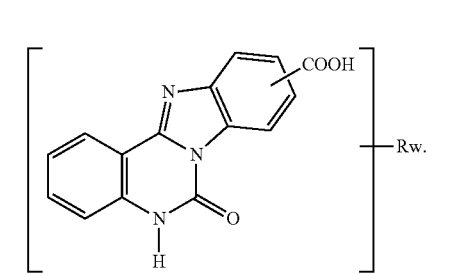 (44)
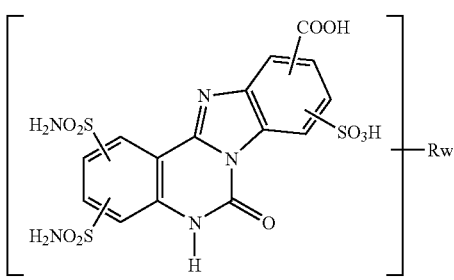 (39)
7. A liquid crystal display according to claim 1, wherein the organic compound is a 6,7-dihydrobenzimidazo[1,2-c]quinazolin-6-one derivative comprising at least one said sulfonic group —SO$_3$H, n is 1, 2 or 3, and said derivative has a general structural formula from the list comprising structures 45 to 53:
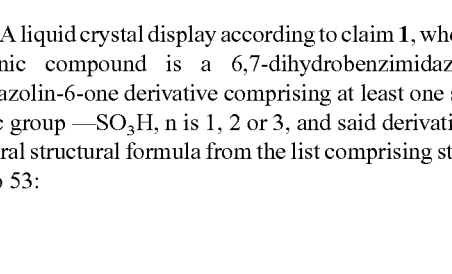 (45)
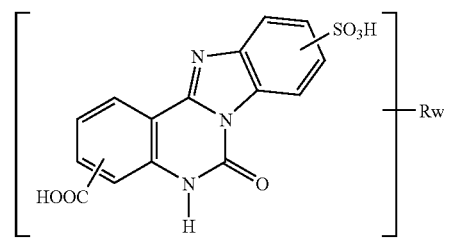 (40)
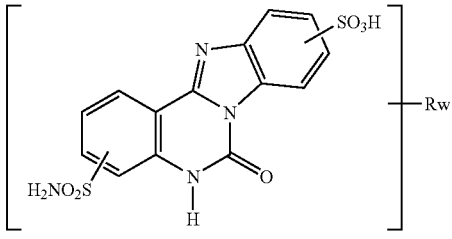 (46)
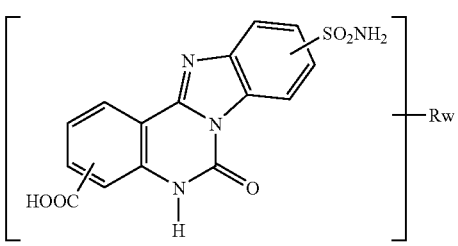 (41)

-continued

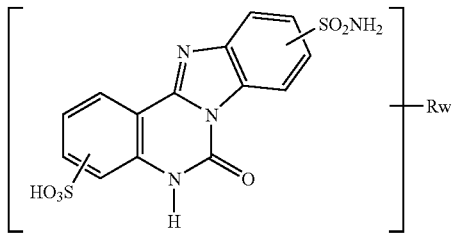 (47)

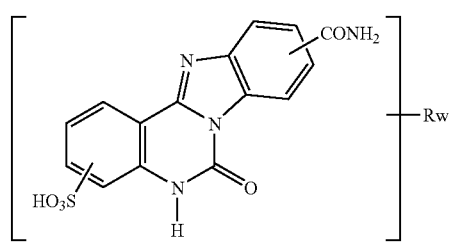 (48)

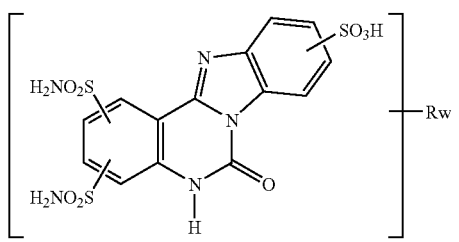 (49)

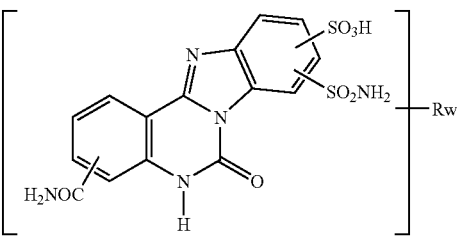 (50)

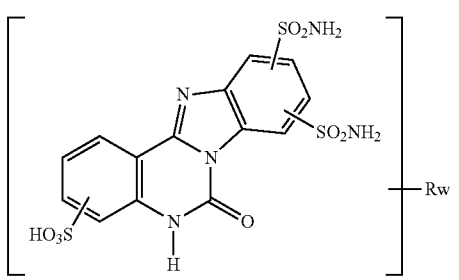 (51)

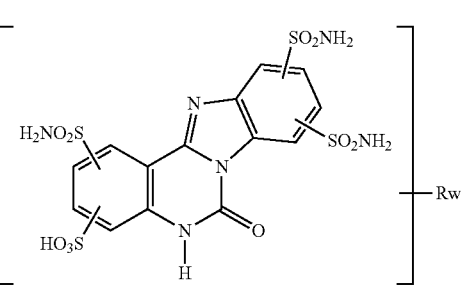 (52)

-continued

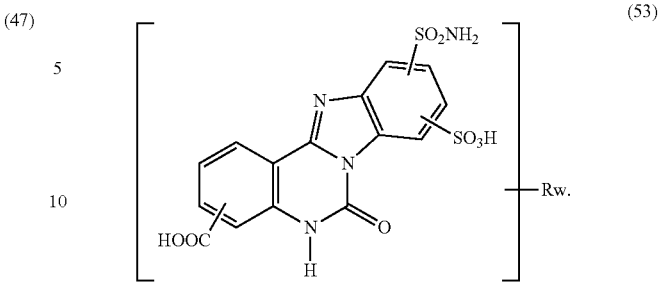 (53)

8. A liquid crystal display according to claim 1, wherein the liquid crystal cell comprises: first and second substrates opposing each other and being substantially parallel to each other, a first electrode provided on a first surface of said first substrate, said first surface facing said second substrate, a second electrode provided on a second surface of said second substrate, said second surface facing said first substrate, a first molecular alignment film provided on said first surface of said first substrate so as to cover said first electrode, a second molecular alignment film provided on said second surface of said second substrate so as to cover said second electrode, and a liquid crystal layer confined between said first and second substrates, and said liquid crystal layer containing liquid crystal molecules of a negative dielectric anisotropy.

9. A liquid crystal display according to claim 1, wherein the retardation layer is a biaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: ns>nn>nf.

10. A liquid crystal display according to claim 9, wherein the retardation layer is arranged such that the fast axis of said retardation layer is substantially perpendicular to the transmission axis of the adjacent polarizer.

11. A liquid crystal display according to claim 9, wherein the retardation layer is arranged such that the fast axis of said retardation layer is substantially parallel to the transmission axis of the adjacent polarizer.

12. A liquid crystal display according to claim 9, wherein the retardation layer comprises rod-like supramolecules which are oriented with their longitudinal axes substantially parallel to the fast principal axis, wherein said rod-like supramolecules have anisotropic polarizability in planes which are perpendicular to their longitudinal axes.

13. A liquid crystal display according to claim 1, wherein the compensating structure comprises at least one retardation layer of a first type having slow and fast principal axes lying substantially in the plane of the first type retardation layer, and at least one retardation layer of a second type having an optical axis directed substantially perpendicular to the plane of the second type retardation layer.

14. A liquid crystal display according to claim 13, wherein the retardation layer of the first type is a uniaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: nn=ns>nf.

15. A liquid crystal display according to claim 14, wherein the retardation layer of the first type comprises rod-like supramolecules which are oriented with their longitudinal axes substantially parallel to the fast principal axis.

16. A liquid crystal display according to claim 15, wherein said rod-like supramolecules have approximately isotropic polarizability in planes which are perpendicular to their longitudinal axes.

17. A liquid crystal display according to claim 13, wherein the retardation layer of the first type is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, nn>nf, and |nn−ns|/(nn+ns)<0.1.

18. A liquid crystal display according to claim 13, wherein the retardation layer of the first type is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf, ns>nn, and |nn−nf|/(nn+nf)<0.1.

19. A liquid crystal display according to claim 18, wherein the retardation layer of the first type is a biaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: ns>nn>nf.

20. A liquid crystal display according to claim 13, wherein the retardation layer of the first type comprises rod-like supramolecules which are oriented with their longitudinal axes substantially parallel to the fast principal axis, wherein said rod-like supramolecules have anisotropic polarizability in planes which are perpendicular to their longitudinal axes.

21. A liquid crystal display according to claim 13, wherein the retardation layer of the first type is arranged such that the fast axis of said retardation layer is substantially perpendicular to the transmission axis of the adjacent polarizer.

22. A liquid crystal display according to claim 13, wherein the retardation layer of the first type is arranged such that the fast axis of said retardation layer is substantially parallel to the transmission axis of the adjacent polarizer.

23. A liquid crystal display according to claim 13, wherein the retardation layer of the second type is a uniaxial retardation layer characterized by two in-plane refractive indices (nf and ns) corresponding to a fast principal axis and a slow principal axis respectively, and one refractive index (nn) in the normal direction which obey the following condition for electromagnetic radiation in the visible spectral range: nf=ns>nn.

24. A liquid crystal display according to claim 13, wherein the retardation layer of the second type is a slightly biaxial retardation layer characterized by two in-plane refractive indices (nf and ns) corresponding to a fast principal axis and a slow principal axis respectively, and one refractive index (nn) in the normal direction which obey the following conditions for electromagnetic radiation in the visible spectral range: ns>nf>nn, and (ns−nf)/(ns+nf)<0.1.

25. A liquid crystal display according to claim 13, wherein the retardation layer of the second type comprises sheet-like supramolecules which are oriented with their plane substantially parallel to the surface of said retardation layer.

26. A liquid crystal display according to claim 13, wherein the retardation layer of the second type comprises flat polycyclic organic compounds, which are oriented with their plane substantially parallel to the surface of said retardation layer.

27. A liquid crystal display according to claim 26, wherein the retardation layer of the second type comprises rod-like supramolecules which are oriented with their longitudinal axes substantially perpendicular to the surface of said retardation layer.

28. A liquid crystal display according to claim 13, wherein the retardation layer of the second type comprises triacetyl cellulose (TAC).

29. A liquid crystal display according to claim 13, wherein said compensating structure comprises the retardation layer of the second type located closer to said liquid crystal cell as compared to the retardation layer of the first type.

30. A liquid crystal display according to claim 13, wherein said compensating structure comprises the retardation layer of the first type located closer to said liquid crystal cell as compared to the retardation layer of the second type.

31. A liquid crystal display according to claim 13, wherein said compensating structure comprises first and second retardation layers of second type arranged on each side of one retardation layer of a first type.

32. A liquid crystal display according to claim 1, comprising at least two compensating structures located on each side of the liquid crystal cell.

* * * * *